(12) United States Patent
Muthuppalaniappan et al.

(10) Patent No.: US 8,993,612 B2
(45) Date of Patent: Mar. 31, 2015

(54) MODULATORS OF CALCIUM RELEASE-ACTIVATED CALCIUM CHANNEL AND METHODS FOR TREATMENT OF NON-SMALL CELL LUNG CANCER

(75) Inventors: Meyyappan Muthuppalaniappan, Hyderabad (IN); Srikant Viswanadha, Hyderabad (IN); Kanthikiran V S Varanasi, Hyderabad (IN); Gayatri Swaroop Merikapudi, Hyderabad (IN); Swaroop Kumar V. S. Vakkalanka, La Chaux-de-Fonds (CH)

(73) Assignee: Rhizen Pharmaceuticals SA, La Chaux-de-Fonds (CH)

( * ) Notice: Subject to any disclaimer, the term of this patent is extended or adjusted under 35 U.S.C. 154(b) by 9 days.

(21) Appl. No.: 12/899,410

(22) Filed: Oct. 6, 2010

(65) Prior Publication Data

US 2011/0112058 A1   May 12, 2011

Related U.S. Application Data

(60) Provisional application No. 61/265,540, filed on Dec. 1, 2009.

(30) Foreign Application Priority Data

Oct. 8, 2009 (IN) ............................ 2439/CHE/2009
Oct. 30, 2009 (IN) ............................ 2636/CHE/2009
Jan. 25, 2010 (IN) ............................. 158/CHE/2010
Jun. 2, 2010 (IN) ............................ 1513/CHE/2010
Jun. 2, 2010 (IN) ............................ 1514/CHE/2010
Aug. 19, 2010 (IN) ............................ 2385/CHE/2010

(51) Int. Cl.

| A61K 31/4155 | (2006.01) |
|---|---|
| A61K 31/4184 | (2006.01) |
| A61K 31/4192 | (2006.01) |
| A61K 31/4709 | (2006.01) |
| A61K 31/498 | (2006.01) |
| A61K 31/437 | (2006.01) |
| A61K 31/52 | (2006.01) |
| A61P 35/00 | (2006.01) |
| C07D 403/12 | (2006.01) |
| C07D 401/12 | (2006.01) |
| C07D 471/04 | (2006.01) |
| C07D 487/04 | (2006.01) |

(52) U.S. Cl.
CPC ............ C07D 403/12 (2013.01); C07D 401/12 (2013.01); C07D 471/04 (2013.01); C07D 487/04 (2013.01)
USPC ........ 514/406; 514/314; 514/300; 514/263.2; 514/249; 514/415; 514/394; 514/359; 548/377.1; 548/364.7; 548/364.4; 548/261; 546/121; 546/175

(58) Field of Classification Search
CPC ........... A61K 31/4155; A61K 31/4184; A61K 31/4192; A61K 31/4709; A61K 31/498; A61K 31/437; A61K 31/52
USPC .............. 514/406, 314, 300, 263.2, 249, 415, 514/394, 359; 548/377.1, 364.7, 364.4, 548/261; 546/121, 175
See application file for complete search history.

(56) References Cited

U.S. PATENT DOCUMENTS

| 6,348,480 B1 | 2/2002 | Kubota et al. |
|---|---|---|
| 6,696,267 B2 | 2/2004 | Normant et al. |
| 7,452,675 B2 | 11/2008 | Penner et al. |
| 2001/0044445 A1 | 11/2001 | Bamaung et al. |
| 2006/0173006 A1 | 8/2006 | Sun et al. |
| 2007/0249051 A1 | 10/2007 | Bohnert et al. |
| 2008/0293092 A1 | 11/2008 | Stauderman et al. |
| 2009/0023177 A1 | 1/2009 | Penner et al. |
| 2009/0311720 A1 | 12/2009 | Roos et al. |
| 2010/0087415 A1 | 4/2010 | Whitten et al. |
| 2010/0152241 A1 | 6/2010 | Whitten |

FOREIGN PATENT DOCUMENTS

| EP | 1875925 A1 | 1/2008 |
|---|---|---|
| WO | WO-9962885 A1 | 12/1999 |
| WO | WO-02089793 A1 | 11/2002 |
| WO | WO-03022852 A2 | 3/2003 |
| WO | WO-03045912 A1 | 6/2003 |
| WO | WO-2004078995 A2 | 9/2004 |
| WO | WO-2005009539 A2 | 2/2005 |
| WO | WO-2005009954 A2 | 2/2005 |
| WO | WO-2005095351 A1 | 10/2005 |
| WO | WO-2006034402 A2 | 3/2006 |
| WO | WO-2006050214 A2 | 5/2006 |
| WO | WO-2006081389 A1 | 8/2006 |
| WO | WO-2006081391 A2 | 8/2006 |
| WO | WO-2007004038 A1 | 1/2007 |
| WO | WO-2007087427 A2 | 8/2007 |
| WO | WO-2007087429 A2 | 8/2007 |
| WO | WO-2007087441 A2 | 8/2007 |
| WO | WO-2007087442 A2 | 8/2007 |
| WO | WO-2007087443 A2 | 8/2007 |
| WO | WO-2007089904 A2 | 8/2007 |

(Continued)

OTHER PUBLICATIONS

Williams et al. Foye's Principles of Medicinal Chemistry, 5th Edition, 2002, p. 59.*

(Continued)

Primary Examiner — Sreeni Padmanabhan
Assistant Examiner — Irina Neagu
(74) Attorney, Agent, or Firm — Blank Rome LLP

(57) ABSTRACT

Disclosed are novel calcium release-activated calcium (CRAC) channel inhibitors, methods for preparing them, pharmaceutical compositions containing them, and methods of treatment using them. The present disclosure also relates to methods for treating non-small cell lung cancer (NSCLC) with CRAC inhibitors, and to methods for identifying therapeutics for treating and of diagnosing cancer.

14 Claims, 5 Drawing Sheets

(56) References Cited

FOREIGN PATENT DOCUMENTS

| | | |
|---|---|---|
| WO | WO-2007109362 A2 | 9/2007 |
| WO | WO-2007112093 A2 | 10/2007 |
| WO | WO-2007121186 A2 | 10/2007 |
| WO | WO-2007139926 A2 | 12/2007 |
| WO | WO-2008016643 A2 | 2/2008 |
| WO | WO-2008039520 A2 | 4/2008 |
| WO | WO-2008063504 A2 | 5/2008 |
| WO | WO-2008103310 A1 | 8/2008 |
| WO | WO-2008106731 A1 | 9/2008 |
| WO | WO-2008148108 A1 | 12/2008 |
| WO | WO-2009017818 A1 | 2/2009 |
| WO | WO-2009017819 A1 | 2/2009 |
| WO | WO-2009017831 A1 | 2/2009 |
| WO | WO-2009035818 A1 | 3/2009 |
| WO | WO-2009038775 A1 | 3/2009 |
| WO | WO-2009076454 A2 | 6/2009 |
| WO | WO-2009089305 A1 | 7/2009 |
| WO | WO-2010025295 A2 | 3/2010 |
| WO | WO-2010027875 A2 | 3/2010 |
| WO | WO-2010034003 A2 | 3/2010 |
| WO | WO-2010034011 A2 | 3/2010 |
| WO | WO-2010039236 A1 | 4/2010 |
| WO | WO-2010039237 A1 | 4/2010 |
| WO | WO-2010039238 A1 | 4/2010 |
| WO | WO-2010048559 A2 | 4/2010 |

OTHER PUBLICATIONS

Patani et al. Chemical Reviews 1996, 96, 3147-3176.*
Haura Cancer Control 2001, 8 (4), 326-336.*
National Cancer Institute at the National Institutes of Health, A to Z List of Cancers, http://www.cancer.gov/cancertopics/types/alphalist/n accessed Jul. 24, 2012.*
Sweeney et al. ChemMedChem 2009, 4, 706-718.*
Stella et al. Prodrugs: Challenges and Rewards, Springer New York 2007.*
Rami-Porta et al. Journal of Thoracic Oncology 2007, 2 (7), 593-602.*
Dubey et al. Lancet Oncology 2006, 7 (5), 416-424, Abstract.*
Goldstein et al. Intellectual Property Today 2008, 15 (8), 10-11.*
Yonetoku, et al., Novel potent and selective calcium-release-activated calcium (CRAC) channel inhibitors. Part 1: Synthesis and inhibitory activity of 5-(1-methyl-3-trifluoromethyl-1H-pyrazol-5-yl)-2-thiophenecarboxamides, Bioorganic & Medicinal Chemistry 14 (2006) 4750-4760.
Yonetoku, et al., Novel potent and selective calcium-release-activated calcium (CRAC) channel inhibitors. Part 2: Synthesis and inhibitory activity of aryl-3-trifluoromethylpyrazoles, Bioorganic & Medicinal Chemistry 14 (2006) 5370-5383.
Yonetoku, et al., Novel Potent and Selective Ca2+ release-activated Ca2+ (CRAC) channel inhibitors. Part 3: Synthesis and CRAC channel inhibitory activity of 4'-[trifluoromethyl)pyrazol-1-yl]carboxanilides, Bioorganic & Medicinal Chemistry 16 (2008) 9457-9466.
Yasurio Yonetoky et al., *Bio. & Med. Chem.*, 14, 4750-4760, 2006.
Yasurio Yonetoky et al., *Bio. & Med. Chem.*, 14, 5370-5383, 2006.
U.S. Appl. No. 12/899,416, filed on Oct. 6, 2010.
International Search Report for PCT/IB2010/002535.
Isabella Derler et al., *Expert Opinion in Drug Discovery*, 3(7), 787-800, 2008.
Taiji et al. (*European Journal of Pharmacology* 560, 225-233, 2007).
Yasuhiro Yonetoku et al. (*Bio. & Med. Chem.*, 16, 9457-9466, 2008).
Yousang G et al., Cell Calcium, 42, 145-156, 2007.
International Search Report for PCT/IB2010/002539.

* cited by examiner

FIG. 1: mRNA expression of *Orai1* and *Stim1* in A549 & NCI-H460 cell lines. Jurkat mRNA was used as control
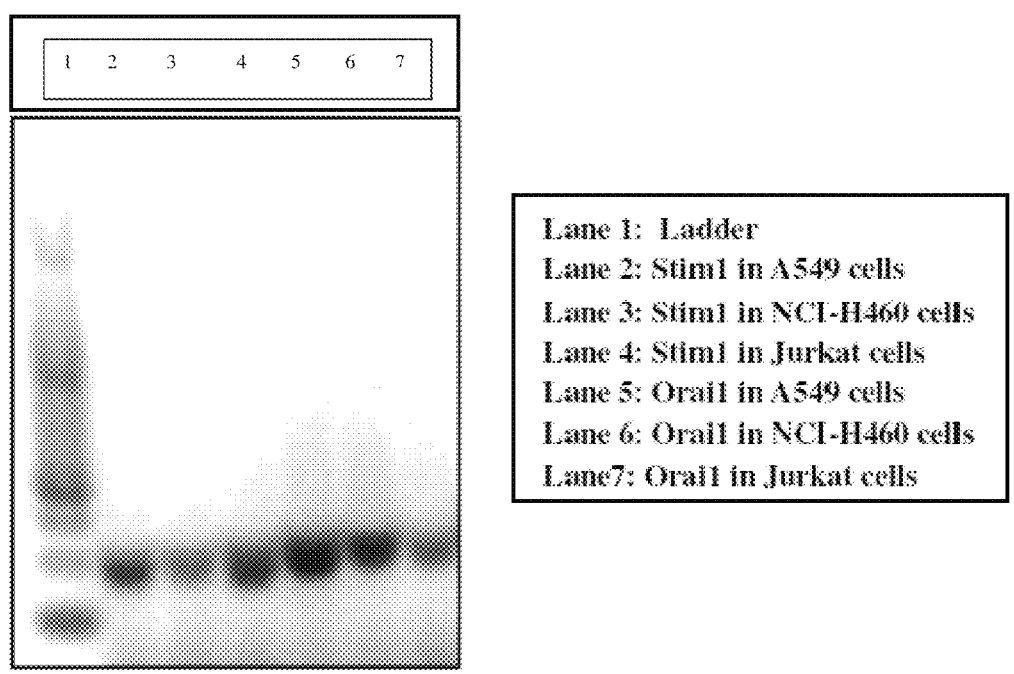

FIG. 2: Inhibition of Thapsigargin (TG) induced calcium influx in NCI-H460 Cells
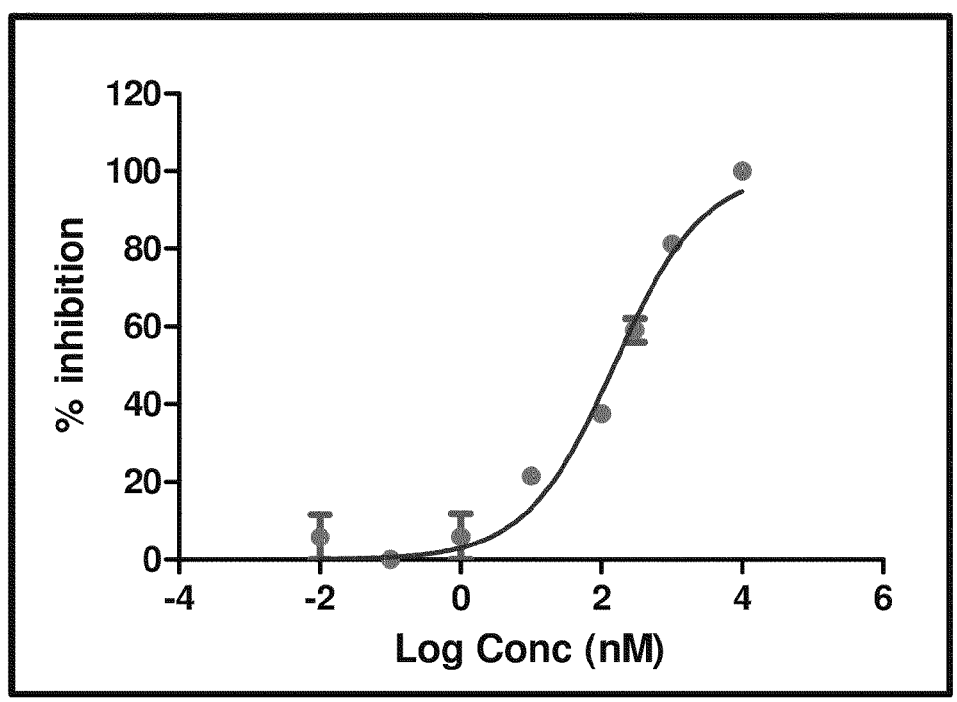

FIG. 3: Inhibition of NCI-H460 cell proliferation for Compound A
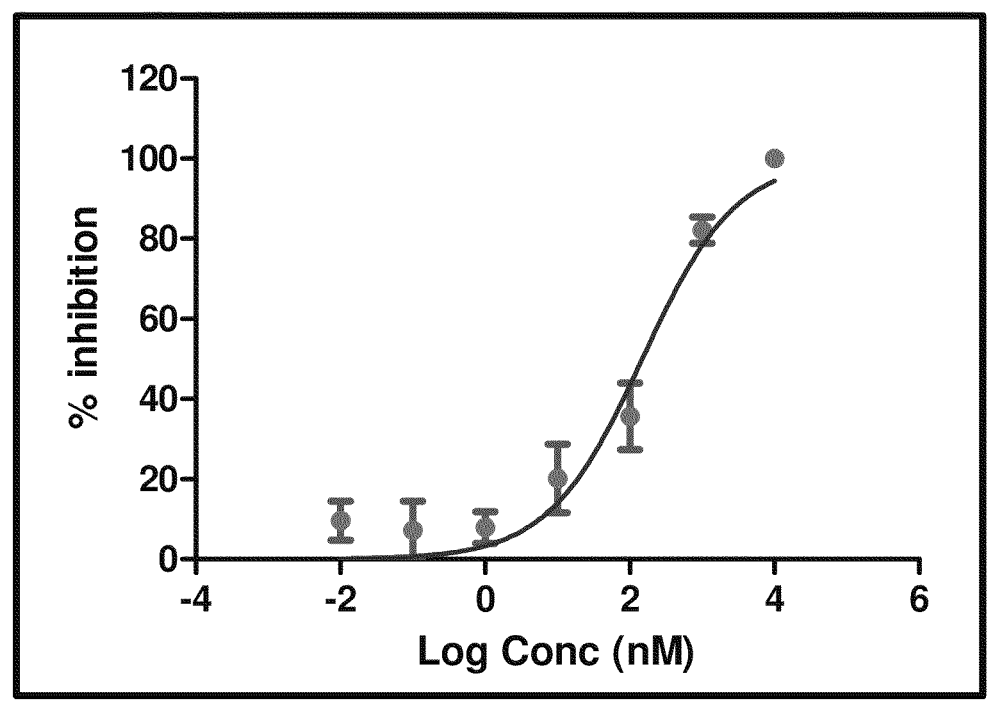

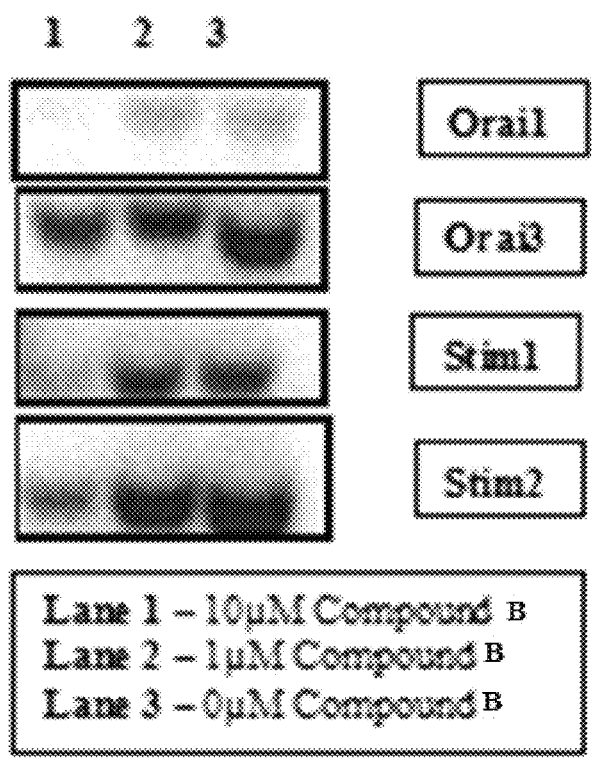
Fig.4: Effect of compound B on Orai & STIM expression in NCI-H460 cell line Fig. 5: Inhibition of Tumour Growth in Female Balb/c Nude Mice Bearing NCI-H460 Non-Small Cell Lung CancerXenograft.
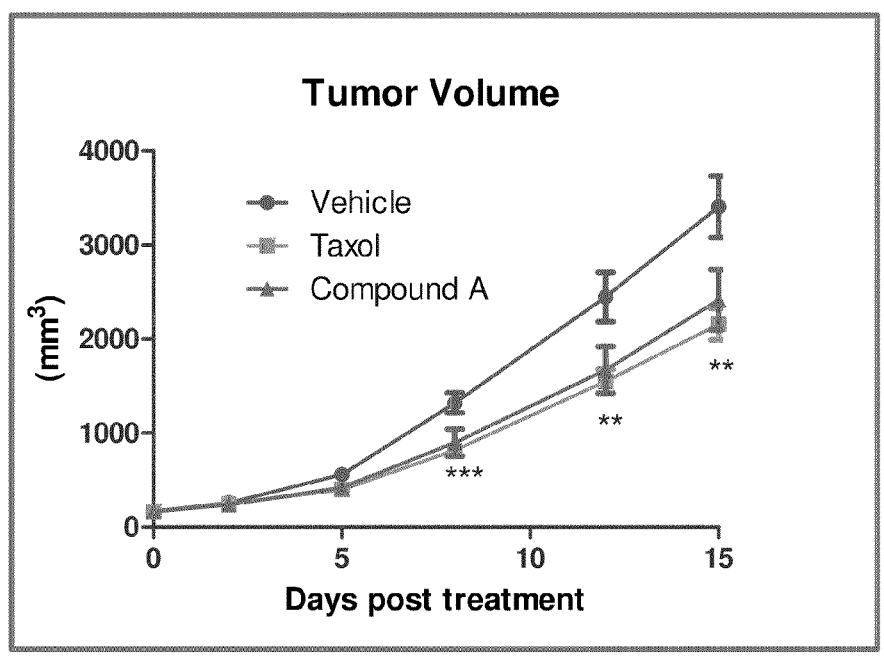

1 …

SEQUENCE LISTING

```
<160> NUMBER OF SEQ ID NOS: 10

<210> SEQ ID NO 1
<211> LENGTH: 22
<212> TYPE: DNA
<213> ORGANISM: Artificial Sequence
<220> FEATURE:
<223> OTHER INFORMATION: Forward PCR primer for Orai1 (calcium release
      activated calcium channel modulator 1)

<400> SEQUENCE: 1
catggtggca atggtggagg tg                                              22

<210> SEQ ID NO 2
<211> LENGTH: 21
<212> TYPE: DNA
<213> ORGANISM: Artificial Sequence
<220> FEATURE:
<223> OTHER INFORMATION: Reverse PCR primer for Orai1 (calcium release
      activated calcium channel modulator 1)

<400> SEQUENCE: 2
aggcactgaa ggcgatgagc a                                               21

<210> SEQ ID NO 3
<211> LENGTH: 19
<212> TYPE: DNA
<213> ORGANISM: Artificial Sequence
<220> FEATURE:
<223> OTHER INFORMATION: Forward PCR primer for Orai2

<400> SEQUENCE: 3
atggtgccat ggtggaggt                                                  19

<210> SEQ ID NO 4
<211> LENGTH: 19
<212> TYPE: DNA
<213> ORGANISM: Artificial Sequence
```

```
<220> FEATURE:
<223> OTHER INFORMATION: Reverse PCR primer for Orai2

<400> SEQUENCE: 4
tgcaggcgct gaaggcaat                                              19

<210> SEQ ID NO 5
<211> LENGTH: 21
<212> TYPE: DNA
<213> ORGANISM: Artificial Sequence
<220> FEATURE:
<223> OTHER INFORMATION: Forward PCR primer for Orai3

<400> SEQUENCE: 5
aagctcaaag cttccagccg c                                           21

<210> SEQ ID NO 6
<211> LENGTH: 22
<212> TYPE: DNA
<213> ORGANISM: Artificial Sequence
<220> FEATURE:
<223> OTHER INFORMATION: Reverse PCR primer for Orai3

<400> SEQUENCE: 6
ggtgggtact cgtggtcact ct                                          22

<210> SEQ ID NO 7
<211> LENGTH: 24
<212> TYPE: DNA
<213> ORGANISM: Artificial Sequence
<220> FEATURE:
<223> OTHER INFORMATION: Forward PCR primer for Stim1 (stromal
      interaction molecule 1)

<400> SEQUENCE: 7
aaggctctgg atacagtgct cttt                                        24

<210> SEQ ID NO 8
<211> LENGTH: 25
<212> TYPE: DNA
<213> ORGANISM: Artificial Sequence
<220> FEATURE:
<223> OTHER INFORMATION: Reverse PCR primer for Stim1 (stromal
      interaction molecule 1)

<400> SEQUENCE: 8
agcatgaagt ccttgaggtg attat                                       25

<210> SEQ ID NO 9
<211> LENGTH: 21
<212> TYPE: DNA
<213> ORGANISM: Artificial Sequence
<220> FEATURE:
<223> OTHER INFORMATION: Forward PCR primer for Stim2

<400> SEQUENCE: 9
acgacacttc ccaggatagc a                                           21

<210> SEQ ID NO 10
<211> LENGTH: 23
<212> TYPE: DNA
<213> ORGANISM: Artificial Sequence
<220> FEATURE:
<223> OTHER INFORMATION: Reverse PCR Primer for Stim2
```

```
<400> SEQUENCE: 10
gactccggtc actgattttc aac                                              23
```

MODULATORS OF CALCIUM RELEASE-ACTIVATED CALCIUM CHANNEL AND METHODS FOR TREATMENT OF NON-SMALL CELL LUNG CANCER

This application claims the benefit of Indian Provisional Patent Application Nos. 2439/CHE/2009 dated 8 Oct. 2009; 2636/CHE/2009 dated 30 Oct. 2009; 158/CHE/2010 dated 25 Jan. 2010; 1513/CHE/2010 dated 2 Jun. 2010; 1514/CHE/2010 dated 2 Jun. 2010; and 2385/CHE/2010 dated 19 Aug. 2010, and U.S. Provisional Patent Application No. 61/265,540 dated 1 Dec. 2009, each of which is hereby incorporated by reference.

FIELD OF THE INVENTION

The present invention relates to calcium release-activated calcium (CRAC) channel inhibitors of formula I and pharmaceutically acceptable salts thereof, methods for preparing them, pharmaceutical compositions containing them, and methods of treatment with them.

The present invention also relates to methods for treating non-small cell lung cancer (NSCLC) with CRAC inhibitors, and methods for identifying therapeutics for treating and of diagnosing cancer.

BACKGROUND OF THE INVENTION

The regulation of intracellular calcium is a key element in the transduction of signals into and within cells. Cellular responses to growth factors, neurotransmitters, hormones and a variety of other signal molecules are initiated through calcium-dependent processes. The importance of calcium ion as a second messenger is emphasised by many different mechanisms which work together to maintain calcium homeostasis. Changes in intracellular free calcium ion concentration represent the most wide-spread and important signalling event for regulating a plethora of cellular responses. A widespread route for calcium ion entry into the cell is through store-operated channels (SOCs), i.e. many cell types employ store-operated calcium ion entry as their principal pathway for calcium ion influx. This mechanism is engaged following calcium ion release from stores, where the depleted stores lead to activation of calcium release-activated calcium (CRAC) channels.

CRAC channels, a subfamily of store-operated channels, are activated by the release of calcium from intracellular stores, particularly from the endoplasmic reticulum (ER). These channels are key factors in the regulation of a wide range of cellular function, including muscle contraction, protein and fluid secretion and control over cell growth and proliferation and hence play an essential role in various diseases such as immune disorders and allergic responses. Among several biophysically distinct store-operated currents the best characterized and most calcium ion selective one is the CRAC current. Thus, CRAC channels mediate essential functions from secretion to gene expression and cell growth and form a network essential for the activation of immune cells that establish the adaptive immune response. Recently two proteins, stromal interaction molecule (STIM1) and CRAC Modulator 1 (CRACM1 or Orai1), have been identified as the essential components that fully reconstitute and amplify CRAC currents in heterologous expression systems with a similar biophysical fingerprint. In mammals, there exist several homologs of these proteins: STIM1 and STIM2 in the endoplasmic reticulum and CRACM1, CRACM2, and CRACM3 in the plasma membrane.

CRAC currents were initially discovered in lymphocytes and mast cells, and at the same time have been characterized in various cell lines such as S2 drosophila, DT40 B cells, hepatocytes, dendritic, megakaryotic, and Madin-Darby canine kidney cells. In lymphocytes and in mast cells, activation through antigen or Fc receptors initiates the release of calcium ion from intracellular stores caused by the second messenger inositol (1,4,5)-triphosphate (Ins(1,4,5)$P_3$), which in turn leads to calcium ion influx through CRAC channels in the plasma membrane. Store-operated $Ca^{2+}$ currents characterized in smooth muscle, A431 epidermal cells, endothelial cells from various tissues, and prostate cancer cell lines show altered biophysical characteristics suggesting a distinct molecular origin.

For example, calcium ion influx across the cell membrane is important in lymphocyte activation and adaptive immune responses. [$Ca^{2+}$]-oscillations triggered through stimulation of the TCR (T-cell antigen receptor) have been demonstrated to be prominent, and appear to involve only a single calcium ion influx pathway, the store-operated CRAC channel. See, e.g., Lewis "Calcium signalling mechanisms in T lymphocytes," Annu. Rev. Immunol. 19, (2001), 497-521; Feske et al. "$Ca^{++}$ calcineurin signalling in cells of the immune system," Biochem. Biophys. Res. Commun 311, (2003), 1117-1132; Hogan et al. "Transcriptional regulation by calcium, calcineurin, and NFAT," Genes Dev. 17, (2003) 2205-2232.

It is well established now that intracellular calcium plays an important role in various cellular functions, and that its concentration is regulated by calcium ion influx through calcium channels on the cell membrane. Calcium ion channels, which are located in the nervous, endocrine, cardiovascular, and skeletal systems and are modulated by membrane potential, are called voltage-operated $Ca^{2+}$ (VOC) channels. These channels are classified into L, N, P, Q, R, and T subtypes. Excessive $Ca^{2+}$ influx through the VOC channels causes hypertension and brain dysfunction. In contrast, calcium ion channels on inflammatory cells, including lymphocytes, mast cells, and neutrophils, can be activated regardless of their membrane potential. This type of calcium ion channel has been reported to act in the crisis and exacerbation of inflammation and autoimmune diseases. In the T cells, it has been reported that the early stages of activation consist of pre- and post-$Ca^{2+}$ events. The stimulation of T cell receptors induces pre-$Ca^{2+}$ events, including the generation of IP3, followed by the release of $Ca^{2+}$ from the endoplasmic reticulum (ER). In post-$Ca^{2+}$ events, depletion of $Ca^{2+}$ in the ER induces the activation of CRAC channels, and capacitative $Ca^{2+}$ influx through the CRAC channel sustains high intracellular $Ca^{2+}$ concentration ([$Ca^{2+}$]i). This prolonged high [Ca2+]i activates cytosolic signal transduction to produce lipid mediators (e.g., $LTD_4$), cytokines [e.g., interleukin-2 (IL-2)], and matrix metalloproteinases, which participate in the pathogenesis of inflammation and autoimmune diseases.

These facts suggest that CRAC channel modulators can be useful for the treatment of diseases caused by the activation of inflammatory cells without side effects observed in steroids. Since VOC channel modulators would cause adverse events in the nervous and cardiovascular systems, it may be necessary for CRAC channel modulators to exhibit sufficient selectivity over VOC channels if they are to be used as anti-inflammatory drugs.

Accordingly, CRAC channel modulators have been said to be useful in treatment, prevention and/or amelioration of diseases or disorders associated with calcium release-activated calcium channel including, but not limited to, inflammation, glomerulonephritis, uveitis, hepatic diseases or disorders, renal diseases or disorders, chronic obstructive pulmonary disease, rheumatoid arthritis, inflammatory bowel disease, vasculitis, dermatitis, osteoarthritis, inflammatory muscle disease, allergic rhinitis, vaginitis, interstitial cystitis, scleroderma, osteoporosis, eczema, allogeneic or xenogeneic transplantation, graft rejection, graft-versus-host disease, lupus erythematosus, type I diabetes, pulmonary fibrosis, dermatomyositis, thyroiditis, myasthenia gravis, autoimmune hemolytic anemia, cystic fibrosis, chronic relapsing hepatitis, primary biliary cirrhosis, allergic conjunctivitis, hepatitis and atopic dermatitis, asthma, Sjogren's syndrome, cancer and other proliferative diseases, and autoimmune diseases or disorders. See, e.g., International Publication Nos. WO 2005/009954, WO 2005/009539, WO 2005/009954, WO 2006/034402, WO 2006/081389, WO 2006/081391, WO 2007/087429, WO 2007/087427, WO 2007087441, WO 200/7087442, WO 2007/087443, WO 2007/089904, WO 2007109362, WO 2007/112093, WO 2008/039520, WO 2008/063504, WO 2008/103310, WO 2009/017818, WO 2009/017819, WO 2009/017831, WO 2010/039238, WO 2010/039237, WO 2010/039236, WO 2009/089305 and WO 2009/038775, and US Publication Nos.: US 2006/0173006 and US 2007/0249051.

CRAC channel inhibitors which have been identified include SK&F 96365 (1), Econazole (2) and L-651582 (3).

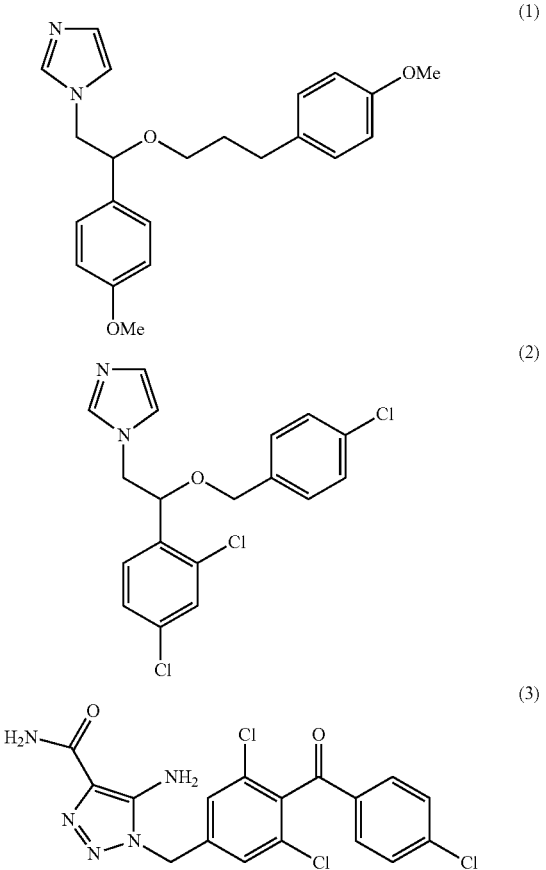

However, these molecules lack sufficient potency and selectivity over VOC channels and hence are not suitable for therapeutic use.

Recent publications by Taiji et al. (*European Journal of Pharmacology*, 560, 225-233, 2007) and Yasurio Yonetoky et al. (*Bio. & Med. Chem.*, 16, 9457-9466, 2008) describe a selective CRAC channel inhibitor coded YM-58483 that is capable of inhibiting T cell function and proposed to be of some benefit in the treatment of inflammatory diseases including bronchial asthma.

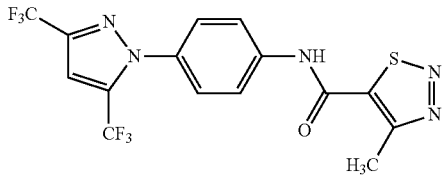

YM-58483

Yasurio Yonetoky et al. disclose YM-58483 to be selective for CRAC channels over the voltage operated channels (VOC) with a selective index of 31.

Other CRAC channel modulators disclosed include various biaryl and/or heterocyclic carboxanilide compounds including for example PCT or US patent applications assigned to Synta Pharmaceuticals viz. WO 2005/009954, WO 2005/009539, WO 2005/009954, WO 2006/034402, WO 2006/081389, WO 2006/081391, WO 2007/087429, WO 2007/087427, WO 2007087441, WO 200/7087442, WO 2007/087443, WO 2007/089904, WO 2007109362, WO 2007/112093, WO 2008/039520, WO 2008/063504, WO 2008/103310, WO 2009/017818, WO 2009/017819, WO 2009/017831, WO 2010/039238, WO 2010/039237, WO 2010/039236, WO 2009/089305 and WO 2009/038775, US 2006/0173006 and US 2007/0249051.

Other patent publications relating to CRAC channel modulators include applications by Astellas, Queens Medical Centre, Calcimedica and others viz., WO 2007/121186, WO 2006/0502 14, WO 2007/139926, WO 2008/148108, U.S. Pat. No. 7,452,675, US 2009/023177, WO 2007/139926, U.S. Pat. No. 6,696,267, U.S. Pat. No. 6,348,480, WO 2008/106731, US 2008/0293092, WO 2010/048559, WO 2010/027875, WO2010/025295, WO 2010/034011, WO2010/034003, WO 2009/076454, WO 2009/035818, US 2010/0152241, US 2010/0087415, US 2009/0311720 and WO 2004/078995.

Further review and literature disclosure in the area of CRAC channels includes Isabella Derler et al., *Expert Opinion in Drug Discovery*, 3(7), 787-800, 2008; Yousang G et al., Cell Calcium, 42, 145-156, 2007; Yasurio Yonetoky et. al., *Bio. & Med. Chem.*, 14, 4750-4760, 2006; and Yasurio Yonetoky et. al., *Bio. & Med. Chem.*, 14, 5370-5383, 2006. All of these patents and/or patent applications and literature disclosures are incorporated herein by reference in their entirety for all purposes.

Cancer is a major public health problem in India, the U.S. and many other parts of the world. Currently, 1 in 4 deaths in India is due to cancer. Lung cancer is the leading cause of cancer deaths worldwide because of its high incidence and mortality, with 5-year survival estimates of ~10% for non-small cell lung cancer (NSCLC). It has been reported that further investigations on the mechanisms of tumorigenesis and chemoresistance of lung cancer are needed to improve the survival rate (Jemal A, et al., *Cancer Statistics, CA Cancer. J. Clin.*, 56, 106-130, 2006). There are four major types of NSCLC, namely, adenocarcinoma, squamous cell carcinoma, bronchioalveolar carcinoma, and large cell carcinoma. Adenocarcinoma and squamous cell carcinoma are the most common types of NSCLC based on cellular morphology (Travis et al., *Lung Cancer Principles and Practice*, Lippincott-Raven, New York, 361-395, 1996). Adenocarcinomas are characterized by a more peripheral location in the lung and often have a mutation in the K-ras oncogene (Gazdar et al., *Anticancer Res.*, 14, 261-267, 1994). Squamous cell carcinomas are typically more centrally located and frequently carry p53 gene mutations (Niklinska et al., *Folia Histochem. Cytobiol.*, 39, 147-148, 2001).

The majority of NSCLCs are characterized by the presence of the ras mutation thereby rendering the patient relatively insensitive to treatment by known kinase inhibitors. As a result, current treatments of lung cancer are generally limited to cytotoxic drugs, surgery, and radiation therapy. There is a need for treatments which have fewer side effects and more specifically target the cancer cells, are less invasive, and improve the prognosis of patients.

The identification of lung tumor-initiating cells and associated markers may be useful for optimization of therapeutic approaches and for predictive and prognostic information in lung cancer patients. Accordingly, a need remains for new methods of predicting, evaluating and treating patients afflicted with lung cancer.

There still remains an unmet and dire need for small molecule modulators having specificity towards Stim1 and/or Orai1 in order to regulate and/or modulate activity of CRAC channels, particularly for the treatment of diseases and disorders associated with the CRAC.

SUMMARY OF THE INVENTION

The present invention relates to compounds of formula (I), methods for their preparation, pharmaceutical compositions containing them, and methods of treatment with them.

In particular, compounds of formula (I) and their pharmaceutically acceptable salts thereof are calcium release-activated calcium channel modulators useful in the treatment, prevention, inhibition and/or amelioration of diseases or disorders associated with calcium release-activated calcium channel.

In one aspect, the present invention relates to a compound of formula (I):

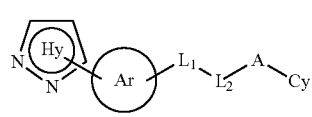
(I)

or a tautomer thereof, prodrug thereof, N-oxide thereof, pharmaceutically acceptable ester thereof or pharmaceutically acceptable salt thereof, wherein Ring Hy represents

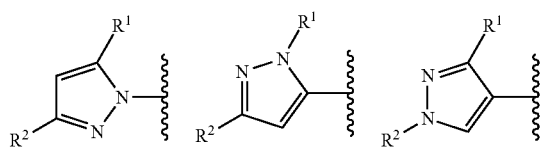

-continued

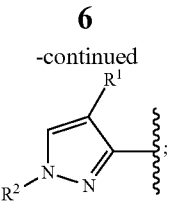

Ring Hy is optionally substituted with R''';

$R^1$ and $R^2$ are the same or different and are independently selected from $CH_3$, $CH_2F$, $CHF_2$, $CF_3$, substituted or unsubstituted $C_{(3-5)}$ cycloalkyl, $CH_2$—$OR^a$, $CH_2$—$NR^aR^b$, CN and COOH with the proviso that:

a) both $R^1$ and $R^2$ at the same time do not represent $CF_3$
b) both $R^1$ and $R^2$ at the same time do not represent $CH_3$,
c) when $R^1$ is $CF_3$ then $R^2$ is not $CH_3$ and
d) when $R^1$ is $CH_3$ then $R^2$ is not $CF_3$;

Ring Ar represents:

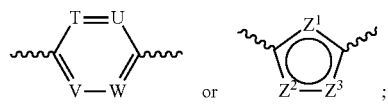

T, U, V and W are the same or different and are independently selected from $CR^a$ and N;

$Z^1$, $Z^2$ and $Z^3$ are the same or different and are independently selected from $CR^a$, $CR^aR^b$, O, S and —$NR^a$, with the proviso that at least one of $Z^1$, $Z^2$ and $Z^3$ represents O, S or —$NR^a$;

$L_1$ and $L_2$ together represent —NH—C(=X)—, —NH—S(=O)$_q$—, —C(=X)NH—, —NH—CR'R'' or —S(=O)$_q$NH—;

A is absent or selected from —(CR'R'')—, O, S(=O)$_q$, C(=X) and —$NR^a$;

each occurrence of R' and R'' are the same or different and are independently selected from hydrogen, hydroxy, cyano, halogen, —$OR^a$, —$COOR^a$, —$S(=O)_q$—$R^a$, —$NR^aR^b$, —C(=X)—$R^a$, substituted or unsubstituted $C_{(1-6)}$ alkyl group, substituted or unsubstituted $C_{(1-6)}$ alkenyl, substituted or unsubstituted $C_{(1-6)}$ alkynyl, and substituted or unsubstituted $C_{(3-5)}$cycloalkyl, or R' and R'' directly bound to a common atom, may be joined to form a substituted or unsubstituted saturated or unsaturated 3-6 member ring, which may optionally include one or more heteroatoms which may be same or different and are selected from O, $NR^a$ and S;

R''' is selected from hydrogen, hydroxy, cyano, halogen, —$OR^a$, —$COOR^a$, —$S(=O)_q$—$R^a$, —$NR^aR^b$, —C(=X)—$R^a$, substituted or unsubstituted $C_{(1-6)}$ alkyl group, substituted or unsubstituted $C_{(1-6)}$ alkenyl, substituted or unsubstituted $C_{(1-6)}$ alkynyl, and substituted or unsubstituted $C_{(3-5)}$cycloalkyl;

each occurrence of X is independently selected from O, S and —$NR^a$;

Cy is a bicyclic ring selected from substituted or unsubstituted cycloalkyl group, substituted or unsubstituted heterocyclyl, substituted or unsubstituted aryl, and substituted or unsubstituted heteroaryl;

each occurrence of $R^a$ and $R^b$ are the same or different and are independently selected from hydrogen, nitro, hydroxy, cyano, halogen, —$OR^c$, —$S(=O)_q$—$R^c$, —$NR^cR^d$, —C(=Y)—$R^c$, —$CR^cR^d$—C(=Y)—$R^c$, —$CR^cR^d$—Y—$CR^cR^d$—, —C(=Y)—$NR^cR^d$—, —$NRR^c$—C(=Y)—$NR^cR^d$—, —$S(=O)_q$—$NR^cR^d$—, —$NR^cR^d$—$S(=O)_q$—$NR^cR^d$—, —$NR^cR^d$—$NR^cR^d$—, substituted or unsubstituted alkyl, substituted or unsubstituted alkenyl, substituted or unsubstituted alkynyl, substituted or unsubstituted cycloalkyl, substituted or unsubstituted cycloalkylalkyl, substituted or unsubstituted cycloalkenyl, substituted or unsubstituted heterocyclyl, substituted or unsubstituted heterocyclylalkyl, substituted or unsubstituted aryl, substituted or unsubstituted arylalkyl, substituted or unsubstituted heteroaryl, and substituted or unsubstituted heteroarylalkyl, or when $R^a$ and $R^b$ are directly bound to the same atom, they may be joined to form a substituted or unsubstituted saturated or unsaturated 3-10 membered ring, which may optionally include one or more heteroatoms which may be same or different and are selected from O, $NR^c$ and S;

each occurrence of $R^c$ and $R^d$ may be same or different and are independently selected from hydrogen, nitro, hydroxy, cyano, halogen, substituted or unsubstituted alkyl, substituted or unsubstituted alkenyl, substituted or unsubstituted alkynyl, substituted or unsubstituted cycloalkyl, substituted or unsubstituted cycloalkylalkyl, substituted or unsubstituted cycloalkenyl, substituted or unsubstituted heterocyclic group, substituted or unsubstituted heterocyclylalkyl, or when two $R^c$ and/or $R^d$ substitutents are directly bound to the same atom, they may be joined to form a substituted or unsubstituted saturated or unsaturated 3-10 membered ring, which may optionally include one or more heteroatoms which are the same or different and are selected from O, NH and S;

each occurrence of Y is selected from O, S and —$NR^a$; and each occurrence of q independently represents an integer 0, 1 or 2;

with Proviso (e) that the compound of formula (I) is not: N-[4-[5-cyclopropyl-3-(trifluoromethyl)-1H-pyrazol-1-yl]phenyl]-1-methyl-3-(trifluoromethyl)-1H-Thieno[2,3-c]pyrazole-5-carboxamide or N-[4-[5-cyclopropyl-3-(trifluoromethyl)-1H-pyrazol-1-yl]phenyl]-Pyrazolo[1,5-a]pyrimidine-2-carboxamide.

In one preferred embodiment, $R^1$ is cyclopropyl.
In one preferred embodiment, $R^2$ is cyclopropyl.
According to one preferred embodiment, Hy is

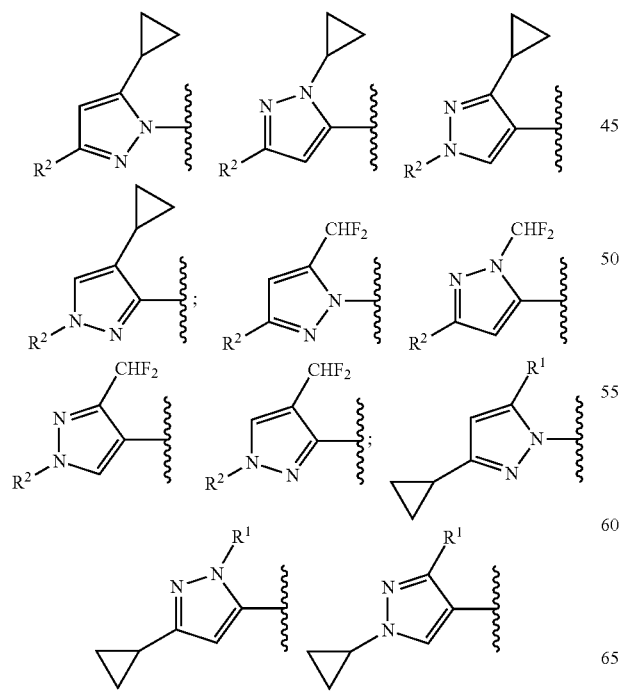

Further preferred is a compound of formula (I) wherein Hy is

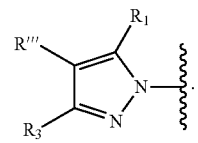

Further preferred is a compound of formula (I) wherein Hy is

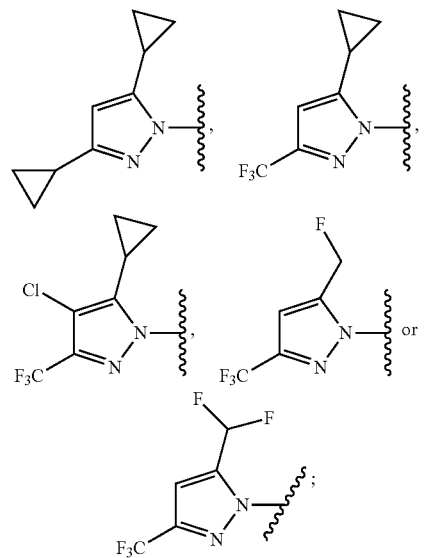

According to one preferred embodiment, Ar is

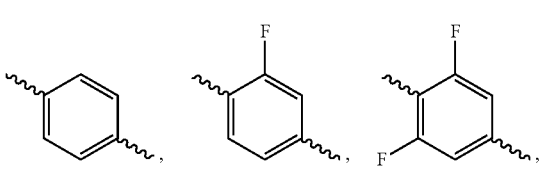

-continued

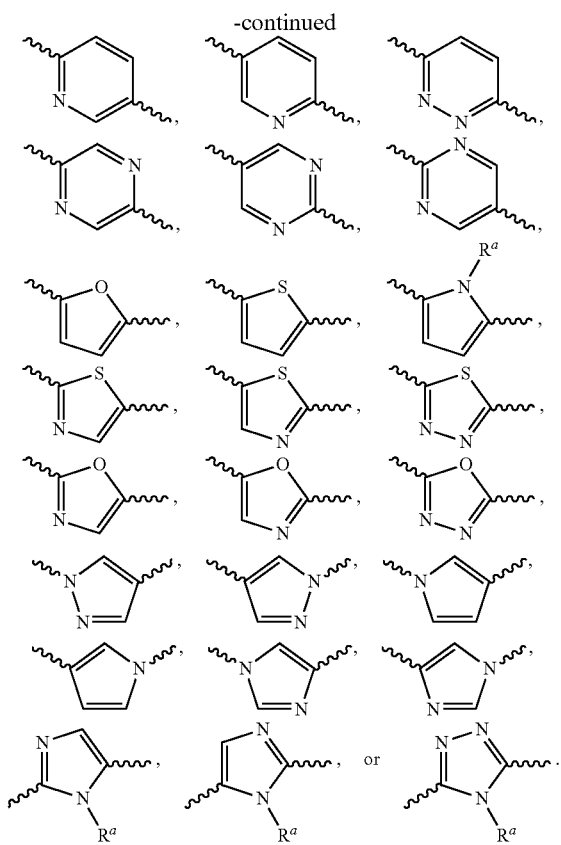

Further preferred is a compound of formula (I) wherein Ar is

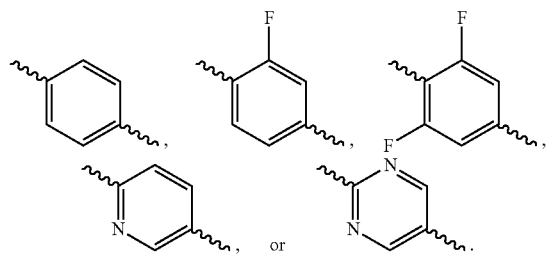

Further preferred is a compound of formula (I) wherein Ar is

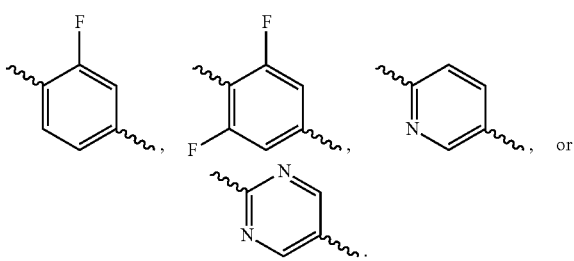

According to one preferred embodiment, $L_1$ and $L_2$ together represent —NH—C(=O)—, —NH—S(=O)$_q$—, —C(=O)NH— or —NH—CH$_2$—.

According to one preferred embodiment, A is absent or selected from —(CR'R")—, O, S(=O)$_q$, C(=X) and —NR$^a$. More preferably, A is —CH$_2$—, —CHMe- or —(CR'R")—, where R' and R" are joined to form a substituted or unsubstituted saturated or unsaturated 3-6 member ring, which may optionally include one or more heteroatoms which are the same or different and are selected from O, NR$^a$ (such as NH) and S;

Further preferred is a compound of formula (I) wherein A is

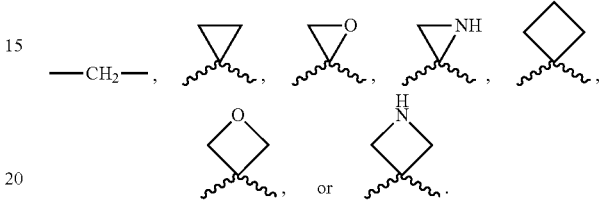

Further preferred is a compound of formula (I) wherein A is

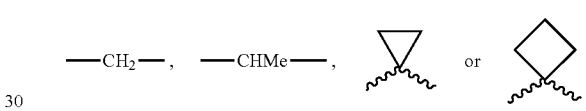

Further preferred is a compound of formula (I) wherein A is absent.

Further preferred is a compound of formula (I) wherein A is —CH$_2$—.

According to one preferred embodiment, Cy is

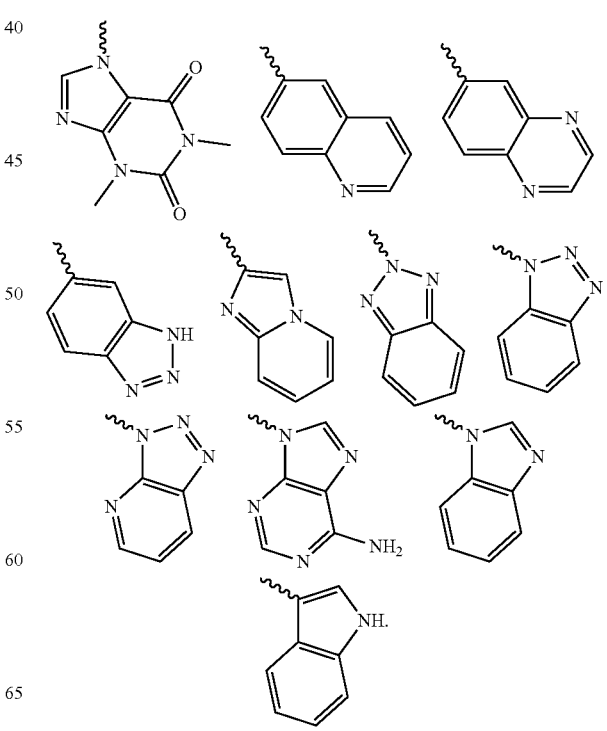

Further preferred is a compound of formula (I) wherein Cy is

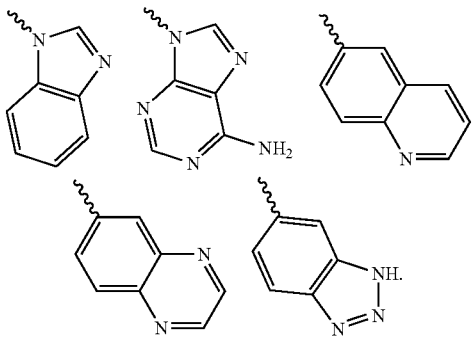

Further preferred is a compound of formula (I) wherein Cy is

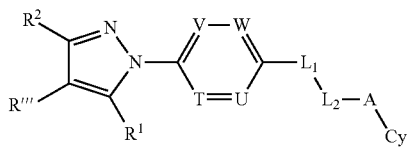

Yet another embodiment is a compound having the formula (IA):

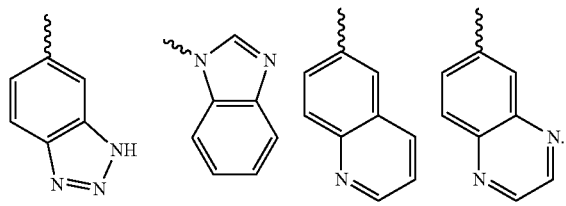

or a tautomer thereof, prodrug thereof, N-oxide thereof, pharmaceutically acceptable ester thereof, or pharmaceutically acceptable salt thereof, wherein the variables (e.g., R''', $R^1$, $R^2$, T, U, V, W, $L_1$, $L_2$, A and Cy) are defined as described above in relation to formula (I), with the proviso that the compound of formula (IA) is not any of the compounds in Proviso (a-e) as defined above.

Yet another embodiment is a compound having the formula (IA-I)

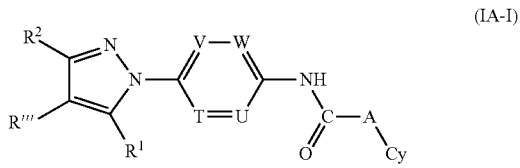

or a tautomer thereof, prodrug thereof, N-oxide thereof, pharmaceutically acceptable ester thereof, or pharmaceutically acceptable salt thereof, wherein the variables (e.g., R''', $R^1$, $R^2$, T, U, V, W, A and Cy) are defined as described above in relation to formula (I), with the proviso that the compound of formula (IA) is not any of the compounds in Proviso (a-e) defined above.

Further preferred is a compound of formula (IA-I)

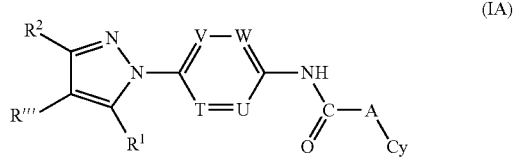

or a tautomer thereof, prodrug thereof, N-oxide thereof, pharmaceutically acceptable ester thereof, or pharmaceutically acceptable salt thereof, wherein
$R^1$ and $R^2$ are the same or different and are independently selected from $CH_2F$, $CHF_2$, $CF_3$ and cyclopropyl; with the proviso that both $R^1$ and $R^2$ at the same time do not represent $CF_3$.
R''' is hydrogen or halogen;
T, U, V, W are independently $CR^a$ or N;
$R^a$ is hydrogen or halogen;
A is absent or is selected from

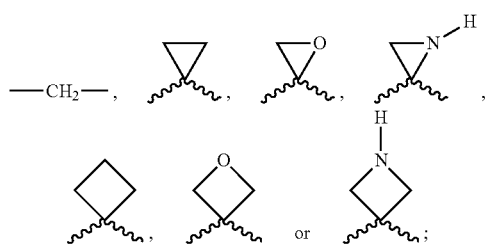

and
Cy is selected from bicyclic substituted or unsubstituted aryl or substituted or unsubstituted heteroaryl,
with the proviso that the compound of formula (IA) is not any of the compounds in Proviso (e) defined above.

Further preferred is a compound of formula (IA-I) wherein both $R^1$ and $R^2$ represent cyclopropyl.
Further preferred is a compound of formula (IA-I) wherein one of $R^1$ and $R^2$ is $CF_3$ and the other is cyclopropyl.
Further preferred is a compound of formula (IA-I) wherein $R^1$ is cyclopropyl and $R^2$ is $CF_3$.
Further preferred is a compound of formula (IA-I) wherein T, U, V, W are CH, CF or N.
Further preferred is a compound of formula (IA-I) wherein T is CF or N and each of U, V and W is CH.
Further preferred is a compound of formula (IA-I) wherein each of T and V is CF or N and each of U and W is CH.
Further preferred is a compound of formula (IA-I) wherein A is absent or is selected from

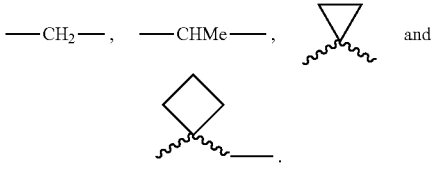

Further preferred is a compound of formula (IA-I) wherein Cy is selected from

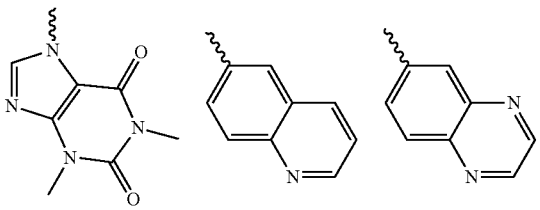

Yet another embodiment is a compound having the formula (IA-II)

$$(IA-II)$$

or a tautomer thereof, prodrug thereof, N-oxide thereof, pharmaceutically acceptable ester thereof, or pharmaceutically acceptable salt thereof, wherein $R^1$ and $R^2$ are the same or different and are independently selected from $CH_2F$, $CHF_2$, $CF_3$ and cyclopropyl; with the proviso that both R1 and $R^2$ at the same time do not represent $CF_3$.

R''' is hydrogen or halogen;

T, U, V, W are independently $CR^a$ or N;

$R^a$ is hydrogen or halogen;

A is absent or is selected from

—$CH_2$—, —CHMe—, △ or ◇;

and

Cy is selected from $C_{(8-13)}$ bicyclic substituted or unsubstituted heteroaryl, with the proviso that the compound of formula (IA) is not any of the compounds in Proviso (e) defined above.

Further preferred is a compound of formula (IA-II) wherein both $R^1$ and $R^2$ represent cyclopropyl.

Further preferred is a compound of formula (IA-II) wherein one of $R^1$ and $R^2$ is $CF_3$ and the other is cyclopropyl.

Further preferred is a compound of formula (IA-II) wherein $R^1$ is cyclopropyl and $R^2$ is $CF_3$.

Further preferred is a compound of formula (IA-II) wherein T, U, V, W are CH, CF or N.

Further preferred is a compound of formula (IA-II) wherein T is CF or N and each of U, V and W is CH.

Further preferred is a compound of formula (IA-II) wherein each of T and V is CF or N and each of U and W is CH.

Further preferred is a compound of formula (IA-II) wherein A is absent or —$CH_2$—.

In one embodiment, A is —$CH_2$—.

Further preferred is a compound of formula (IA-II) wherein Cy is selected from

Yet another embodiment is a compound having the formula (IA-III)

$$(IA-III)$$

or a tautomer, prodrug, N-oxide, pharmaceutically acceptable ester, or pharmaceutically acceptable salt thereof, wherein $R^1$ and $R^2$ are the same or different and are independently selected from $CH_2F$, $CHF_2$, $CF_3$, Cyclopropyl with the proviso that both $R^1$ and $R^2$ at the same time do not represent $CF_3$;

T and V are the same or different and are independently selected from CF and N;

Each of U and V is $CR^a$;

$L_1$ and $L_2$ together represent —NH—C(=X)—, —NH—S(=O)$_q$—, —C(=X)NH—, or —S(=O)$_q$NH— or —NH—CR'R"—;

A is absent or selected from —(CR'R")— and —$NR^a$;

each occurrence of R' and R" are the same or different and are independently selected from hydrogen or substituted or unsubstituted $C_{(1-6)}$ alkyl group or R' and R" may be joined to form a substituted or unsubstituted saturated or unsaturated 3-6 membered ring, which may optionally include one or more heteroatoms which may be same or different and are selected from O, $NR^a$ and S;

R''' is selected from the group consisting of hydrogen, or halogen each occurrence of X is independently selected from O, S and —$NR^a$;

Cy is a bicyclic ring selected from substituted or unsubstituted heterocyclyl, substituted or unsubstituted aryl, and substituted or unsubstituted heteroaryl.

each occurrence of $R^a$ and $R^b$ are the same or different and are independently selected from hydrogen, nitro, hydroxy, cyano, halogen, —OR$^c$, —S(=O)$_q$—R$^c$, —NR$^c$R$^d$, —C(=Y)—R$^c$, —CR$^c$R$^d$—C(=Y)—R$^c$, —CR$^c$R$^d$—Y—CR$^c$R$^d$—, —C(=Y)—NR$^c$R$^d$—, —NRR$^d$—C(=Y)—NR$^c$R$^d$—, —S(=O)$_q$—NR$^c$R$^d$—, —NR$^c$R$^d$—S(=O)$_q$—NR$^c$R$^d$—, —R$^c$R$^d$—NR$^c$R$^d$—, substituted or unsubstituted alkyl, substituted or unsubstituted alkenyl, substituted or unsubstituted alkynyl, substituted or unsubstituted cycloalkyl, substituted or unsubstituted cycloalkylalkyl, substituted or unsubstituted cycloalkenyl, substituted or unsubstituted heterocyclyl, substituted or unsubstituted heterocyclylalkyl, substituted or unsubstituted aryl, substituted or unsubstituted arylalkyl, substituted or unsubstituted heteroaryl, and substituted or unsubstituted heteroarylalkyl, or when R$^a$ and R$^b$ substitutent are directly bound to the same atom, they may be joined to form a substituted or unsubstituted saturated or unsaturated 3-10 member ring, which may optionally include one or more heteroatoms which may be same or different and are selected from O, NR$^c$ and S;

each occurrence of R$^c$ and R$^d$ may be same or different and are independently selected from the group consisting of hydrogen, nitro, hydroxy, cyano, halogen, substituted or unsubstituted alkyl, substituted or unsubstituted alkenyl, substituted or unsubstituted alkynyl, substituted or unsubstituted cycloalkyl, substituted or unsubstituted cycloalkylalkyl, substituted or unsubstituted cycloalkenyl, substituted or unsubstituted heterocyclic group, substituted or unsubstituted heterocyclylalkyl, or when two R$^c$ and/or R$^d$ substitutents are directly bound to the same atom, they may be joined to form a substituted or unsubstituted saturated or unsaturated 3-10 member ring, which may optionally include one or more heteroatoms which are the same or different and are selected from O, NH and S;

each occurrence of Y is selected from O, S and —NR$^a$; and each occurrence of q independently represents 0, 1 or 2.

Further preferred is a compound of formula (IA-III) wherein both R$^1$ and R$^2$ represent cyclopropyl.

Further preferred is a compound of formula (IA-III) wherein one of R$^1$ and R$^2$ is CF$_3$ and the other is cyclopropyl.

Further preferred is a compound of formula (IA-III) wherein one of R$^1$ and R$^2$ is CF$_3$ and the other is CH$_2$F, CHF$_2$.

Further preferred is a compound of formula (IA-III) wherein R$^1$ is cyclopropyl and R$^2$ is CF$_3$.

Further preferred is a compound of formula (IA-III) wherein T is CF or N.

Further preferred is a compound of formula (IA-III) wherein U, V, W are CH, CF or N.

Further preferred is a compound of formula (IA-III) wherein L$_1$ and L$_2$ together represent —NH—C(=O)—, C(=O)NH— or —NH—CH$_2$—;

Further preferred is a compound of formula (IA-III) wherein A is absent, —NH— or —CH$_2$—.

Further preferred is a compound of formula (IA-III) wherein Cy is selected from

Yet another embodiment is a compound having the formula (IA-IV)

(IA-IV)

or a tautomer, prodrug, N-oxide, pharmaceutically acceptable ester, or pharmaceutically acceptable salt thereof,
wherein
R$^1$ and R$^2$ are the same or different and are independently selected from CH$_2$F, CHF$_2$, CF$_3$, Cyclopropyl with the proviso that both R$^1$ and R$^2$ at the same time do not represent CF$_3$;

T and V are the same or different and are independently selected from CH, CF and N;

Each of U and V is CR$^a$;

L$_1$ and L$_2$ together represent —NH—C(=X)—, —NH—S(=O)$_q$—, —C(=X)NH—, or —S(=O)$_q$NH— or —NH—CR'R"—;

A is selected from —(CR'R")— and —NR$^a$;

each occurrence of R' and R" are the same or different and are independently selected from hydrogen or substituted or unsubstituted C$_{(1-6)}$ alkyl group or R' and R" may be joined to form a substituted or unsubstituted saturated or unsaturated 3-6 membered ring, which may optionally include one or more heteroatoms which may be same or different and are selected from O, NR$^a$ and S;

R''' is selected from the group consisting of hydrogen, or halogen each occurrence of X is independently selected from O, S and —NR$^a$;

Cy is a bicyclic substituted or unsubstituted heteroaryl.

each occurrence of R$^a$ and R$^b$ are the same or different and are independently selected from hydrogen, nitro, hydroxy, cyano, halogen, —OR$^c$, —S(=O)$_q$—R$^c$, —NR$^c$R$^d$, —C(=Y)—R$^c$, —CR$^c$R$^d$—C(=Y)—R$^c$, —CR$^c$R$^d$—Y—CR$^c$R$^d$—, —C(=Y)—NR$^c$R$^d$—, —NRR$^d$—C(=Y)—NR$^c$R$^d$—, —S(=O)$_q$—NR$^c$R$^d$—, —NR$^c$R$^d$—S(=O)$_q$—NR$^c$R$^d$—, —NR$^c$R$^d$—NR$^c$R$^d$—, substituted or unsubstituted alkyl, substituted or unsubstituted alkenyl, substituted or unsubstituted alkynyl, substituted or unsubstituted cycloalkyl, substituted or unsubstituted cycloalkylalkyl, substituted or unsubstituted cycloalkenyl, substituted or unsubstituted heterocyclyl, substituted or unsubstituted heterocyclylalkyl, substituted or unsubstituted aryl, substituted or unsubstituted arylalkyl, substituted or unsubstituted heteroaryl, and substituted or unsubstituted heteroarylalkyl, or when $R^a$ and $R^b$ substitutent are directly bound to the same atom, they may be joined to form a substituted or unsubstituted saturated or unsaturated 3-10 member ring, which may optionally include one or more heteroatoms which may be same or different and are selected from O, $NR^c$ and S;

each occurrence of $R^c$ and $R^d$ may be same or different and are independently selected from the group consisting of hydrogen, nitro, hydroxy, cyano, halogen, substituted or unsubstituted alkyl, substituted or unsubstituted alkenyl, substituted or unsubstituted alkynyl, substituted or unsubstituted cycloalkyl, substituted or unsubstituted cycloalkylalkyl, substituted or unsubstituted cycloalkenyl, substituted or unsubstituted heterocyclic group, substituted or unsubstituted heterocyclylalkyl, or when two $R^c$ and/or $R^d$ substitutents are directly bound to the same atom, they may be joined to form a substituted or unsubstituted saturated or unsaturated 3-10 member ring, which may optionally include one or more heteroatoms which are the same or different and are selected from O, NH and S;

each occurrence of Y is selected from O, S and $-NR^a$; and
each occurrence of q independently represents 0, 1 or 2.

Further preferred is a compound of formula (IA-IV) wherein both $R^1$ and $R^2$ represent cyclopropyl.

Further preferred is a compound of formula (IA-IV) wherein one of $R^1$ and $R^2$ is $CF_3$ and the other is cyclopropyl.

Further preferred is a compound of formula (IA-IV) wherein one of $R^1$ and $R^2$ is $CF_3$ and the other is $CH_2F$, $CHF_2$.

Further preferred is a compound of formula (IA-IV) wherein $R^1$ is cyclopropyl and $R^2$ is $CF_3$.

Further preferred is a compound of formula (IA-IV) wherein T is CH, CF or N.

Further preferred is a compound of formula (IA-IV) wherein U, V, W are CH, CF or N.

Further preferred is a compound of formula (IA-IV) wherein $L_1$ and $L_2$ together represent $-NH-C(=O)-$, $C(=O)NH-$ or $-NH-CH_2-$;

Further preferred is a compound of formula (IA-IV) wherein A is absent, $-NH-$ or $-CH_2-$.

Further preferred is a compound of formula (IA-IV) wherein Cy is selected from

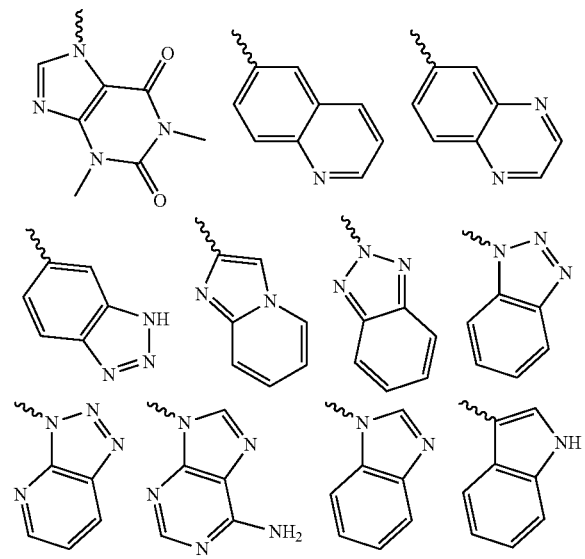

In yet another embodiment the present invention relates to methods for treating non-small cell lung cancer (NSCLC) with calcium release-activated calcium (CRAC) inhibitors, and methods for identifying therapeutics for treating and of diagnosing cancer. In certain embodiments, the CRAC inhibitor is a compound of Formula I, IA, IA-II, IA-III or IA-IV as in any of the embodiments described herein.

The present inventors have discovered that cancer cells which express ORAI (such as ORAI1, ORAI2, or ORAI3) or STIM (such as STIM1 or STIM2) are susceptible to treatment with calcium release-activated calcium (CRAC) inhibitors. These types of cancer cells are expressed in many patients suffering from non-small cell lung cancer (NSCLC).

One embodiment of the present invention is a method of treating a patient suffering from NSCLC by administering to the patient an effective amount of a CRAC inhibitor. In a preferred embodiment, at least some of the cancer cells express ORAI1, STIM1, or STIM2. The CRAC inhibitor may be used as a monotherapy or as an adjunctive therapy with one or more other methods of treating lung cancer (or NSCLC). In certain embodiments, the CRAC inhibitor is a compound of Formula I, IA, IA-II, IA-III or IA-IV as in any of the embodiments described herein.

Another embodiment is a method of treating a patient suffering from NSCLC by altering flow of calcium into at least some of the cancerous cells, preferably by increasing expression levels of a calcium release-activated calcium (CRAC) channel and/or a STIM protein in the plasma membrane of at least some of the cancerous cells.

Yet another embodiment is a method for identifying a candidate agent for treating NSCLC. The method includes (a) determining (i) whether a candidate agent modulates a calcium release-activated calcium (CRAC) channel, and/or (ii) whether a candidate agent modulates expression of Stim protein of a CRAC channel, or both; and (b) selecting the candidate agent based on its ability to modulate a CRAC channel and/or Stim protein of a CRAC channel In a preferred embodiment, the candidate agent can alter a flow of calcium into a cancerous cell. For instance, the candidate agent may selectively modulate a CRAC channel or STIM protein. Preferably, the candidate agent selectively inhibits a CRAC channel or STIM protein. For instance, the CRAC channel which is inhibited may be selected from CRACM1/Orai1, CRACM2/Orai2 and CRACM3/Orai3. In another embodiment, the candidate agent inhibits a STIM protein located on the endoplasmic veticular membrane of a cell. In particular embodiments, the STIM protein is selected from the STIM family of transmembrane proteins, such as STIM1 or STIM2. According to a preferred embodiment, the STIM protein is STIM1. In certain embodiments, the candidate agent is a compound of Formula I, IA, IA-II, IA-III or IA-IV as in any of the embodiments described herein.

Yet another embodiment is a pharmaceutical composition for treating NSCLC comprising (a) a candidate agent effective for treatment of NSCLC identified according to the method above, together with (b) a pharmaceutically acceptable carrier, diluent or excipient. In certain embodiments, the candidate agent is a compound of Formula I, IA, IA-II, IA-III or IA-IV, as in any of the embodiments described herein.

Yet another embodiment is a method of treating a patient suffering from NSCLC by administering to the patient (a) an effective amount of a candidate agent identified according to the method above, or (b) one or more pharmaceutical compositions comprising (i) a candidate agent effective for treatment of NSCLC identified according to the method above, together with (b) a pharmaceutically acceptable carrier, diluent or excipient, where the total amount of candidate agent provided by the pharmaceutical compositions provide a therapeutic effective amount of the candidate agent. In certain embodiments, the candidate agent is a compound of Formula I, IA, IA-II, IA-III or IA-IV as in any of the embodiments described herein.

Yet another embodiment is a method for determining whether a human is predisposed to lung cancer or suffering from lung cancer by detecting the level of a calcium release-activated calcium (CRAC) channel and/or a STIM protein in lung cells (such as cancerous cells). In one embodiment, the method includes detection of an elevated level of an Orai and/or STIM protein. For example, the method can include detecting increased levels of a STIM protein in a cancerous cell. For example, the STIM protein to be detected is a member of the STIM family of transmembrane proteins, such as STIM1 or STIM2. In one embodiment, the STIM protein to be detected is STIM1.

Representative compounds of the present invention include those specified below and in Table 1 and pharmaceutically acceptable salts thereof. The present invention should not be construed to be limited to them.

1. N-[4-(3,5-dicyclopropyl-1H-pyrazol-1-yl)phenyl]-1H-benzo[d]imidazole-6-carboxamide
2. N-[4-(3,5-dicyclopropyl-1H-pyrazol-1-yl)phenyl]-1H-benzo[d][1,2,3]triazole-6-carboxamide
3. N-[4-(3,5-dicyclopropyl-1H-pyrazol-1-yl)phenyl]quinoline-6-carboxamide hydrochloride
4. N-[4-(3,5-dicyclopropyl-1H-pyrazol-1-yl)phenyl]quinoxaline-6-carboxamide
5. 2-(1H-benzo[d]imidazol-1-yl)-N-[4-(3,5-dicyclopropyl-1H-pyrazol-1-yl)phenyl]acetamide
6. 2-(1H-benzo[d][1,2,3]triazol-1-yl)-N-[4-(3,5-dicyclopropyl-1H-pyrazol-1-yl)phenyl]acetamide
7. N-[4-(3,5-dicyclopropyl-1H-pyrazol-1-yl)phenyl]-2-(1H-indol-3-yl)acetamide
8. N-[4-(3,5-dicyclopropyl-1H-pyrazol-1-yl)phenyl]-2-(imidazo[1,2-a]pyridin-2-yl)acetamide hydrochloride
9. N-[4-(3,5-dicyclopropyl-1H-pyrazol-1-yl)phenyl]-2-(quinolin-6-yl)acetamide:
10. N-[4-(3,5-dicyclopropyl-1H-pyrazol-1-yl)phenyl]-2-(quinolin-6-yl)acetamide hydrochloride
11. 2-(1H-benzo[d][1,2,3]triazol-1-yl)-N-(4-(3,5-dicyclopropyl-1H-pyrazol-1-yl)-3-fluorophenyl)acetamide
12. N-[4-(3,5-dicyclopropyl-1H-pyrazol-1-yl)-3-fluorophenyl]-2-(quinolin-6-yl)acetamide hydrochloride
13. N-[6-(3,5-dicyclopropyl-1H-pyrazol-1-yl)pyridin-3-yl]quinoline-6-carboxamide dihydrochloride
14. N-[6-(3,5-dicyclopropyl-1H-pyrazol-1-yl)pyridin-3-yl]quinoxaline-6-carboxamide
15. 2-(1H-benzo[d][1,2,3]triazol-1-yl)-N-[6-(3,5-dicyclopropyl-1H-pyrazol-1-yl)pyridin-3-yl]acetamide
16. N-[6-(3,5-dicyclopropyl-1H-pyrazol-1-yl)pyridin-3-yl]-2-(quinolin-6-yl)acetamidedihydrochloride
17. N-{4-[5-cyclopropyl-3-(trifluoromethyl)-1H-pyrazol-1-yl]phenyl}quinoline-6-carboxamide hydrochloride
18. N-{4-[5-cyclopropyl-3-(trifluoromethyl)-1H-pyrazol-1-yl]phenyl}quinoxaline-6-carboxamide
19. 2-(1H-benzo[d]imidazol-1-yl)-N-{4-[5-cyclopropyl-3-(trifluoromethyl)-1H-pyrazol-1-yl]phenyl}acetamide
20. 2-(1H-benzo[d][1,2,3]triazol-1-yl)-N-{4-[5-cyclopropyl-3-(trifluoromethyl)-1H-pyrazol-1-yl]phenyl}acetamide
21. 2-(2H-benzo[d][1,2,3]triazol-2-yl)-N-{4-[5-cyclopropyl-3-(trifluoromethyl)-1H-pyrazol-1-yl]phenyl}acetamide
22. 2-(3H-[1,2,3]triazolo[4,5-b]pyridin-3-yl)-N-{4-[5-cyclopropyl-3-(trifluoromethyl)-1H-pyrazol-1-yl]phenyl}acetamide
23. (S)-2-(3H-[1,2,3]triazolo[4,5-b]pyridin-3-yl)-N-{4-[5-cyclopropyl-3-(trifluoromethyl)-1H-pyrazol-1-yl]phenyl}propanamide
24. 2-(6-amino-9H-purin-9-yl)-N-{4-[5-cyclopropyl-3-(trifluoromethyl)-1H-pyrazol-1-yl]phenyl}acetamide
25. N-(4-(5-cyclopropyl-3-(trifluoromethyl)-1H-pyrazol-1-yl)phenyl)-2-(1,3-dimethyl-2,6-dioxo-2,3-dihydro-1H-purin-7(6H)-yl)acetamide
26. N-{4-[5-cyclopropyl-3-(trifluoromethyl)-1H-pyrazol-1-yl]phenyl}-2-(imidazo[1,2-a]pyridin-2-yl)acetamide hydrochloride
27. N-{4-[5-cyclopropyl-3-(trifluoromethyl)-1H-pyrazol-1-yl]phenyl}-2-(quinolin-6-yl)acetamide hydrochloride
28. N-{4-[5-cyclopropyl-3-(trifluoromethyl)-1H-pyrazol-1-yl]phenyl}-2-(quinolin-6-yl)propanamide hydrochloride
29. N-{4-[5-cyclopropyl-3-(trifluoromethyl)-1H-pyrazol-1-yl]-3-fluorophenyl}-1H-benzo[d][1,2,3]triazole-6-carboxamide
30. 2-(1H-benzo[d][1,2,3]triazol-1-yl)-N-{4-[5-cyclopropyl-3-(trifluoromethyl)-1H-pyrazol-1-yl]-3-fluorophenyl}acetamide
31. N-{6-[5-cyclopropyl-3-(trifluoromethyl)-1H-pyrazol-1-yl]pyridin-3-yl}-1H-benzo[d][1,2,3]triazole-5-carboxamide
32. 2-(1H-benzo[d][1,2,3]triazol-1-yl)-N-{6-[5-cyclopropyl-3-(trifluoromethyl)-1H-pyrazol-1-yl]pyridin-3-yl}acetamide
33. 2-(2H-benzo[d][1,2,3]triazol-2-yl)-N-{6-[5-cyclopropyl-3-(trifluoromethyl)-1H-pyrazol-1-yl]pyridin-3-yl}acetamide
34. N-{6-[5-cyclopropyl-3-(trifluoromethyl)-1H-pyrazol-1-yl]pyridin-3-yl}-2-(quinolin-6-yl)acetamide hydrochloride
35. 2-(1H-benzo[d][1,2,3]triazol-1-yl)-N-{6-[4-chloro-5-cyclopropyl-3-(trifluoromethyl)-1H-pyrazol-1-yl]pyridin-3-yl}acetamide
36. 4-[5-cyclopropyl-3-(trifluoromethyl)-1H-pyrazol-1-yl]-3-fluoro-N-(quinolin-6-ylmethyl)benzamide hydrochloride
37. 1-[4-(3,5-dicyclopropyl-1H-pyrazol-1-yl)phenyl]-3-(quinolin-6-yl)urea:

TABLE 1

1

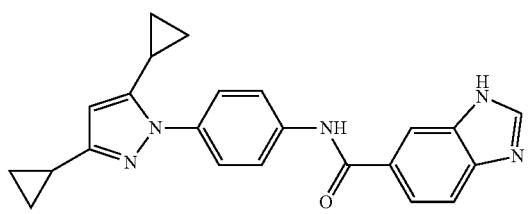 [SMILES: O=C(Nc1ccc(-n2nc(C3CC3)cc2C2CC2)cc1)c1ccc2nc[nH]c2c1]

TABLE 1-continued
2 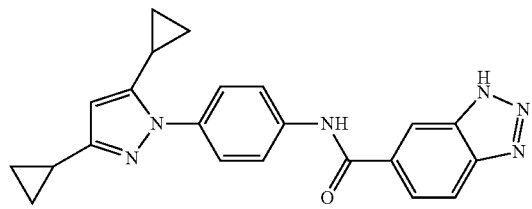 [SMILES: O=C(Nc1ccc(-n2nc(C3CC3)cc2C2CC2)cc1)c1ccc2nn[nH]c2c1]
3 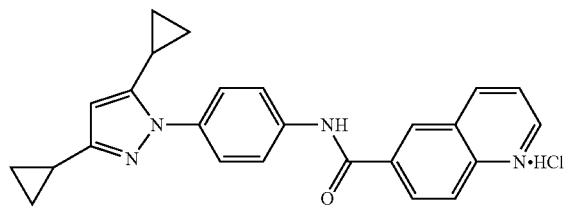
4 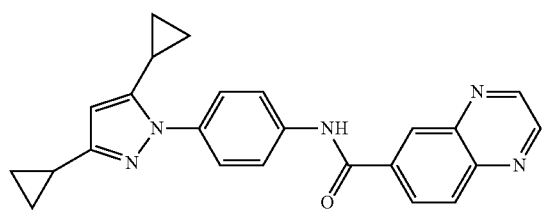 [SMILES: O=C(Nc1ccc(-n2nc(C3CC3)cc2C2CC2)cc1)c1ccc2nccnc2c1]
5 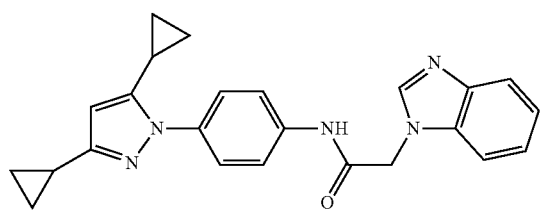 [SMILES: O=C(Cn1cnc2ccccc21)Nc1ccc(-n2nc(C3CC3)cc2C2CC2)cc1]
6 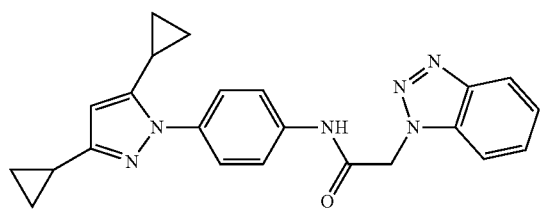
7 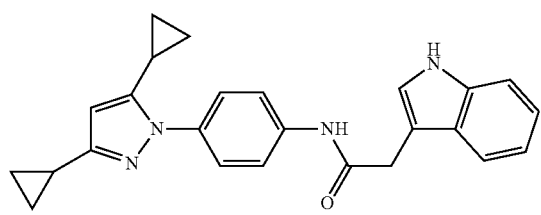 [SMILES: O=C(Cc1c[nH]c2ccccc12)Nc1ccc(-n2nc(C3CC3)cc2C2CC2)cc1]
8 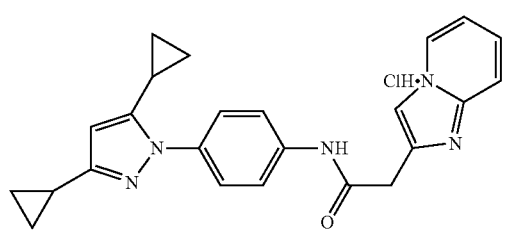

TABLE 1-continued
| 9 | 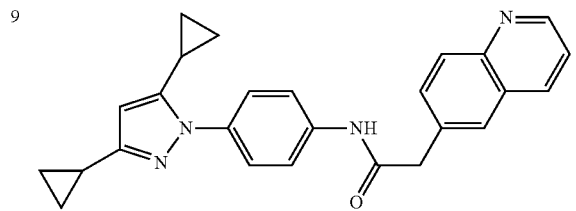 |
| --- | --- |
| 10 | 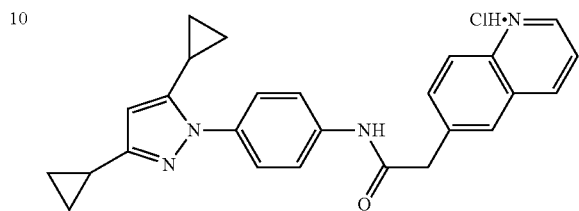 |
| 11 | 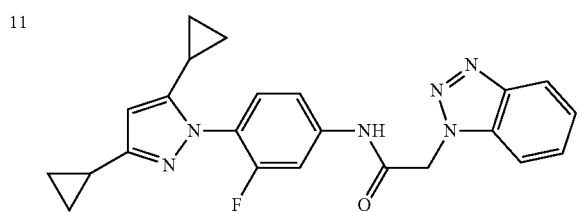 |
| 12 | 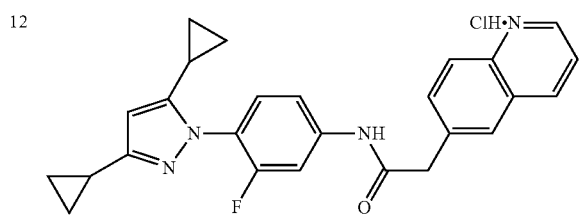 |
| 13 | 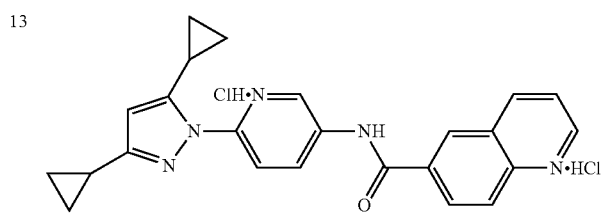 |
| 14 | 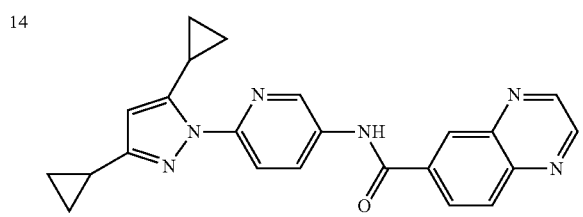 |
| 15 | 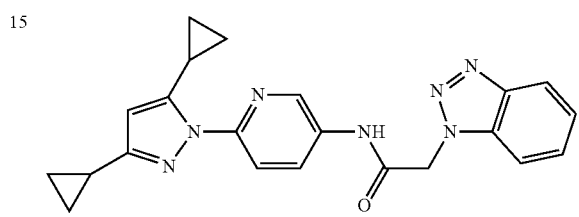 |

TABLE 1-continued

| | |
|---|---|
| 16 | [structure] |
| 17 | [structure] |
| 18 | [structure] |
| 19 | [structure] |
| 20 | [structure] |
| 21 | [structure] |
| 22 | [structure] |

TABLE 1-continued
| | |
|---|---|
| 23 | 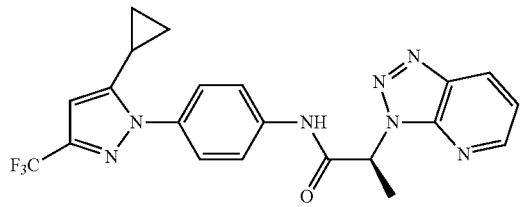 [SMILES: C[C@@H](C(=O)Nc1ccc(-n2nc(C(F)(F)F)cc2C2CC2)cc1)n1nnc2cccnc21] |
| 24 | 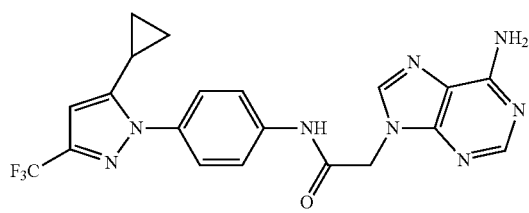 [SMILES: Nc1ncnc2c1ncn2CC(=O)Nc1ccc(-n2nc(C(F)(F)F)cc2C2CC2)cc1] |
| 25 | 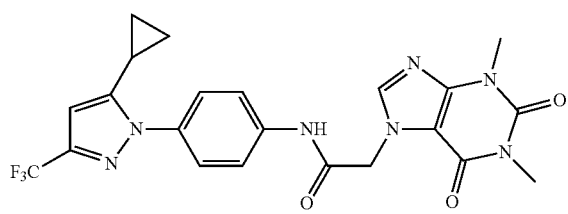 [SMILES: Cn1c(=O)c2c(ncn2CC(=O)Nc2ccc(-n3nc(C(F)(F)F)cc3C3CC3)cc2)n(C)c1=O] |
| 26 | 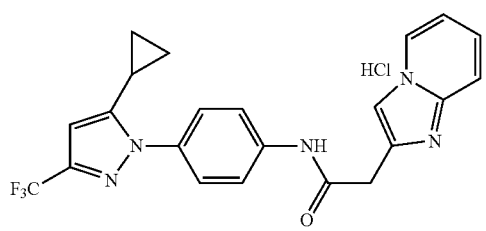 [SMILES: O=C(Cc1cn2ccccc2n1)Nc1ccc(-n2nc(C(F)(F)F)cc2C2CC2)cc1 ; Cl] |
| 27 | 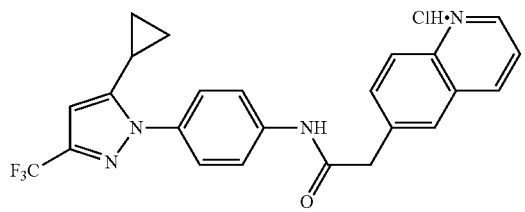 |
| 28 | 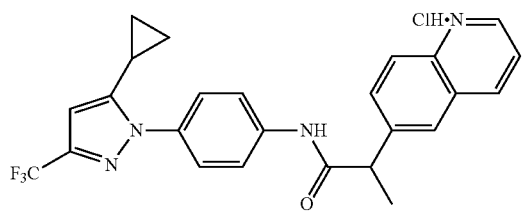 |
| 29 | 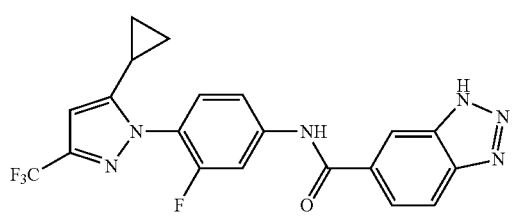 [SMILES: O=C(Nc1ccc(-n2nc(C(F)(F)F)cc2C2CC2)c(F)c1)c1ccc2nn[nH]c2c1] |

TABLE 1-continued
| 30 | 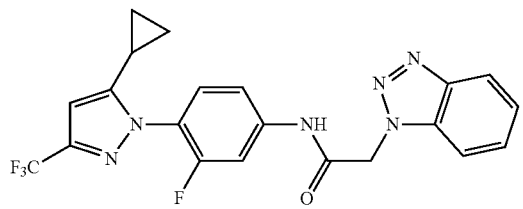 [SMILES: O=C(Cn1nnc2ccccc21)Nc1ccc(-n2nc(C(F)(F)F)cc2C2CC2)c(F)c1] |
| --- | --- |
| 31 | 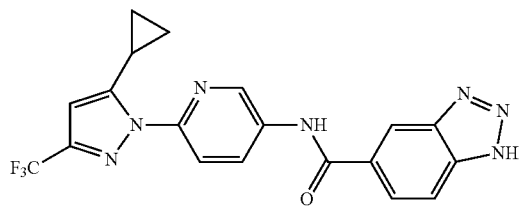 [SMILES: O=C(Nc1ccc(-n2nc(C(F)(F)F)cc2C2CC2)nc1)c1ccc2[nH]nnc2c1] |
| 32 | 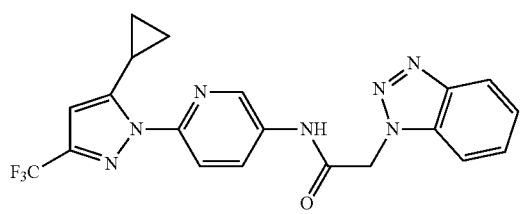 |
| 33 | 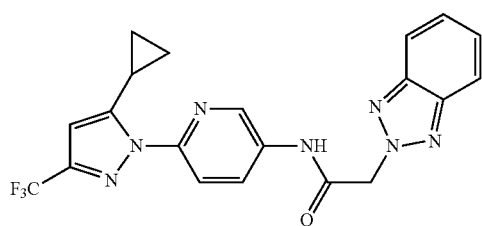 [SMILES: O=C(Cn1nc2ccccc2n1)Nc1ccc(-n2nc(C(F)(F)F)cc2C2CC2)nc1] |
| 34 | 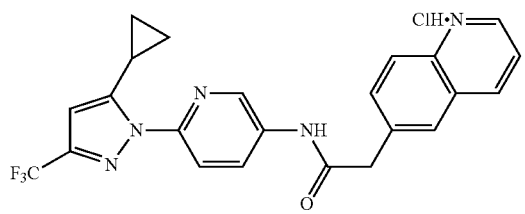 |
| 35 | 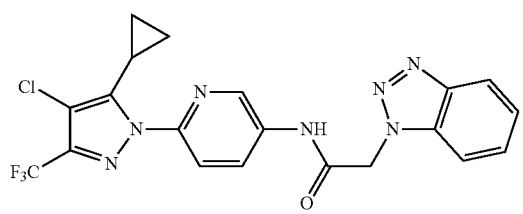 [SMILES: O=C(Cn1nnc2ccccc21)Nc1ccc(-n2nc(C(F)(F)F)c(Cl)c2C2CC2)nc1] |
| 36 | 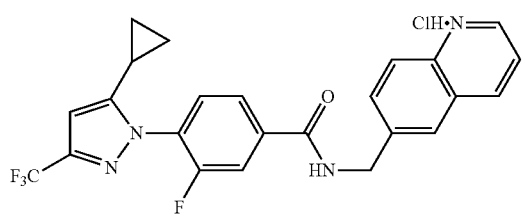 |

TABLE 1-continued

37 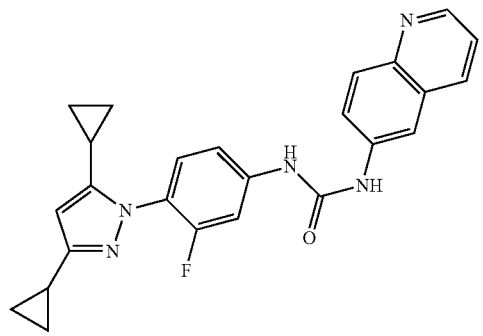 [SMILES: O=C(Nc1ccc(-n2nc(C3CC3)cc2C2CC2)c(F)c1)Nc1ccc2ncccc2c1]

The compounds of the present invention (e.g., compounds of formulas I, IA, IA-I, IA-II, IA-III and/or IA-IV including their pharmaceutically acceptable esters and salts) are useful for the treatment, prevention, inhibition, and/or amelioration of diseases and disorders associated with calcium release-activated calcium (CRAC) channel.

Another embodiment of the present invention is a method for treating a disease or disorder via modulation of CRAC channels by administering to a patient in need of such treatment an effective amount of a compound of the present invention (e.g., a compound of formula I, IA, IA-I, IA-II, IA-III and/or IA-IV as defined above).

Yet another embodiment of the present invention is a method for treating a disease or disorder via modulation of CRAC channels by administering to a patient in need of such treatment an effective amount of a compound of the present invention (e.g., a compound of formula I, IA, IA-I, IA-II, IA-III and/or IA-IV as defined above), in combination (simultaneously or sequentially) with at least one other anti-inflammatory agent.

Yet another embodiment of the present invention is a method for treating a disease or disorder via modulation of CRAC channels by administering to a patient in need of such treatment an effective amount of a compound of the present invention (e.g., a compound of formula I, IA, IA-I, IA-II, IA-III and/or IA-IV as defined above), in combination (simultaneously or sequentially) with at least one other anti-cancer agent.

The compounds of the present invention may inhibit store operated calcium entry, interrupt the assembly of SOCE units, alter the functional interactions of proteins that form store operated calcium channel complexes, and alter the functional interactions of STIM1 with Orai1. These compounds are SOC channel pore blockers, and are CRAC channel pore blockers.

The compounds described herein modulate intracellular calcium and are used in the treatment of diseases, disorders or conditions where modulation of intracellular calcium has a beneficial effect. In one embodiment, the compounds described herein inhibit store operated calcium entry. In one embodiment, the compounds of the present invention capable of modulating intracellular calcium levels interrupt the assembly of SOCE units. In another embodiment, the compounds of the present invention capable of modulating intracellular calcium levels alter the functional interactions of proteins that form store operated calcium channel complexes. In one embodiment, the compounds of the present invention capable of modulating intracellular calcium levels alter the functional interactions of STIM1 with Orai1. In other embodiments, the compounds of the present invention capable of modulating intracellular calcium levels are SOC channel pore blockers. In other embodiments, the compounds of the present invention capable of modulating intracellular calcium levels are CRAC channel pore blockers.

In one aspect, the compounds of the present invention capable of modulating intracellular calcium levels inhibit the electrophysiological current ($I_{SOC}$) directly associated with activated SOC channels. In one aspect, compounds capable of modulating intracellular calcium levels inhibit the electrophysiological current ($I_{CRAC}$) directly associated with activated CRAC channels.

The compounds of the present invention are useful in the treatment of diseases, conditions or disorders that benefit from modulation of intracellular calcium, including, but not limited to, an immune system-related disease (e.g., an autoimmune disease), a disease or disorder involving inflammation (e.g., asthma, chronic obstructive pulmonary disease, rheumatoid arthritis, inflammatory bowel disease, glomerulonephritis, neuroinflammatory diseases, multiple sclerosis, uveitis and disorders of the immune system), cancer or other proliferative disease, hepatic diseases or disorders, and renal diseases or disorders. In one embodiment, the compounds described herein are used as immunosuppressants to prevent (or inhibit) transplant graft rejections, allogeneic or xenogeneic transplantation rejection (organ, bone marrow, stem cells, other cells and tissues), and/or graft-versus-host disease. For instance, the compounds of the present invention can be used to prevent (or inhibit) transplant graft rejections result from tissue or organ transplants. The compounds of the present invention can also be used to prevent (or inhibit) graft-versus-host disease resulting from bone marrow or stem cell transplantation.

More particularly, the compounds of formula (I, IA, IA-I, IA-II, IA-III and/or IA-IV are useful in the treatment of a variety of inflammatory diseases including, but not limited to, inflammation, glomerulonephritis, uveitis, hepatic diseases or disorders, renal diseases or disorders, chronic obstructive pulmonary disease, rheumatoid arthritis, inflammatory bowel disease, vasculitis, dermatitis, osteoarthritis, inflammatory muscle disease, allergic rhinitis, vaginitis, interstitial cystitis, scleroderma, osteoporosis, eczema, allogeneic or xenogeneic transplantation, graft rejection, graft-versus-host disease, lupus erythematosus, type I diabetes, pulmonary fibrosis, dermatomyositis, thyroiditis, myasthenia gravis, autoimmune hemolytic anemia, cystic fibrosis, chronic relapsing hepatitis, primary biliary cirrhosis, allergic conjunctivitis, hepatitis and atopic dermatitis, asthma and Sjogren's syndrome The compounds described herein modulate an activity of, modulate an interaction of, or bind to, or interact with at least one portion of a protein in the store operated calcium channel complex. In one embodiment, the compounds described herein modulate an activity of, modulate an interaction of, or bind to, or interact with at least one portion of a protein in the calcium release activated calcium channel complex. In one embodiment, the compounds described herein reduce the level of functional store operated calcium channel complexes. In another embodiment, the compounds described herein reduce the level of activated store operated calcium channel complexes. In a further embodiment, the store operated calcium channel complexes are calcium release activated calcium channel complexes.

The compounds of the present invention which are capable of modulating intracellular calcium levels for treatment of a disease or disorder, when administered to a subject having a disease or disorder, effectively reduce, ameliorate or eliminate a symptom or manifestation of the disease, condition or disorder. In other embodiments, the compounds described herein are administered to a subject predisposed to a disease, condition or disorder that does not yet manifest a symptom of the disease, condition or disorder, and prevents or delays development of the symptoms. In further embodiments, the compound of the present invention has such effects alone or in combination with other agents, or functions to enhance a therapeutic effect of another agent.

Another embodiment of the present invention is a method for treating a proliferative disease via modulation of calcium by administering to a patient in need of such treatment an effective amount of at least one compound of formula I, IA, IA-I, IA-II, IA-III and/or IA-IV, as defined above.

Yet another embodiment of the present invention is a method for treating a proliferative disease via modulation of calcium by administering to a patient in need of such treatment an effective amount of at least one compound of formula I, IA, IA-I, IA-II, IA-III and/or IA-IV, as defined above, in combination (simultaneously or sequentially) with at least one other anti-cancer agent. In one embodiment, the proliferative disease is cancer.

More particularly, the compounds of formula I, IA, IA-I, IA-II, IA-III and/or IA-IV and pharmaceutically acceptable esters or salts thereof can be administered for the treatment, prevention and/or amelioration of diseases or disorders involving calcium, including but not limited to, cancer and other proliferative diseases or disorders.

The compounds of formula I, IA, IA-I, IA-II, IA-III and/or IA-IV are useful in the treatment of a variety of cancers, including, but not limited to, the following:

hematopoietic tumors of lymphoid lineage, including leukemia, acute lymphocytic leukemia, acute lymphoblastic leukemia, B-cell lymphoma, T-cell lymphoma, Hodgkin's lymphoma, non-Hodgkins lymphoma, hairy cell lymphoma and Burkett's lymphoma;

hematopoietic tumors of myeloid lineage, including acute and chronic myelogenous leukemias, myelodysplastic syndrome and promyelocytic leukemia;

carcinoma, including that of the bladder, breast, colon, kidney, liver, lung, including small cell lung cancer, esophagus, gall bladder, ovary, pancreas, stomach, cervix, thyroid, prostate, and skin, including squamous cell carcinoma;

tumors of mesenchymal origin, including fibrosarcoma and rhabdomyosarcoma;

tumors of the central and peripheral nervous system, including astrocytoma, neuroblastoma, glioma and schwannomas; and other tumors, including melanoma, seminoma, teratocarcinoma, osteosarcoma, xenoderoma pigmentosum, keratoctanthoma, thyroid follicular cancer and Kaposi's sarcoma.

Due to the key role of calcium in the regulation of cellular proliferation in general, calcium channel inhibitors could act as reversible cytostatic agents which may be useful in the treatment of any disease process which features abnormal cellular proliferation, e.g., benign prostatic hyperplasia, familial adenomatosis polyposis, neuro-fibromatosis, atherosclerosis, pulmonary fibrosis, arthritis, psoriasis, glomerulonephritis, restenosis following angioplasty or vascular surgery, hypertrophic scar formation, inflammatory bowel disease, transplantation rejection, endotoxic shock, and fungal infections.

The compounds of the present invention, as modulators of apoptosis, are useful in the treatment of cancer (including, but not limited to, those types mentioned herein above), viral infections (including, but not limited, to herpevirus, poxvirus, Epstein-Barr virus, Sindbis virus and adenovirus), prevention of AIDS development in HIV-infected individuals, autoimmune diseases (including, but not limited, to systemic lupus, erythematosus, autoimmune mediated glomerulonephritis, rheumatoid arthritis, psoriasis, inflammatory bowel disease, and autoimmune diabetes mellitus), neurodegenerative disorders (including, but not limited to, Alzheimer's disease, AIDS-related dementia, Parkinson's disease, amyotrophic lateral sclerosis, retinitis pigmentosa, spinal muscular atrophy and cerebellar degeneration), myelodysplastic syndromes, aplastic anemia, ischemic injury associated with myocardial infarctions, stroke and reperfusion injury, arrhythmia, atherosclerosis, toxin-induced or alcohol related liver diseases, hematological diseases (including but not limited to chronic anemia and aplastic anemia), degenerative diseases of the musculoskeletal system (including, but not limited to, osteoporosis and arthritis) aspirin-sensitive rhinosinusitis, cystic fibrosis, multiple sclerosis, kidney diseases and cancer pain.

The compounds of present invention can modulate the level of cellular RNA and DNA synthesis. These agents are therefore useful in the treatment of viral infections (including, but not limited to, HIV, human papilloma virus, herpesvirus, poxvirus, Epstein-Barr virus, Sindbis virus and adenovirus).

The compounds of the present invention are useful in the chemoprevention of cancer. Chemoprevention is defined as inhibiting the development of invasive cancer by either blocking the initiating mutagenic event or by blocking the progression of pre-malignant cells that have already suffered an insult or inhibiting tumor relapse. The compounds are also useful in inhibiting tumor angiogenesis and metastasis.

The compounds of the present invention are also useful in combination (administered together or sequentially) with known anti-cancer treatments such as radiation therapy or with cytostatic or cytotoxic or anticancer agents, such as for example, but not limited to, DNA interactive agents, such as cisplatin or doxorubicin; topoisomerase II inhibitors, such as etoposide; topoisomerase I inhibitors such as CPT-11 or topotecan; tubulin interacting agents, such as paclitaxel, docetaxel or the epothilones (for example, ixabepilone), either naturally occurring or synthetic; hormonal agents, such as tamoxifen; thymidilate synthase inhibitors, such as 5-fluorouracil; and anti-metabolites, such as methotrexate, other tyrosine kinase inhibitors such as Iressa and OSI-774; angiogenesis inhibitors; EGF inhibitors; VEGF inhibitors; CDK inhibitors; SRC inhibitors; c-Kit inhibitors; Her1/2 inhibitors and monoclonal antibodies directed against growth factor receptors such as erbitux (EGF) and herceptin (Her2) and other protein kinase modulators as well.

The invention further provides a pharmaceutical composition comprising one or more compounds of formula I, IA, IA-I, IA-II, IA-III and/or IA-IV and a pharmaceutically acceptable carrier.

Yet another embodiment of the invention is a dosage form comprising one or more compounds of the present invention, optionally with a pharmaceutically acceptable carrier. The dosage form can be, for example, a solid oral dosage form such as a tablet or capsule.

BRIEF DESCRIPTION OF THE FIGURES

In order that the invention may be readily understood and put into practical effect, preferred embodiments will now be described by way of example with reference to the accompanying figures wherein like reference numerals refer to like parts and wherein:

FIG. 1 is a picture of a gel showing the mRNA expression of Orai1 and STIM1 in A549 and NCI-H460 cell lines. Jurkat mRNA was used as a control.

FIG. 2 is a graph of the percentage of inhibition of thapsigargin induced calcium influx versus the logarithm of concentration of compound A.

FIG. 3 is a graph of the percentage of inhibition of NCI-H460 cell proliferation versus the logarithm of concentration of compound A.

FIG. 4 is a picture of a gel showing the effect of compound B on Orai and STIM expression in the NCI-H460 cell line.

FIG. 5 is a graph of the tumor volume in female Balb/c nude mice bearing a NCI-H460 non-small cell lung cancer xenograft, which is being treated with a vehicle, taxol, or compound A.

DETAIL DESCRIPTION OF THE INVENTION

Unless defined otherwise, all technical and scientific terms used herein have the same meaning as is commonly understood in the field to which the claimed subject matter belongs. In the event that there is a plurality of definitions for terms herein, those in this section prevail.

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

Definition of standard chemistry and molecular biology terms are found in reference works, including but not limited to, Carey and Sundberg "ADVANCED ORGANIC CHEMISTRY 4$^{th}$ edition" Vols. A (2000) and B (2001), Plenum Press, New York and "MOLECULAR BIOLOGY OF THE CELL 5$^{th}$ edition" (2007), Garland Science, New York. Unless otherwise indicated, conventional methods of mass spectroscopy, NMR, HPLC, protein chemistry, biochemistry, recombinant DNA techniques and pharmacology, are contemplated within the scope of the embodiments disclosed herein.

Unless specific definitions are provided, the nomenclature employed in connection with, and the laboratory procedures and techniques of, analytical chemistry, and medicinal and pharmaceutical chemistry described herein are those generally used. In some embodiments, standard techniques are used for chemical analyses, pharmaceutical preparation, formulation, and delivery, and treatment of patients. In other embodiments, standard techniques are used for recombinant DNA, oligonucleotide synthesis, and tissue culture and transformation (e.g., electroporation, lipofection). In finer embodiments, reactions and purification techniques are performed e.g., using kits of manufacturer's specifications or as described herein. The foregoing techniques and procedures are generally performed by conventional methods and as described in various general and more specific references that are cited and discussed throughout the present specification.

As used herein the following definitions shall apply unless otherwise indicated. Further many of the groups defined herein can be optionally substituted. The listing of substituents in the definition is exemplary and is not to be construed to limit the substituents defined elsewhere in the specification.

The term 'alkyl' refers to a straight or branched hydrocarbon chain radical consisting solely of carbon and hydrogen atoms, containing no unsaturation, having from one to eight carbon atoms, and which is attached to the rest of the molecule by a single bond, e.g., methyl, ethyl, n-propyl, 1-methylethyl(isopropyl), n-butyl, n-pentyl, and 1,1-dimethylethyl (t-butyl).

The term substituted or unsubstituted ($C_{1-6}$) alkyl refers to an alkyl group as defined above having up to 6 carbon atoms.

The term "alkenyl" refers to an aliphatic hydrocarbon group containing a carbon-carbon double bond and which may be a straight or branched or branched chain having about 2 to about 10 carbon atoms, e.g., ethenyl, 1-propenyl, 2-propenyl(allyl), iso-propenyl, 2-methyl-1-propenyl, 1-butenyl, and 2-butenyl.

The term substituted or unsubstituted ($C_{1-6}$)alkenyl refers to an alkenyl group as defined above having up to 6 carbon atoms.

The term "alkynyl" refers to a straight or branched chain hydrocarbyl radical having at least one carbon-carbon triple bond, and having in the range of about 2 up to 12 carbon atoms (with radicals having in the range of about 2 to 10 carbon atoms presently being preferred) e.g., ethynyl, propynyl, and butnyl.

The term substituted or unsubstituted ($C_{1-6}$) alkynyl refers to an alkynyl group as defined above having up to 6 carbon atoms.

The term "alkoxy" denotes an alkyl group as defined above attached via an oxygen linkage to the rest of the molecule. Representative examples of those groups are —$OCH_3$ and —$OC_2H_5$.

The term "cycloalkyl" denotes a non-aromatic mono or multicyclic ring system of about 3 to 12 carbon atoms such as cyclopropyl, cyclobutyl, cyclopentyl, and cyclohexyl. Non-limiting examples of multicyclic cycloalkyl groups include perhydronaphthyl, adamantly, norbornyl groups (bridged cyclic group), or spirobicyclic groups e.g. spiro(4,4)non-2-yl.

The term "cycloalkylalkyl" refers to a cyclic ring-containing radical containing in the range of about 3 up to 8 carbon atoms directly attached to an alkyl group which is then attached to the main structure at any carbon in the alkyl group that results in the creation of a stable structure such as cyclopropylmethyl, cyclobutylethyl, and cyclopentylethyl.

The term "cycloalkenyl" refers to a cyclic ring-containing radical containing in the range of about 3 up to 8 carbon atoms with at least one carbon-carbon double bond such as cyclopropenyl, cyclobutenyl, and cyclopentenyl.

The term "aryl" refers to an aromatic radical having in the range of 6 up to 20 carbon atoms such as phenyl, naphthyl, tetrahydronaphthyl, indanyl, and biphenyl.

The term "arylalkyl" refers to an aryl group as defined above directly bonded to an alkyl group as defined above, e.g., —CH$_2$C$_6$H$_5$, and —C$_2$H$_5$C$_6$H$_5$.

The term "heterocyclic ring" refers to a non-aromatic 3 to 15 member ring radical which, consists of carbon atoms and at least one heteroatom selected from the group consisting of nitrogen, phosphorus, oxygen and sulfur. For purposes of this invention, the heterocyclic ring radical may be a mono-, bi-, tri- or tetracyclic ring system, which may include fused, bridged or spiro ring systems, and the nitrogen, phosphorus, carbon, oxygen or sulfur atoms in the heterocyclic ring radical may be optionally oxidized to various oxidation states. In addition, the nitrogen atom may be optionally quaternized. The heterocyclic ring radical may be attached to the main structure at any heteroatom or carbon atom that results in the creation of a stable structure.

The term "heteroaryl" refers to an optionally substituted 5-14 member aromatic ring having one or more heteroatoms selected from N, O, and S as ring atoms. The heteroaryl may be a mono-, bi- or tricyclic ring system. Examples of such heteroaryl ring radicals includes but are not limited to oxazolyl, thiazolyl imidazolyl, pyrrolyl, furanyl, pyridinyl, pyrimidinyl, pyrazinyl, benzofuranyl, indolyl, benzothiazolyl, benzoxazolyl, carbazolyl, quinolyl and isoquinolyl. The heteroaryl ring radical may be attached to the main structure at any heteroatom or carbon atom that results in the creation of a stable structure.

Examples of such "heterocyclic ring" or "heteroaryl" radicals include, but are not limited to, azetidinyl, acridinyl, benzodioxolyl, benzodioxanyl, benzofuryl, carbazolyl, cinnolinyl, dioxolanyl, indolizinyl, naphthyridinyl, perhydroazepinyl, phenazinyl, phenothiazinyl, phenoxazinyl, phthalazinyl, pyridyl, pteridinyl, purinyl, quinazolinyl, quinoxalinyl, quinolinyl, isoquinolinyl, tetrazoyl, imidazolyl, tetrahydroisouinolyl, piperidinyl, piperazinyl, 2-oxopiperazinyl, 2-oxopiperidinyl, 2-oxopyrrolidinyl, 2-oxoazepinyl, azepinyl, pyrrolyl, 4-piperidonyl, pyrrolidinyl, pyrazinyl, pyrimidinyl, pyridazinyl, oxazolyl, oxazolinyl, oxasolidinyl, triazolyl, indanyl, isoxazolyl, isoxasolidinyl, morpholinyl, thiazolyl, thiazolinyl, thiazolidinyl, isothiazolyl, quinuclidinyl, isothiazolidinyl, indolyl, isoindolyl, indolinyl, isoindolinyl, octahydroindolyl, octahydroisoindolyl, quinolyl, isoquinolyl, decahydroisoquinolyl, benzimidazolyl, thiadiazolyl, benzopyranyl, benzothiazolyl, benzooxazolyl, furyl, tetrahydrofurtyl, tetrahydropyranyl, thienyl, benzothienyl, thiamorpholinyl, thiamorpholinyl sulfoxide thiamorpholinyl sulfone, dioxaphospholanyl, oxadiazolyl, chromanyl, isochromanyl and the like.

The term "heteroarylalkyl" refers to a heteroaryl ring radical as defined above directly bonded to an alkyl group. The heteroarylalkyl radical may be attached to the main structure at any carbon atom from the alkyl group that results in the creation of a stable structure.

The term "heterocyclylalkyl" refers to a heterocyclic ring radical as defined above directly bonded to an alkyl group. The heterocyclylalkyl radical may be attached to the main structure at carbon atom in the alkyl group that results in the creation of a stable structure.

The term "substituted" unless otherwise specified refers to substitution with any one or any combination of the following substituents: hydrogen, hydroxy, halogen, carboxyl, cyano, nitro, oxo (=O), thio(=S), substituted or unsubstituted alkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted cycloalkyl, substituted or unsubstituted cycloalkenyl, substituted or unsubstituted aryl, substituted or unsubstituted heteroaryl, substituted heterocyclylalkyl ring, substituted or unsubstituted heteroarylalkyl, substituted or unsubstituted heterocyclic ring, substituted or unsubstituted guanidine, —COOR$^x$, —C(O)R$^x$, —C(S)R$^x$, —C(O)NR$^x$R$^y$, —C(O)ONR$^x$R$^y$, —NR$^y$R$^z$, —NR$^x$CONR$^y$R$^z$, —N(R$^x$)SOR$^y$, —N(R$^x$)SO$_2$R$^y$, —(=N—N(R$^x$)R$^y$), —NR$^x$C(O)OR$^y$, —NR$^x$R$^y$, —NR$^x$C(O)R$^y$—, —NR$^x$C(S)R$^y$—NR$^x$C(S)NR$^y$R$^z$, —SONR$^x$R$^y$—, —SO$_2$NR$^x$R$^y$—, —OR$^x$, —OR$^x$C(O)NR$^y$R$^z$, —OR$^x$C(O) OR$^y$—, —OC(O)R$^x$, —OC(O)NR$^x$R$^y$, —R$^x$NR$^y$C(O)R$^z$, —R$^x$OR$^y$, —R$^x$C(O)OR$^y$, —R$^x$C(O)NR$^y$R$^z$, —R$^x$C(O)R$^x$, —R$^x$OC(O)R$^y$, —SR$^x$, —SOR$^x$, —SO$_2$R$^x$, and —ONO$_2$, wherein R$^x$, R$^y$ and R$^z$ in each of the above groups can be hydrogen atom, substituted or unsubstituted alkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted cycloalkyl, substituted or unsubstituted cycloalkenyl, substituted or unsubstituted amino, substituted or unsubstituted aryl, substituted or unsubstituted heteroaryl, substituted heterocyclylalkyl ring, substituted or unsubstituted heteroarylalkyl, substituted or unsubstituted heterocyclic ring, or any two of R$^x$, R$^y$ and R$^z$ may be joined to form a substituted or unsubstituted saturated or unsaturated 3-10 member ring, which may optionally include heteroatoms which may be same or different and are selected from O, NR$^X$ or S. The substituents in the aforementioned "substituted" groups cannot be further substituted. For example, when the substituent on "substituted alkyl" is "substituted aryl", the substituent on "substituted aryl" cannot be "substituted alkenyl". Substitution or the combination of substituents envisioned by this invention are preferably those resulting in the formation of a stable compound.

The term "halogen" or "halo" refers to radicals of fluorine, chlorine, bromine and iodine.

The term "protecting group" or "PG" refers to a substituent that is employed to block or protect a particular functionality. Other functional groups on the compound may remain reactive. For example, an "amino-protecting group" is a substituent attached to an amino group that blocks or protects the amino functionality in the compound. Suitable amino-protecting groups include, but are not limited to, acetyl, trifluoroacetyl, tert-butoxycarbonyl (BOC), benzyloxycarbonyl (CBz) and 9-fluorenylmethylenoxycarbonyl (Fmoc). Similarly, a "hydroxy-protecting group" refers to a substituent of a hydroxy group that blocks or protects the hydroxy functionality. Suitable hydroxy-protecting groups include, but are not limited to, acetyl and silyl. A "carboxy-protecting group" refers to a substituent of the carboxy group that blocks or protects the carboxy functionality. Suitable carboxy-protecting groups include, but are not limited to, —CH$_2$CH$_2$SO2Ph, cyanoethyl, 2-(trimethylsilyl)ethyl, 2-(trimethyl silyl) ethoxymethyl, 2-toluenesulfonyl)ethyl, 2-(p-nitrophenylsulfenyl)ethyl, 2-dipheny-1-phosphino)-ethyl and nitroethyl. For a general description of protecting groups and their use, see T. W. Greene, Protective Groups in Organic Synthesis, John Wiley & Sons, New York, 1991.

The term "stereoisomer" refers to compounds, which have identical chemical composition, but differ with regard to arrangement of the atoms and the groups in space. These include enantiomers, diastereomers, geometrical isomers, atropisomer or conformational isomers.

All the stereoisomers of compounds described herein are within the scope of this invention. Racemic mixtures are also encompassed within the scope of this invention. Therefore, single stereochemical isomers as well enantiomeric, diastereoisomeric and geometric (or conformational) mixtures of the present compounds fall within the scope of the invention.

The term "tautomers" refers to compounds, which are characterized by relatively easy interconversion of isomeric forms in equilibrium. These isomers are intended to be covered by this invention.

The term "prodrug" refers to compounds, which are an inactive precursor of a compound, converted into its active form in the body by normal metabolic processes.

The term "ester" refers to compounds, which are formed by reaction between an acid and an alcohol with elimination of water. An ester can be represented by the formula RCOOR', where R is the base compound and R' is the ester moiety (e.g., an ethyl group).

Additionally the instant invention also includes the compounds which differ only in the presence of one or more isotopically enriched atoms for example replacement of hydrogen with deuterium and the like.

Pharmaceutically acceptable salts forming part of this invention include salts derived from inorganic bases such as Li, Na, K, Ca, Mg, Fe, Cu, Zn, and Mn; salts of organic bases such as N,N'-diacetylethylenediamine, glucamine, triethylamine, choline, hydroxide, dicyclohexylamine, metformin, benzylamine, trialkylamine, and thiamine; chiral bases such as alkylphenylamine, glycinol, and phenyl glycinol, salts of natural amino acids such as glycine, alanine, valine, leucine, isoleucine, norleucine, tyrosine, cystine, cysteine, methionine, proline, hydroxy proline, histidine, ornithine, lysine, arginine, and serine; quaternary ammonium salts of the compounds of invention with alkyl halides or alkyl sulphates such as MeI and $(Me)_2SO_4$; non-natural amino acids such as D-isomers or substituted amino acids; guanidine or substituted guanidine wherein the substituents are selected from nitro, amino, alkyl, alkenyl, alkynyl, ammonium or substituted ammonium salts and aluminum salts. Salts may include acid addition salts where appropriate which are sulphates, nitrates, phosphates, perchlorates, borates, hydrohalides, acetates, tartrates, maleates, citrates, fumarates, succinates, palmoates, methanesulphonates, benzoates, salicylates, benzenesulfonates, ascorbates, glycerophosphates, and ketoglutarates.

The term "subject" or "patient" encompasses mammals and non-mammals. Examples of mammals include, but are not limited to, any member of the Mammalian class: humans, non-human primates such as chimpanzees, and other apes and monkey species; farm animals such as cattle, horses, sheep, goats, and swine; domestic animals such as rabbits, dogs, and cats; and laboratory animals including rodents, such as rats, mice and guinea pigs. Examples of non-mammals include, but are not limited to, birds, and fish. In one embodiment of the methods and compositions provided herein, the mammal is a human.

The terms "treat," "treating" or "treatment," as used herein, include alleviating, abating or ameliorating a disease, disorder or condition symptoms, preventing additional symptoms, ameliorating or preventing the underlying causes of symptoms, inhibiting the disease, disorder or condition, e.g., arresting the development of the disease, disorder or condition, relieving the disease, disorder or condition, causing regression of the disease, disorder or condition, relieving a condition caused by the disease, disorder or condition, or stopping the symptoms of the disease, disorder or condition either prophylactically and/or therapeutically.

As used herein, the term "target protein" refers to a protein or a portion of a protein capable of being bound by, or interacting with a compound described herein, such as a compound capable of modulating a STIM protein and/or an Orai protein. In certain embodiments, a target protein is a STIM protein. In other embodiments, a target protein is an Orai protein, and in yet other embodiments, the compound targets both STIM and Orai proteins.

The term "STIM protein" refers to any protein situated in the endoplasmic reticular or plasma membrane which activates an increase in rate of calcium flow into a cell by a CRAC channel. (STIM refers to a stromal interaction molecule.) As used herein, "STIM protein" includes but is not limited to, mammalian STIM-1, such as human and rodent (e.g., mouse) STIM-1, *Drosophila melanogaster* D-STIM, *C. elegans* C-STIM, *Anopheles gambiae* STIM and mammalian STIM-2, such as human and rodent (e.g., mouse) STIM-2. As described herein, such proteins have been identified as being involved in, participating in and/or providing for store-operated calcium entry or modulation thereof, cytoplasmic calcium buffering and/or modulation of calcium levels in or movement of calcium into, within or out of intracellular calcium stores (e.g., endoplasmic reticulum).

It will be appreciated by "activate" or "activation" it is meant the capacity of a STIM protein to up-regulate, stimulate, enhance or otherwise facilitate calcium flow into a cell by a CRAC channel. It is envisaged that cross-talk between the STIM protein and the CRAC channel may occur by either a direct or indirect molecular interaction. Suitably, the STIM protein is a transmembrane protein which is associated with, or in close proximity to, a CRAC channel.

It is known in the art that STIM1 is an essential component of CRAC channel activation. The present inventors have observed that STIM1 and STIM2 is expressed in certain NSCLC cell lines. Moreover, CRACM1/Orai 1 and CRACM3/Orai3 are excessively expressed in certain NSCLC cell lines. Although not wishing to be bound by any particular theory, CRAC and STIM proteins potentially contribute to activation of proliferative pathways in NSCLC cells in the following manner: (i) excessive dysregulation of STIM in NSCLC cells results in incorrect plasma membrane accumulation of STIM and (ii) at the plasma membrane, STIM activates CRAC (by either a direct or indirect interaction), which results in excessive calcium influx into the cell and promotion of transcription, proliferation and invasiveness in NSCLC cells. Hence, inhibition of the CRAC channel or the STIM pathway is an effective treatment for NSCLC.

As used herein, an "Orai protein" includes Orai1 (SEQ ID NO: 1 as described in WO 07/081,804), Orai2 (SEQ ID NO: 2 as described in WO 07/081,804), or Orai3 (SEQ ID NO: 3 as described in WO 07/081,804). Orai1 nucleic acid sequence corresponds to GenBank accession number NM-032790, Orai2 nucleic acid sequence corresponds to GenBank accession number BC069270 and Orai3 nucleic acid sequence corresponds to GenBank accession number NM-152288. As used herein, Orai refers to any one of the Orai genes, e.g., Orai1, Orai2, and Orai3 (see Table I of WO 07/081,804). As described herein, such proteins have been identified as being involved in, participating in and/or providing for store-operated calcium entry or modulation thereof, cytoplasmic calcium buffering and/or modulation of calcium levels in or movement of calcium into, within or out of intracellular calcium stores (e.g., endoplasmic reticulum). In alternative embodiments, an Orai protein may be labelled with a tag molecule, by way of example only, an enzyme fragment, a protein (e.g. c-myc or other tag protein or fragment thereof), an enzyme tag, a fluorescent tag, a fluorophore tag, a chromophore tag, a Raman-activated tag, a chemiluminescent tag, a quantum dot marker, an antibody, a radioactive tag, or combination thereof.

The term "fragment" or "derivative" when referring to a protein (e.g. STIM, Orai) means proteins or polypeptides which retain essentially the same biological function or activity in at least one assay as the native protein(s). For example, the fragment or derivative of the referenced protein preferably maintains at least about 50% of the activity of the native protein, at least 75%, or at least about 95% of the activity of the native protein, as determined, e.g., by a calcium influx assay.

As used herein, "amelioration" refers to an improvement in a disease or condition or at least a partial relief of symptoms associated with a disease or condition. As used herein, amelioration of the symptoms of a particular disease, disorder or condition by administration of a particular compound or pharmaceutical composition refers to any lessening of severity, delay in onset, slowing of progression, or shortening of duration, whether permanent or temporary, lasting or transient that are attributed to or associated with administration of the compound or composition.

The term "modulate," as used herein, means to interact with a target protein either directly or indirectly so as to alter the activity of the target protein, including, by way of example only, to inhibit the activity of the target, or to limit or reduce the activity of the target.

As used herein, the term "modulator" refers to a compound that alters an activity of a target (e.g., a target protein). For example, in some embodiments, a modulator causes an increase or decrease in the magnitude of a certain activity of a target compared to the magnitude of the activity in the absence of the modulator. In certain embodiments, a modulator is an inhibitor, which decreases the magnitude of one or more activities of a target. In certain embodiments, an inhibitor completely prevents one or more activities of a target.

As used herein, "modulation" with reference to intracellular calcium refers to any alteration or adjustment in intracellular calcium including but not limited to alteration of calcium concentration in the cytoplasm and/or intracellular calcium storage organelles, e.g., endoplasmic reticulum, or alteration of the kinetics of calcium fluxes into, out of and within cells. In aspect, modulation refers to reduction.

The terms "inhibits", "inhibiting", or "inhibitor" of SOC channel activity or CRAC channel activity, as used herein, refer to inhibition of store operated calcium channel activity or calcium release activated calcium channel activity.

The term "acceptable" with respect to a formulation, composition or ingredient, as used herein, means having no persistent detrimental effect on the general health of the subject being treated.

The term "pharmaceutically acceptable," molecular entities and compositions that are physiologically tolerable and do not typically produce an allergic or similar untoward reaction, such as gastric upset, and dizziness, when administered to a human. Preferably, as used herein, the term "pharmaceutically acceptable" means approved by a regulatory agency of the federal or a state government or listed in the U.S. Pharmacopeia or other generally recognized pharmacopeia for use in animals, and more particularly in humans.

The term "pharmaceutical composition" refers to a mixture of a compound of the present invention with other chemical components, such as carriers, stabilizers, diluents, dispersing agents, suspending agents, thickening agents, and/or excipients.

The compounds and pharmaceutical compositions of the present invention can be administered by various routes of administration including, but not limited to, intravenous, oral, aerosol, parenteral, ophthalmic, pulmonary and topical administration.

The terms "effective amount" or "therapeutically effective amount," as used herein, refer to a sufficient amount of an agent or a compound being administered which will relieve to some extent one or more of the symptoms of the disease or condition being treated. The result is reduction and/or alleviation of the signs, symptoms, or causes of a disease, or any other desired alteration of a biological system. For example, an "effective amount" for therapeutic uses is the amount of a compound of the present invention required to provide a clinically significant decrease in disease symptoms. In some embodiments, an appropriate "effective" amount in any individual case is determined using techniques, such as a dose escalation study.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The term "carrier," as used herein, refers to relatively non-toxic chemical compounds or agents that facilitate the incorporation of a compound into cells or tissues.

The term "diluent" refers to chemical compounds that are used to dilute the compound of interest prior to delivery. In some embodiments, diluents are used to stabilize compounds because they provide a more stable environment. Salts dissolved in buffered solutions (which also provide pH control or maintenance) are utilized as diluents, including, but not limited to a phosphate buffered saline solution.

By "cancerous cell" is meant a cell from the lung, inclusive of a pre-malignant cell, a neoplastic cell, a malignant cell, a tumorigenic cell, a non-tumorigenic cell and a lung cancer stem cell.

As used herein, "intracellular calcium" refers to calcium located in a cell without specification of a particular cellular location. In contrast, "cytosolic" or "cytoplasmic" with reference to calcium refers to calcium located in the cell cytoplasm.

As used herein, an effect on intracellular calcium is any alteration of any aspect of intracellular calcium, including but not limited to, an alteration in intracellular calcium levels and location and movement of calcium into, out of or within a cell or intracellular calcium store or organelle. For example, in some embodiments, an effect on intracellular calcium is an alteration of the properties, such as, for example, the kinetics, sensitivities, rate, amplitude, and electrophysiological characteristics, of calcium flux or movement that occurs in a cell or portion thereof. In some embodiments, an effect on intracellular calcium is an alteration in any intracellular calcium-modulating process, including, store-operated calcium entry, cytosolic calcium buffering, and calcium levels in or movement of calcium into, out of or within an intracellular calcium store. Any of these aspects are assessed in a variety of ways including, but not limited to, evaluation of calcium or other ion (particularly cation) levels, movement of calcium or other ion (particularly cation), fluctuations in calcium or other ion (particularly cation) levels, kinetics of calcium or other ion (particularly cation) fluxes and/or transport of calcium or other ion (particularly cation) through a membrane. An alteration is any such change that is statistically significant. Thus, for example, in some embodiments, if intracellular calcium in a test cell and a control cell is said to differ, such differences are a statistically significant difference.

Modulation of intracellular calcium is any alteration or adjustment in intracellular calcium including but not limited to alteration of calcium concentration or level in the cytoplasm and/or intracellular calcium storage organelles, e.g., endoplasmic reticulum, alteration in the movement of calcium into, out of and within a cell or intracellular calcium store or organelle, alteration in the location of calcium within a cell, and alteration of the kinetics, or other properties, of calcium fluxes into, out of and within cells. In some embodiments, intracellular calcium modulation involves alteration or adjustment, e.g. reduction or inhibition, of store-operated calcium entry, cytosolic calcium buffering, calcium levels in or movement of calcium into, out of or within an intracellular calcium store or organelle, and/or basal or resting cytosolic calcium levels. The modulation of intracellular calcium involves an alteration or adjustment in receptor-mediated ion (e.g., calcium) movement, second messenger-operated ion (e.g., calcium) movement, calcium influx into or efflux out of a cell, and/or ion (e.g., calcium) uptake into or release from intracellular compartments, including, for example, endosomes and lysosomes.

As used herein, "involved in", with respect to the relationship between a protein and an aspect of intracellular calcium or intracellular calcium regulation means that when expression or activity of the protein in a cell is reduced, altered or eliminated, there is a concomitant or associated reduction, alteration or elimination of one or more aspects of intracellular calcium or intracellular calcium regulation. Such an alteration or reduction in expression or activity occurs by virtue of an alteration of expression of a gene encoding the protein or by altering the levels of the protein. A protein involved in an aspect of intracellular calcium, such as, for example, store-operated calcium entry, thus, are one that provides for or participates in an aspect of intracellular calcium or intracellular calcium regulation. For example, a protein that provides for store-operated calcium entry are a STIM protein and/or an Orai protein.

As used herein, a protein that is a component of a calcium channel is a protein that participates in multi-protein complex that forms the channel.

As used herein, "cation entry" or "calcium entry" into a cell refers to entry of cations, such as calcium, into an intracellular location, such as the cytoplasm of a cell or into the lumen of an intracellular organelle or storage site. Thus, in some embodiments, cation entry is, for example, the movement of cations into the cell cytoplasm from the extracellular medium or from an intracellular organelle or storage site, or the movement of cations into an intracellular organelle or storage site from the cytoplasm or extracellular medium. Movement of calcium into the cytoplasm from an intracellular organelle or storage site is also referred to as "calcium release" from the organelle or storage site.

As used herein, "cell response" refers to any cellular response that results from ion movement into or out of a cell or within a cell. In some embodiments, the cell response is associated with any cellular activity that is dependent, at least in part, on ions such as, for example, calcium. Such activities optionally include, for example, cellular activation, gene expression, endocytosis, exocytosis, cellular trafficking and apoptotic cell death.

As used herein, "immune cells" include cells of the immune system and cells that perform a function or activity in an immune response, such as, but not limited to, T-cells, B-cells, lymphocytes, macrophages, dendritic cells, neutrophils, eosinophils, basophils, mast cells, plasma cells, white blood cells, antigen presenting cells and natural killer cells.

As used herein, "cytokine" or "cytokines" refers to small soluble proteins secreted by cells that in some embodiments, alter the behavior or properties of the secreting cell or another cell. Cytokines bind to cytokine receptors and trigger a behavior or property within the cell, for example, cell proliferation, death or differentiation. Exemplary cytokines include, but are not limited to, interleukins (e.g., IL-2, IL-3, IL-4, IL-5, IL-6, IL-7, IL-8, IL-9, IL-10, IL-11, IL-12, IL-13, IL-15, IL-16, IL-17, IL-18, IL-1.alpha., IL-1.beta., and IL-1 RA), granulocyte colony stimulating factor (G-CSF), granulocyte-macrophage colony stimulating factor (GM-CSF), oncostatin M, erythropoietin, leukemia inhibitory factor (LIF), interferons, B7.1 (also known as CD80), B7.2 (also known as B70, CD86), TNF family members (TNF-.alpha., TNF-.beta., LT-.beta., CD40 ligand, Fas ligand, CD27 ligand, CD30 ligand, 4-1BBL, Trail), and MIF.

"Store operated calcium entry" or "SOCE" refers to the mechanism by which release of calcium ions from intracellular stores is coordinated with ion influx across the plasma membrane.

Cellular calcium homeostasis is a result of the summation of regulatory systems involved in the control of intracellular calcium levels and movements. Cellular calcium homeostasis is achieved, at least in part, by calcium binding and by movement of calcium into and out of the cell across the plasma membrane and within the cell by movement of calcium across membranes of intracellular organelles including, for example, the endoplasmic reticulum, sarcoplasmic reticulum, mitochondria and endocytic organelles including endosomes and lysosomes.

Movement of calcium across cellular membranes is carried out by specialized proteins. For example, calcium from the extracellular space enters the cell through various calcium channels and a sodium/calcium exchanger and is actively extruded from the cell by calcium pumps and sodium/calcium exchangers. Calcium is also released from internal stores through inositol trisphosphate or ryanodine receptors and is likely taken up by these organelles by means of calcium pumps.

Calcium enters cells by any of several general classes of channels, including but not limited to, voltage-operated calcium (VOC) channels, store-operated calcium (SOC) channels, and sodium/calcium exchangers operating in reverse mode. VOC channels are activated by membrane depolarization and are found in excitable cells like nerve and muscle and are for the most part not found in nonexcitable cells. Under some conditions, $Ca^{2+}$ also enters cells via $Na^+$—$Ca^{2+}$ exchangers operating in reverse mode.

Endocytosis provides another process by which cells take up calcium from the extracellular medium through endosomes. In addition, some cells, e.g., exocrine cells, release calcium via exocytosis.

Cytosolic calcium concentration is tightly regulated with resting levels usually estimated at approximately 0.1 .mu.M in mammalian cells, whereas the extracellular calcium concentration is typically about 2 mM. This tight regulation facilitates transduction of signals into and within cells through transient calcium flux across the plasma membrane and membranes of intracellular organelles. There is a multiplicity of intracellular calcium transport and buffer systems in cells that serve to shape intracellular calcium signals and maintain the low resting cytoplasmic calcium concentration. In cells at rest, the principal components involved in maintaining basal calcium levels are calcium pumps and leaks in the endoplasmic reticulum and plasma membrane. Disturbance of resting cytosolic calcium levels effects transmission of such signals and give rise to defects in a number of cellular processes. For example, cell proliferation involves a prolonged calcium signalling sequence. Other cellular processes include, but are not limited to, secretion, signalling, and fertilization, involve calcium signalling.

Cell-surface receptors that activate phospholipase C(PLC) create cytosolic $Ca^{2+}$ signals from intra- and extra-cellular sources. An initial transient rise of $[Ca^{2+}]_i$ (intracellular calcium concentration) results from the release of $Ca^{2+}$ from the endoplasmic reticulum (ER), which is triggered by the PLC product, inositol-1,4,5-trisphosphate ($P_3$), opening $IP_3$ receptors in the ER (Streb et al. Nature, 306, 67-69, 1983). A subsequent phase of sustained $Ca^{2+}$ entry across the plasma membrane then ensues, through specialized store operated calcium (SOC) channels (in the case of immune cells the SOC channels are calcium release-activated calcium (CRAC) channels) in the plasma membrane. Store-operated $Ca^{2+}$ entry (SOCE) is the process in which the emptying of $Ca^{2+}$ stores itself activates $Ca^{2+}$ channels in the plasma membrane to help refill the stores (Putney, Cell Calcium, 7, 1-12, 1986; Parekh et al, Physiol. Rev. 757-810; 2005). SOCE does more than simply provide $Ca^{2+}$ for refilling stores, but itself generates sustained $Ca^{2+}$ signals that control such essential functions as gene expression, cell metabolism and exocytosis (Parekh and Putney, Physiol. Rev. 85, 757-810 (2005).

In lymphocytes and mast cells, activation of antigen or Fc receptors causes the release of $Ca^{2+}$ from intracellular stores, which in turn leads to $Ca^{2+}$ influx through CRAC channels in the plasma membrane. The subsequent rise in intracellular $Ca^{2+}$ activates calcineurin, a phosphatase that regulates the transcription factor NFAT. In resting cells, NFAT is phosphorylated and resides in the cytoplasm, but when dephosphorylated by calcineurin, NFAT translocates to the nucleus and activates different genetic programmes depending on stimulation conditions and cell type. In response to infections and during transplant rejection, NFAT partners with the transcription factor AP-1 (Fos-Jun) in the nucleus of "effector" T cells, thereby trans activating cytokine genes, genes that regulate T cell proliferation and other genes that orchestrate an active immune response (Rao et al., Annu Rev Immunol, 1997; 15:707-47). In contrast, in T cells recognizing self antigens, NFAT is activated in the absence of AP-1, and activates a transcriptional programme otherwise known as "anergy" that suppresses autoimmune responses (Macian et al., Transcriptional mechanisms underlying lymphocyte tolerance. Cell. 2002 Jun. 14; 109(6):719-31). In a subclass of T cells, known as regulatory T cells which suppress autoimmunity mediated by self-reactive effector T cells, NFAT partners with the transcription factor FOXP3 to activate genes responsible for suppressor function (Wu et al., Cell, 2006 Jul. 28; 126(2):375-87; Rudensky A Y, Gavin M, Zheng Y. Cell. 2006 Jul. 28; 126(2): 253-256).

The endoplasmic reticulum (ER) carries out a variety processes. The ER has a role as both an agonist-sensitive $Ca^{2+}$ store and sink, protein folding/processing takes place within its lumen. Here, numerous $Ca^{2+}$-dependent chaperone proteins ensure that newly synthesized proteins are folded correctly and sent off to the appropriate destination. The ER is also involved in vesicle trafficking, release of stress signals, regulation of cholesterol metabolism, and apoptosis. Many of these processes require intraluminal $Ca^{2+}$, and protein misfolding, ER stress responses, and apoptosis are all likely induced by depleting the ER of $Ca^{2+}$ for prolonged periods of time. Because of its role as a source of $Ca^{2+}$, it is clear that ER $Ca^{2+}$ content must fall after stimulation. However, to preserve the functional integrity of the ER, it is vital that the $Ca^{2+}$ content does not fall too low or is maintained at a low level. Replenishment of the ER with $Ca^{2+}$ is therefore a central process to all eukaryotic cells. Because a fall in ER $Ca^{2+}$ content activates store-operated $Ca^{2+}$ channels in the plasma membrane, a major function of this $Ca^{2+}$ entry pathway is believed to be maintenance of ER $Ca^{2+}$ levels that are necessary for proper protein synthesis and folding. However, store-operated $Ca^{2+}$ channels have other important roles.

The understanding of store operated calcium entry was provided by electrophysiological studies which established that the process of emptying the stores activated a $Ca^{2+}$ current in mast cells called $Ca^{2+}$ release-activated $Ca^{2+}$ current or $I_{CRAC}$. $I_{CRAC}$ is non-voltage activated, inwardly rectifying, and remarkably selective for $Ca^{2+}$. It is found in several cell types mainly of hemopoietic origin. $I_{CRAC}$ is not the only store-operated current, and it is now apparent that store-operated influx encompasses a family of $Ca^{2+}$-permeable channels, with different properties in different cell types. $I_{CRAC}$ was the first store-operated $Ca^{2+}$ current to be described and remains a popular model for studying store-operated influx.

Effects of compounds or agents on intracellular calcium can be monitored using various screening/identification methods which provide for a direct or indirect evaluation or measurement of cellular (including cytosolic and intracellular organelle or compartment) calcium and/or movement of ions into, within or out of a cell, organelle, calcium store or portions thereof (e.g., a membrane). A variety of methods can be used for evaluating calcium levels and ion movements or flux. The particular method used and the conditions employed would depend on whether a particular aspect of intracellular calcium is being monitored or assessed. For example, in some aspects, reagents and conditions may be used for specifically evaluating store-operated calcium entry, resting cytosolic calcium levels, calcium buffering and calcium levels and uptake by or release from intracellular organelles and calcium stores. Alternately, the effect of a compound or agent on intracellular calcium can be monitored or assessed using, for example, a cell, an intracellular organelle or calcium storage compartment, a membrane (including, e.g., a detached membrane patch or a lipid bilayer) or a cell-free assay system (e.g., outside-out membrane vesicle). Generally, some aspect of intracellular calcium is monitored or assessed in the presence of test agent and compared to a control, e.g., intracellular calcium in the absence of test agent.

Diseases, Disorders or Conditions

Clinical studies demonstrate that the CRAC channel is absolutely required for the activation of genes underlying the T cell response to antigen. Sustained calcium entry is needed for lymphocyte activation and adaptive immune response. Calcium entry into lymphocytes occurs primarily through the CRAC channels. Increased calcium leads to NFAT activation and expression of cytokines required for immune response. Inhibiting the store operated calcium entry is an efficient way to prevent T cell activation.

Inhibition of CRAC channel activity with the compounds that modulate intracellular calcium levels provide a means for providing immunosuppressive therapy as demonstrated by the elimination of store-operated calcium entry noted in patients with severe-combined immunodeficiency (SCID). T cells, fibroblasts, and in some cases B cells, from patients with T cell immunodeficiency or SCID having a principal defect in T cell activation show a strong defect in store-operated calcium entry. SCID patients lack adaptive immune response, but without any impairment or toxicity in major organs. The SCID patient phenotype indicates that inhibition of CRAC channels is an effective strategy for immunosuppression.

Diseases/Disorders Involving Inflammation and Diseases/Disorders Related to the Immune System In some embodiments, diseases, disorders or conditions that are treated or prevented using compounds disclosed herein that are capable of modulating intracellular calcium levels, compositions thereof, and methods provided herein to identify compounds capable of modulating intracellular calcium levels, include diseases, conditions or disorders involving inflammation and/or that are related to the immune system. These diseases include, but are not limited to, asthma, chronic obstructive pulmonary disease, rheumatoid arthritis, inflammatory bowel disease, glomerulonephritis, neuroinflammatory diseases such as multiple sclerosis, and disorders of the immune system.

The activation of neutrophils (PMN) by inflammatory mediators is partly achieved by increasing cytosolic calcium concentration. Store-operated calcium influx in particular is thought to play an important role in PMN activation. It has been shown that trauma increases PMN store-operated calcium influx and that prolonged elevations of cytosolic calcium concentration due to enhanced store-operated calcium influx likely alters stimulus-response coupling to chemotaxins and contribute to PMN dysfunction after injury. Modulation of PMN cytosolic calcium concentration through store-operated calcium channels might therefore be useful in regulating PMN-mediated inflammation and spare cardiovascular function after injury, shock or sepsis.

Calcium plays a critical role in lymphocyte activation. Activation of lymphocytes, e.g., by antigen stimulation, results in rapid increases in intracellular free calcium concentrations and activation of transcription factors, including nuclear factor of activated T cells (NFAT), NF-.kappa.B, JNK1, MEF2 and CREB. NFAT is a key transcriptional regulator of the IL-2 (and other cytokine) genes. A sustained elevation of intracellular calcium level is required to keep NFAT in a transcriptionally active state, and is dependent on store-operated calcium entry. Reduction or blocking of store-operated calcium entry in lymphocytes blocks calcium-dependent lymphocyte activation. Thus, in some embodiments, modulation of a STIM protein and/or an Orai protein, and particularly store-operated calcium entry (e.g., reduction in, elimination of store-operated calcium entry), in lymphocytes is a method for treating immune and immune-related disorders, including, for example, chronic immune diseases/disorders, acute immune diseases/disorders, autoimmune and immunodeficiency diseases/disorders, diseases/disorders involving inflammation, organ transplant graft rejections and graft-versus-host disease and altered (e.g., hyperactive) immune responses. For example, in some embodiments treatment of an autoimmune disease/disorder involves reducing, blocking or eliminating store-operated calcium entry in lymphocytes.

Examples of immune disorders include, for example, psoriasis, rheumatoid arthritis, vasculitis, inflammatory bowel disease, dermatitis, osteoarthritis, asthma, inflammatory muscle disease, allergic rhinitis, vaginitis, interstitial cystitis, scleroderma, osteoporosis, eczema, allogeneic or xenogeneic transplantation (organ, bone marrow, stem cells and other cells and tissues) graft rejection, graft-versus-host disease, lupus erythematosus, inflammatory disease, type I diabetes, pulmonary fibrosis, dermatomyositis, Sjogren's syndrome, thyroiditis (e.g., Hashimoto's and autoimmune thyroiditis), myasthenia gravis, autoimmune hemolytic anemia, multiple sclerosis, cystic fibrosis, chronic relapsing hepatitis, primary biliary cirrhosis, allergic conjunctivitis and atopic dermatitis.

In other embodiments, compounds disclosed herein that are capable of modulating intracellular calcium levels, compositions thereof, and methods provided herein to identify compounds capable of modulating intracellular calcium levels, are used in connection with treatment of malignancies, including, but not limited to, malignancies of lymphoreticular origin, bladder cancer, breast cancer, colon cancer, endometrial cancer, head and neck cancer, lung cancer, melanoma, ovarian cancer, prostate cancer and rectal cancer. Store-operated calcium entry is thought to play an important role in cell proliferation in cancer cells.

Inhibition of SOCE is sufficient to prevent tumor cell proliferation. The pyrazole derivative BTP-2, a direct $I_{CRAC}$ blocker inhibits SOCE and proliferation in Jurkat cells and in colon cancer cells. Moreover, sustained SOCE requires mitochondrial $Ca^{2+}$ uptake and that prevention of mitochondrial $Ca^{2+}$ uptake leads to SOCE inhibition. Stimulation of Jurkat cells induces sustained SOCE and activation of the $Ca^{2+}$-dependent phosphatase calcineurin that dephosphorylates NFAT, promoting expression of interleukin-2 and proliferation. In other embodiments, compounds capable of modulating intracellular calcium levels inhibit SOCE and are used in the treatment of cancer or other proliferative diseases or conditions.

In some embodiments, diseases, disorders or conditions that are treated or prevented using compounds disclosed herein that are capable of modulating intracellular calcium levels, compositions thereof, and methods provided herein to identify compounds capable of modulating intracellular calcium levels, include, for example, hepatic or liver diseases and disorders. These diseases, conditions or disorders include but are not limited to liver injury, for example, due to transplantation, hepatitis and cirrhosis.

Store-operated calcium entry has been implicated in chronic liver disease as well as transplantation injury after cold preservation-warm deoxygenation.

In some embodiments, diseases, conditions or disorders that are treated or prevented using the compounds disclosed herein that are capable of modulating intracellular calcium levels, compositions thereof, and methods provided herein to identify compounds capable of modulating intracellular calcium levels, include kidney or renal diseases and disorders. Mesangial cell hyperplasia is often a key feature of such diseases and disorders. In other embodiments, such diseases and disorders are caused by immunological or other mechanisms of injury, including IgAN, membranoproliferative glomerulonephritis or lupus nephritis. Imbalances in the control of mesangial cell replication also appear to play a key role in the pathogenesis of progressive renal failure. The turnover of mesangial cells in normal adult kidney is very low with a renewal rate of less than 1%. A prominent feature of glomerular/kidney diseases is mesangial hyperplasia due to elevated proliferation rate or reduced cell loss of mesangial cells. When mesangial cell proliferation is induced without cell loss, for example due to mitogenic stimulation, mesangioproliferative glomerulonephritis does result. Data have indicated that regulators of mesangial cell growth, particularly growth factors, are thought to act by regulating store-operated calcium channels. In yet other embodiments, modulators of store-operated calcium influx aids in the treatment of glomerular diseases by inhibiting mesangial cell proliferation.

In one aspect, compounds described herein modulate intracellular calcium, such as but not limited to, modulation (e.g. reduction or inhibition) of SOC channel activity, such as inhibition of CRAC channel activity (e.g. inhibition of $I_{CRAC}$, inhibition of SOCE), in an immune system cell (e.g., a lymphocyte, white blood cell, T cell, B cell), a fibroblast (or a cell derived from a fibroblast), or an epidermal, dermal or skin cell (e.g., a keratinocyte). In some embodiments, the step of modulating one or more proteins involved in modulating intracellular calcium (e.g. a STIM protein and/or Orai protein) involves, for example, reducing the level, expression of, an activity of, function of and/or molecular interactions of a protein. For instance, if a cell exhibits an increase in calcium levels or lack of regulation of an aspect of intracellular calcium modulation, e.g., store-operated calcium entry, then in other embodiments, modulating involves reducing the level of, expression of, an activity or function of, or a molecular interaction of a protein, e.g. a STIM protein and/or Orai protein.

Methods of Identifying Therapeutic Agents for NSCLC

In one aspect, the present invention provides a method of identifying a therapeutic agent for treating NSCLC wherein the agent inhibits one or more plasma membrane calcium transportation pathways. The method includes determining whether a candidate agent can modulate all or part of the CRAC/STIM pathway in a NSCLC cell which, in turn, modifies one or more cancer-related properties of the epithelial cell.

By "cancer-related properties" is meant any physiological and/or pathological manifestation of a cell which results from cancer of the cell. Within the scope is promotion of transcription, proliferation of the cell, death of the cell (such as apoptosis and necrosis) and invasiveness, wherein invasiveness is inclusive of metastasis, migration and loss of adhesion.

It will be appreciated that in general forms, a candidate agent may directly modulate a CRAC channel. In an alternative form, a candidate agent may modulate a STIM protein to thereby alter calcium flow into a cancerous cell.

In the context of the present invention, "alter" or "alteration" includes within its scope a decrease, lowering or otherwise down-regulation of calcium flow across a plasma membrane. It is envisaged that alteration of calcium flow into a cancerous cell includes selective alteration of calcium flow.

It will be readily appreciated that the mechanism of "modulation", "modulator" or "modulating" includes within its scope any interaction which interferes with, inhibits, blocks or hinders or activates or augments either the calcium-flow related activity of the CRAC channel and/or STIM protein. In certain embodiments, the modulator is an inhibitor. In other embodiments, the modulator is an antagonist. In yet other embodiments, the modulator is an agonist. In further embodiments, the modulator is an activator.

In one embodiment of the present invention, the candidate agent selectively modulates a CRAC channel and/or STIM protein. In another embodiment, the candidate agent selectively inhibits a CRAC channel and/or a STIM protein. In yet another embodiment, the candidate agent alters calcium flow by inhibition of a CRAC channel and/or STIM protein.

Accordingly, modulators may be peptides, proteins such as antibodies or other organic molecules (such as small organic molecules), with a desired biological activity and half-life. It is envisaged that both polyclonal and monoclonal antibodies directed to either the entire protein or a biologically-active fragment thereof are suitable modulators.

By "biologically-active fragment" is meant a fragment, portion, region or segment of a protein which displays at least 10%, preferably at least 25%, more preferably at least 50% and even more preferably at least 70%, 80% or 90% of the biological activity of the entire or full-length protein.

In relation to a CRAC channel, biological activity is calcium transport activity. With regard to a STIM protein, the biological activity is the ability to activate calcium transport into a cell by either a direct or indirect interaction with a CRAC channel.

It will be appreciated by a person of ordinary skill in the art that antibodies employed for therapeutic applications in humans must have specific properties which make these antibodies suitable for use in humans. Generally, therapeutic antibodies are "humanised", wherein the antibody typically comprises over 90% human sequence and the complementary determining regions of murine antibodies. Humanised antibodies are particularly advantageous for medical applications due to the decreased likelihood of eliciting a foreign body immune reaction.

It in envisaged that humanised antibodies may be directed to any STIM such as, but not limited to, STIM1 and STIM2. In one embodiment, the humanised antibody is directed to STIM1.

In other particular embodiments, the modulating agent is an antibody directed to a CRAC channel. In an alternative particular embodiment, the antibody directed to a CRAC channel is directed to CRACM1.

It is readily contemplated that effective modulating agents include other potential CRAC channel inhibitors which may be useful according to the present invention. Suitable examples include, but are not limited to, SKF-96365, T182, YM-58483, BTP-2, lanthanides such as, gadolinium and other CRAC channel modulators compounds as disclosed, for example, in PCT or US patent applications assigned to Synta Pharmaceuticals viz. WO 2005/009954, WO 2005/009539, WO 2005/009954, WO 200/6034402, A1, WO 2006/081389, WO 2006/081391, WO 2007/087429, WO 2007/087427, WO 2007/087441, WO 2007/087442, WO 2007/087443, WO 2007/089904, WO 2007/109362, WO 2007/112093, WO 2008/039520, WO 2008/063504, WO 2008/103310, WO 2009/017818, WO 2009/017819, WO 2009/017831, US 2006/0173006 US 2007/0249051 A1, WO 2010/039238, WO 2010/039237, WO 2010/039236, WO 2009/089305 and WO 2009/038775; patents and/or patent applications by Astellas, Queens Medical Center, Calcimedica and others including, viz., WO 2007/121186, WO 2006/0502 14, WO 2007/139926, WO 2008/148108, U.S. Pat. No. 7,452,675, US 2009/023177, WO 2007/139926, U.S. Pat. No. 6,696,267, U.S. Pat. No. 6,348,480, WO 2008/106731, US 2008/0293092, WO 2010/048559, WO 2010/027875, WO 2010/025295, WO 2010/034011, WO 2010/034003, WO 2009/076454, WO 2009/035818, US 2010/0152241, US 2010/0087415, US 2009/0311720 and WO 2004/078995.

Further suitable CRAC channels modulators include those disclosed in Isabella Derler et al. Expert opinion in *Drug Discovery* 3(7) (2008) pg. 787-800; Yousang G et al., *Cell Calcium* 42 (2007) 145-156; Yasurio Yonetoky et al., *Bio. & Med. Chem.* 14 (2006) 4750-4760 and Yasurio Yonetoky et al., *Bio. & Med. Chem.* 14 (2006) 5370-5383. All of these patents and/or patent applications and literature disclosures are incorporated herein as reference in their entirety for all purposes.

It is further contemplated that a molecular biological approach to modulation of the CRAC/STIM pathway may be employed. RNA interference, such as siRNA, provides an attractive method for silencing of potential therapeutic gene targets by sequence-specific cleavage of cognate mRNA. Takeshita and Ochiya (*Cancer Sci*, 2006, 97: 689-696) provide numerous examples of the therapeutic potential of RNA interference against cancer and is incorporated herein by reference.

The term "gene" is used herein to describe a discrete nucleic acid locus, unit or region within a genome that may comprise one or more of introns, exons, splice sites, open reading frames and 5' and/or 3' non-coding regulatory sequences such as a promoter and/or a polyadenylation sequence.

Therefore a person of skill in the art will readily appreciate that the invention contemplates a genetic construct which comprises one or more nucleotide sequences capable of directing synthesis of an RNA molecule, where the nucleotide sequence is selected from:

(i) a nucleotide sequence transcribable to an RNA molecule comprising an RNA sequence which is substantially homologous to an RNA sequence encoded by a nucleotide sequence of interest;
(ii) a reverse complement of the nucleotide sequence of (i);
(iii) a combination of the nucleotide sequences of (i) and (ii),
(iv) multiple copies of nucleotide sequences of (i), (ii) or (iii), optionally separated by a spacer sequence;
(v) a combination of the nucleotide sequences of (i) and (ii), wherein the nucleotide sequence of (ii) represents an inverted repeat of the nucleotide sequence of (i), separated by a spacer sequence; and
(vi) a combination as described in (v), wherein the spacer sequence comprises an intron sequence spliceable from said combination;

Where the nucleotide sequence comprises an inverted repeat separated by a non-intron spacer sequence, upon transcription, the presence of the non-intron spacer sequence facilitates the formation of a stem-loop structure by virtue of the binding of the inverted repeat sequences to each other. The presence of the non-intron spacer sequence causes the transcribed RNA sequence (also referred to herein as a "transcript") so formed to remain substantially in one piece, in a form that may be referred to herein as a "hairpin". Alternatively, where the nucleotide sequence comprises an inverted repeat where the spacer sequence comprises an intron sequence, upon transcription, the presence of intron/exon splice junction sequences on either side of the intron sequence facilitates the removal of what would otherwise form into a loop structure. The resulting transcript comprises a double-stranded RNA (dsRNA) molecule, optionally with overhanging 3' sequences at one or both ends. Such a dsRNA transcript is referred to herein as a "perfect hairpin". The RNA molecules may comprise a single hairpin or multiple hairpins including "bulges" of single-stranded DNA occurring in regions of double-stranded DNA sequences.

Depending upon the application, the RNA molecule may be directed to a single target or alternatively, a plurality of targets.

In certain embodiments, the RNA molecule encodes CRACM1/Orai1, CRACM2/Orai1 or CRACM3/Orai1 and/or STIM1 or STIM2.

Persons skilled in the art will be aware that therapeutic agents of the invention for the treatment of cancer may be identified by any number of methods. Accordingly, the method of identifying therapeutic agents involves determination of whether a candidate agent can directly modulate a CRAC channel and/or modulate STIM proteins. In one embodiment, the method involves determining whether the candidate agent can alter a flow of calcium into a cell by modulating a CRAC channel and/or STIM protein.

In one embodiment, the therapeutic agents of the invention for the treatment of NSCLC may be identified by way of screening libraries of molecules such as synthetic chemical libraries, including combinatorial libraries, by methods such as described in Nestler & Liu, 1998, *Comb. Chem. High Throughput Screen*, 1, 113 and Kirkpatrick et al., 1999, *Comb. Chem. High Throughput Screen*, 2, 211.

It is also contemplated that libraries of naturally-occurring molecules may be screened by known methods, such as those described in Kolb, 1998, *Prog. Drug. Res.* 51, 185. Similarly, the molecules may also be identified from a molecular libraries program (MLP) such as that offered by the National Institute of Health (NIH), USA.

More rational approaches to designing therapeutic agents for the treatment of NSCLC may employ X-ray crystallography, NMR spectroscopy, computer assisted screening of structural databases, computer-assisted modelling, or more traditional biophysical techniques which detect molecular binding interactions, as are known in the art.

Structural bioinformatics may also be used to identify candidate agents for treating NSCLC. A review of structural bioinformatics approaches to drug discovery is provided in Fauman et al., 2003, *Meth. Biochem. Anal.* 44:477, and *Nature Reviews Drug Discovery* 7, 783 (September 2008), both of which are incorporated by reference.

Computer-assisted structural database searching and bioinformatic approaches are becoming increasingly utilized as a procedure for identifying and/or engineering agonists and antagonist molecules. Examples of database searching methods may be found in U.S. Pat. No. 5,752,019 and International Publication No. WO 97/41526 (directed to identifying EPO mimetics) and U.S. Pat. Nos. 7,158,891 and 5,680,331 which are directed to more general computational approaches to protein modeling and structural mimicry of protein activity.

Generally, other applicable methods include any of a variety of biophysical techniques which identify molecular interactions. Such methods include, but are not limited to, competitive radioligand binding assays, electrophysiology, analytical ultracentrifugation, microcalorimetry, surface plasmon resonance and optical biosensor-based methods, such as those provided in Chapter 20 of CURRENT PROTOCOLS IN PROTEIN SCIENCE Eds. Coligan et al., (John Wiley & Sons, 1997), which is incorporated herein by reference.

A person skilled in the art will appreciate that modulating agents may be in the form of a binding partner and as such, identified by interaction assays such as yeast two-hybrid approaches. Two-hybrid screening methods are provided in Chapter 20 of CURRENT PROTOCOLS IN PROTEIN SCIENCE Eds. Coligan et al., (John Wiley & Sons, 1997) which is incorporated herein by reference.

Pharmaceutical Composition and Method of Treatment of NSCLC

It is also contemplated that in one aspect, the present invention provides a pharmaceutical composition that includes a therapeutic agent effective for treatment of cancer identified by a method described above, together with a pharmaceutically-acceptable carrier, diluent or excipient.

In another aspect, the present invention provides a method of treating cancer in a human by administering to the human a therapeutic agent effective for treatment of cancer identified by a method described above. The therapeutic agent, such as a CRAC inhibitor, may be used as a monotherapy or as an adjunctive therapy with one or more other methods of treating NSCLC.

In one embodiment, the therapeutic agent effective for treatment of cancer is in the form of a small organic molecule or peptide formulated with a pharmaceutically-acceptable carrier, diluent or excipient suitable for oral administration, as a transdermal patch or other non-invasive route of administration.

In yet another aspect, the present invention includes a method of treating a patient suffering from NSCLC by administering to the patient an effective amount of a CRAC inhibitor. The CRAC inhibitor may be used as a monotherapy or as an adjunctive therapy with one or more other methods of treating lung cancer (or NSCLC) which include chemotherapeutic agents for the treatment of lung cancer such as, for example, Cisplatin (Platinol®), Etoposide (VP-16; VePesid®), Carboplatin (Paraplatin®), Paclitaxel (Taxol®), Docetaxel (Taxotere®), Vinorelbine tartarate (Novelbine®), Doxorubicin (Adriamycin®), Vincristine Sulphate (Oncovin®), Ifosfamide (Ifex®) and Gemcitabine hydrochloride (Gemzar®).

As an adjunctive therapy, a CRAC inhibitor may be used along with the a standard chemotherapy for lung cancer, which typically consists of combinations of two or more of, for example, Cisplatin (Platinol®), Etoposide (VP-16; VePesid®), Carboplatin (Paraplatin®), Paclitaxel (Taxol®), Docetaxel (Taxotere®), Vinorelbine tartarate (Novelbine®), Doxorubicin (Adriamycin®), Vincristine Sulphate (Oncovin®), Ifosfamide (Ifex®) and Gemcitabine hydrochloride (Gemzar®). Such standard chemotherapy combination therapy has been shown to improve the overall response to treatment. Well-known drug pairings in standard chemotherapy combination therapy include paclitaxel plus carboplatin, cisplatin plus vinorelbine tartarate, cisplatin plus etoposide, and carboplatin plus etoposide. Concurrent radiotherapy is very often used with the standard chemotherapy combinations of cisplatin plus etoposide or carboplatin plus etoposide.

Other chemotherapeutic agents that may be used to treat lung cancer include, for example, Cyclophosphamide (Neosar®), Methotrexate, Lomustine (CCNU) and Topotecan hydrochloride (Hycamtin®).

For Non-Small Cell Lung Carcinoma as an adjunctive therapy, a CRAC inhibitor may be used in combination with Gemcitabine hydrochloride (Gemzar®), a chemotherapeutic drug that has unique activity against many solid tumors, including non-small cell lung cancer (NSCLC). Combination therapy with gemcitabine, cisplatin and vinorelbine tartarate has been found to be safe and very active in persons with advanced NSCLC. Another treatment option for NSCLC patients with advanced disease is alternating chemo-radiotherapy (e.g., cisplatin and etoposide, followed by radiotherapy).

The term "pharmaceutically-acceptable carrier, diluent or excipient" includes a solid or liquid filler, diluent or encapsulating substance that may be safely used in systemic administration. Depending upon the particular route of administration, a variety of carriers known in the art may be used. These carriers may be selected from sugars, starches, cellulose and its derivatives, malt, gelatine, talc, calcium sulfate, vegetable oils, synthetic oils, polyols, alginic acid, phosphate buffered solutions, emulsifiers, isotonic saline and salts such as mineral acid salts including hydrochlorides, bromides and sulfates, organic acids such as acetates, propionates and malonates and pyrogen-free water.

A useful reference describing pharmaceutically acceptable carriers, diluents and excipients is Remington's Pharmaceutical Sciences (Mack Publishing Co. N.J. USA, 1991), which is incorporated herein by reference.

Any safe route of administration may be employed for providing a patient with the therapeutic agent or pharmaceutical composition of the invention. For example, oral, rectal, parenteral, sublingual, buccal, intravenous, intra-articular, intra-muscular, intra-dermal, subcutaneous, inhalational, intraocular, intraperitoneal, intracerebroventricular and transdermal administration may be employed.

Suitable dosage forms include, but are not limited to, tablets, dispersions, suspensions, injections, solutions, syrups, troches, capsules, suppositories, aerosols, and transdermal patches. These dosage forms may also include injecting or implanting controlled releasing devices designed specifically for this purpose or other forms of implants modified to act additionally in this fashion. Controlled release of the therapeutic agent may be effected by coating the same, for example, with hydrophobic polymers including acrylic resins, waxes, higher aliphatic alcohols, polylactic and polyglycolic acids and certain cellulose derivatives such as hydroxypropylmethyl cellulose. In addition, the controlled release may be effected by using other polymer matrices, liposomes and/or microspheres.

Pharmaceutical compositions of the present invention suitable for oral or parenteral administration may be presented as discrete units such as capsules, sachets or tablets each containing a pre-determined amount of one or more therapeutic agents of the invention, as a powder or granules or as a solution or a suspension in an aqueous liquid, a non-aqueous liquid, an oil-in-water emulsion or a water-in-oil liquid emulsion. Such compositions may be prepared by any of the methods of pharmacy such as by bringing into association one or more agents as described above with the carrier which constitutes one or more ingredients. The compositions can be prepared by uniformly and intimately admixing the agents of the invention with liquid carriers or finely divided solid carriers or both, and then, optionally, shaping the product into the desired presentation.

The above compositions may be administered in a manner compatible with the dosage formulation, and in such amount as is pharmaceutically-effective. The dose administered to a patient, in the context of the present invention, should be sufficient to effect a beneficial response in a patient over an appropriate period of time. The quantity of agent(s) to be administered may depend on the subject to be treated inclusive of the age, sex, weight and general health condition thereof, factors that will depend on the judgement of the practitioner.

Diagnostic Methods

In yet another embodiment, the present invention is directed towards diagnostic methods for NSCLC which utilise CRAC channels and STIM proteins as diagnostic markers. In one particular aspect, the invention provides a diagnostic method for determining whether a patient may be responsive to treatment with a therapeutic agent that alters calcium influx via the CRAC and/or STIM pathway by measuring levels of plasma membrane associated STIM in a cancerous cell.

In one particular embodiment, the invention provides a diagnostic method for determining if a human is predisposed to or is suffering from NSCLC by detecting excessive levels of STIM protein in a cancerous cell, such as a cell from a lung.

In another particular aspect, the diagnostic method of the present invention includes measurement of the ratio of one particular form of STIM relative to another particular form of STIM.

In an additional embodiment, the present invention provides a diagnostic method to detect activation of CRAC channel expression in lung cells. It is envisaged that CRAC channel expression may be analysed by either protein-based or nucleic acid-based techniques.

Thus "predisposed" and "predisposition" are used in the context of a probability that an individual may display clinical symptoms of NSCLC, or that any existing, manifest clinical symptoms of NSCLC are the result of an underlying biochemical cause.

It will be readily appreciated by a person of skill in the art that a number of methods may be utilised to measure the expression levels of STIM on the plasma membrane of a cancerous cell. By way of example only, fluorescence activated cell sorting (FACS) analysis using labelled antibodies is readily amenable to quantitative measurement of cell surface expression of proteins. For example, immunofluorescence and other fluorescence microscopy methods can also be used to stain tissue to detect levels of STIM. Other conventional immunohistochemistry techniques may also be used.

Alternatively, relative protein expression levels may be determined by other protein-based methods which include immunoassays, for example, ELISA and immunoblotting to detect relative expression levels of one or more of the proteins.

Proteomic pattern analysis provides an alternative diagnostic method which is particularly useful for global expression pattern analysis of proteins. Methods of cancer diagnosis using proteomic patterns are provided in Conrads et al., *Expert Rev Mol Diagn*. 2003 July; 3(4):411-20 and is incorporated herein by reference.

In particular embodiments, a plurality of the proteins may be used in a protein library displayed in a number of ways, e.g., in phage display or cell display systems or by two-dimensional gel electrophoresis, or more specifically, differential two-dimensional gel electrophoresis (2D-DIGE). These particular embodiments may generally be referred to as "proteomic" or "protein profiling" methods, such as described, for example, in Chapters 3.9.1 and 22 of CURRENT PROTOCOLS IN PROTEIN SCIENCE Eds. Coligan et al., John Wiley & Sons NY USA (1996-2002).

In certain embodiments relating to protein arrays, a cancer-associated protein of the invention (such as a NSCLC-associated protein) is located at an identifiable address on the array.

In exemplary embodiments, the protein array includes a substrate which is immobilized, impregnated, bound or otherwise coupled to a cancer-associated protein (such as a NSCLC-associated protein), or a fragment thereof.

The substrate may be a chemically-derivatized aluminium chip, a synthetic membrane such as PVDF or nitrocellulose, a glass slide or microtiter plates.

Detection of substrate-bound proteins may be performed using mass spectrometry, ELISA, immunohistochemistry, fluorescence microscopy or by colorimetric detection.

The diagnostic methods of the invention may involve measuring expression levels of a nucleic acid encoding a STIM protein and/or a CRAC channel. In this regard, nucleotide sequence variations in a promoter, for example, may affect the steady state levels of a CRAC channel gene transcript in one or more cells of an affected or predisposed individual.

It is also contemplated that relative levels of nucleic acids may be measured and/or compared in the diagnostic methods of the present invention. By way of example, a CRAC and/or STIM mRNA level may be measured.

Measurement of relative levels of a nucleic acid level compared to an expressed level of a reference nucleic acid may be conveniently performed using a nucleic acid array.

Nucleic acid array technology has become well known in the art and examples of methods applicable to array technology are provided, for example, in Chapter 22 of CURRENT PROTOCOLS IN MOLECULAR BIOLOGY Eds. Ausubel et al. (John Wiley & Sons NY USA 1995-2001).

An array can be generated by various methods, e.g., by photolithographic methods (see, e.g., U.S. Pat. Nos. 5,143,854; 5,510,270; and 5,527,681), mechanical methods (e.g., directed-flow methods as described in U.S. Pat. No. 5,384,261), pin-based methods (e.g., as described in U.S. Pat. No. 5,288,514), and bead-based techniques (e.g., as described in International Application No. PCT/US93/04145).

Reference is also made to Affymetrix nucleic acid array systems such as described in U.S. Pat. Nos. 5,858,659 and 6,300,063, which provide specific teaching in relation to nucleic acid array-based detection of disease-related polymorphisms.

In another particular form of this embodiment, quantitative or semi-quantitative PCR using primers corresponding to CRAC channel-encoding nucleic acids or STIM-encoding nucleic acids may be used to quantify relative expression levels of a CRAC channel nucleic acid or STIM nucleic acid to thereby determine whether an individual is predisposed to or suffering from NSCLC.

PCR amplification is not linear and hence end point analysis does not always allow for the accurate determination of nucleic acid expression levels.

Real-time PCR analysis provides a high throughput means of measuring gene expression levels. It uses specific primers, and fluorescence detection to measure the amount of product after each cycle. Hydridization probes utilise either quencher dyes or fluorescence directly to generate a signal. This method may be used to validate and quantify nucleic acid expression differences in cells or tissues obtained from cancer sufferers compared to cells or tissues obtained from non-sufferers.

The following general methodology described herein provides the manner and process of making and using the compound of the present invention and are illustrative rather than limiting. Further modification of provided methodology and additionally new methods may also be devised in order to achieve and serve the purpose of the invention. Accordingly, it should be understood that there may be other embodiments which fall within the spirit and scope of the invention as defined by the specification hereto.

General Method of Preparation of Compound of Formula (I)

The compounds of the present invention may be prepared by the following processes. Unless otherwise indicated, all the variables when used in the below formulae are to be understood to present those groups described above in relation to formula (IA). These methods can similarly be applied to other compounds of formula (I) (e.g, (IA-I), (IA-II), (IA-III) and (IA-IV).

Scheme 1 provides a general process for synthesis of a compound of formula (IA) wherein $L_1$ & $L_2$ together are —NH—CO—, R''' is hydrogen or halogen, and all other variables R, $R^1$, $R^2$, T, U, V, W, A and Cy are as described above in relation to formula (IA)

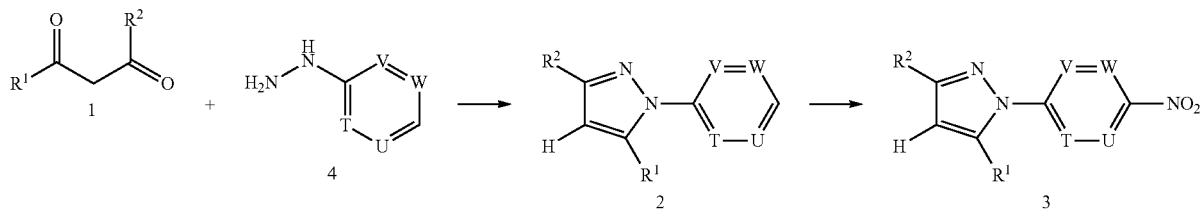

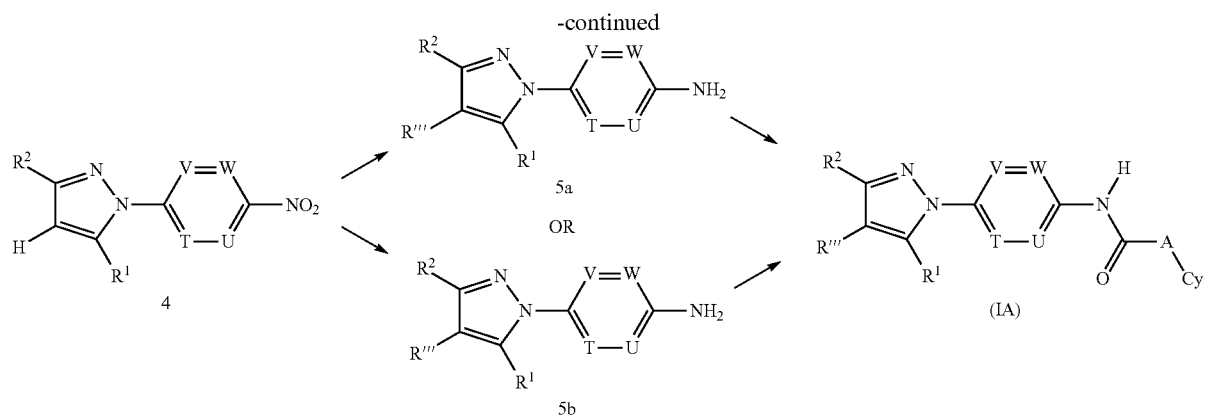

A compound of formula 1 can be reacted with a compound of formula 2 (e.g., phenyl hydrazine) to form a compound of formula 3. The compound of formula 3 can then be nitrated, e.g., using a mixture of concentrated $H_2SO_4$ and concentrated $HNO_3$ to form a compound of formula 4. Reduction of the compound of formula 4, such as with $FeCl_3$ and hydrazine in the presence of activated charcoal, yields the corresponding amine compound of formula 5a wherein R''' is Hydrogen. Alternately halogenation followed by reduction of the compound of formula 4, yields the corresponding amine compound of formula 5b wherein R''' is Halogen. The compound of formula 5a or 5b can be coupled with various other intermediates in the presence of a suitable coupling reagent to provide a compound of formula (IA). The compound of formula 5a or 5b can be coupled with i. Cy-A-COOH using one or more amide coupling reagents such as (benzotriazol-1-yloxy)tris(dimethylamino)phosphoniumhexafluoro phosphate (BOP reagent) or N-(3-dimethylaminopropyl)-N'-ethylcarbodiimide hydrochloride (EDC); ii. with acid chlorides of formula Cy-A-COCl; or iii. isocyanates of formula Cy-NCO where A is NH.

Scheme 2 provides a general process for synthesis of a compound of formula (IA) wherein $L_1$ & $L_2$ together i —NH—CO—, R''' is hydrogen or halogen and all other variables R, $R^1$, $R^2$, T, U, V, W, A and Cy are those described above in relation to formula (IA).

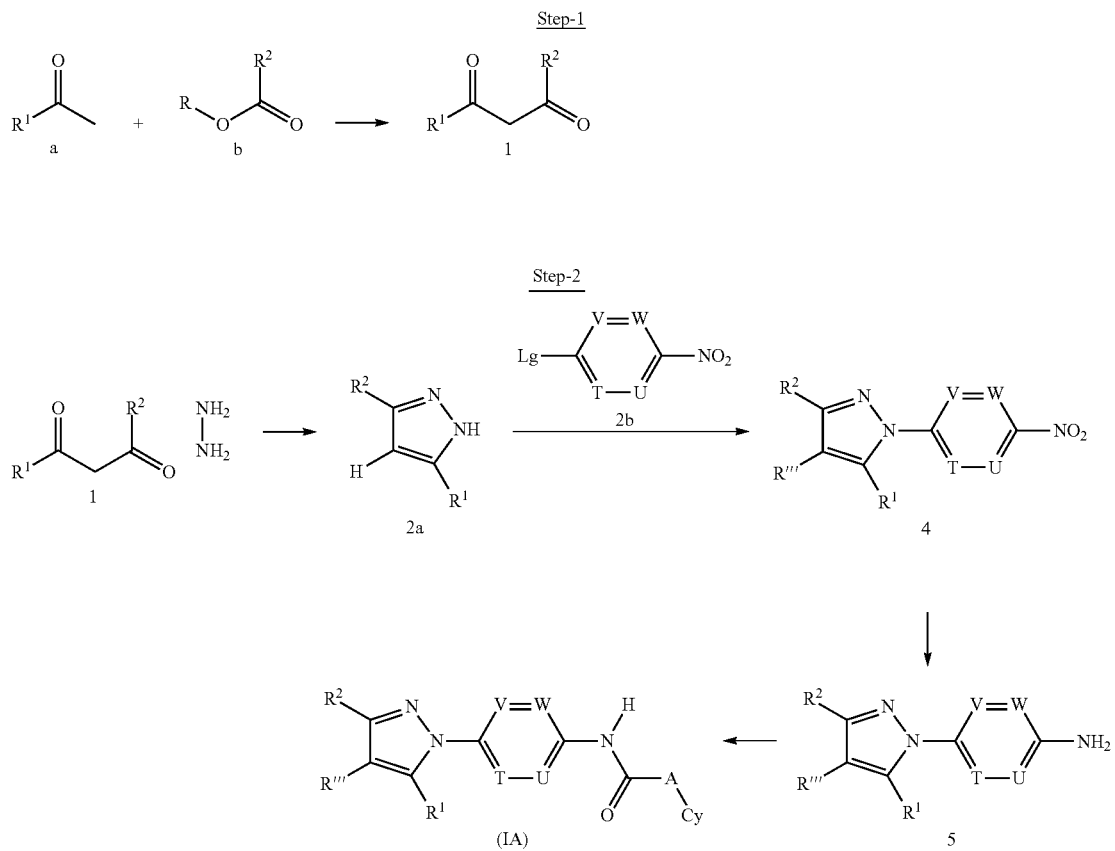

Step-1: A ketone of formula a can be condensed with an ester of formula b in the presence of a base such as a metal alkoxide, e.g., sodium ethoxide, to give a diketone of formula 1.

Step-2: The compound of formula 1 can be converted to a pyrazole compound of formula 2a by reacting it with hydrazine. The compound of formula 2a can be reacted with a compound of formula 2b wherein $L_g$ is a leaving group (such as a halogen) in the presence of a suitable base such as an alkali metal carbonate, e.g., $Cs_2CO_3$, to give a compound of formula 4, which can be subjected to a similar sequence of transformations as described above in scheme 1 to afford a compound of formula IA.

Scheme 2A provides a general process for synthesis of a compound of formula (IA) wherein $L_1$ & $L_2$ together is —CO—NH—, R''' is hydrogen or Halogen and all other variables R, $R^1$, $R^2$, T, U, V, W, A and Cy are those described above in relation to formula (IA).

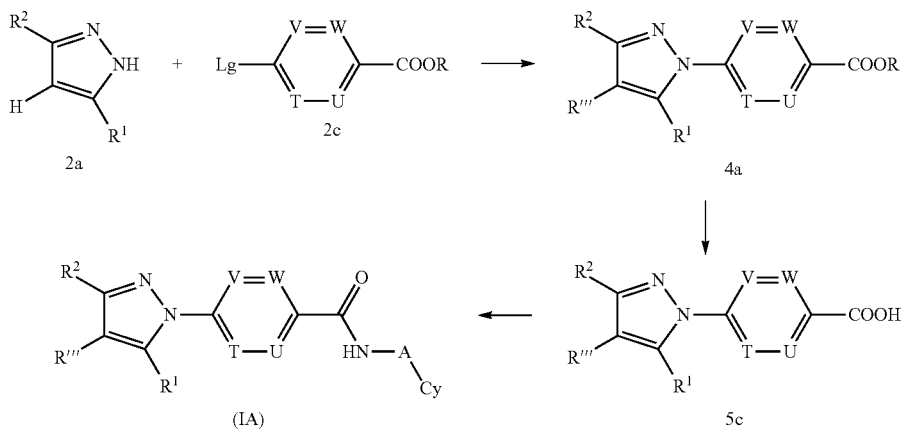

The compound of formula 2a can be reacted with a compound of formula 2c wherein $L_g$ is a leaving group (such as a halogen) in the presence of a suitable base such as an alkali metal carbonate, e.g., $Cs_2CO_3$, to give a compound of formula 4a, which can then be hydrolysed to give a compound of formula 5c. The compound of formula 5c can be coupled with Cy-A-$NH_2$ using one or more amide coupling reagents such as (benzotriazol-1-yloxy)tris(dimethylamino)phosphonium-hexafluoro phosphate (BOP reagent) or N-(3-dimethylaminopropyl)-N'-ethylcarbodiimide hydrochloride (EDC).

Similar methodologies with certain modifications as known to those skilled in the art can be used to synthesize compounds of formula (I), (IA-I) or (IA-II) wherein the variables are to be understood to present those groups described above in relation to formula (I), (IA-I), (IA-II), (IA-III) or (IA-IV) using suitable intermediates and reagents.

EXPERIMENTAL

The following abbreviations are used throughout this disclosure: EDC.HCl [N-(3-dimethylaminopropyl)-N'-ethylcarbodiimide hydrochloride], HOBt [Hydroxybenzotriazole], TEA (triethylamine), DMF (dimethyl formamide), AcOEt (ethyl acetate), DCM (dichloromethane), DMSO (dimethyl sulfoxide, THF (tetrahydrofuran). Unless otherwise mentioned, work-up implies distribution of reaction mixture between the aqueous and organic phases indicated within parentheses, separation and drying over $Na_2SO_4$ of the organic layer and evaporating the solvent to afford a residue. Unless otherwise stated, purification implies column chromatography using silica gel as the stationary phase and a mixture of petroleum ether (boiling at 60-80° C.) and ethyl acetate or dichloromethane and methanol of suitable polarity as the mobile phases. RT (or rt) implies ambient temperature (~25-28° C.).

Intermediate 1

1,3-dicyclopropylpropane-1,3-dione

Sodium ethoxide (8 g, 117.64 mmol) was added to a solution of cyclopropyl methyl ketone (5 g, 59.4 mmol) and methyl cyclopropane carboxylate (12 ml, 118.9 mmol) in DMSO (30 mL). The resulting mixture was heated at 60° C. overnight and then cooled to 0° C. After quenching the reaction with 6N HCl, work-up ($H_2O$/AcOEt) gave the title compound as a brown liquid which was used without any purification. $^1$H-NMR (δ ppm, $CDCl_3$, 400 MHz): 16.05 (bs, 0.6H), 5.72 (s, 0.6H) 3.78 (s, 0.8H), 2.08-2.0 (m, 0.8H), 1.62-1.53 (m, 1.2H), 1.12-1.05 (m, 4H), 0.97-0.83 (m, 4H). MS (m/z): 153.2 $[M+H]^+$.

Intermediate 2

1-cyclopropyl-4,4,4-trifluorobutane-1,3-dione

A procedure similar to that described for intermediate 1 was followed. From cyclopropyl methyl ketone (10 g, 119 mmol), ethyl 2,2,2-trifluoroacetate (29 ml, 237 mmol), DMSO (60 mL) and sodium ethoxide (16.1 g, 237 mmol), the title compound (15 g) was obtained as a brown liquid and was used in the next step without purification. $^1$H-NMR (δ ppm, $CDCl_3$, 400 MHz): 5.65 (s, 2H), 2.16-2.04 (m, 1H), 1.18-1.12 (m, 2H), 0.98-0.94 (m, 2H).

Intermediate 3

3,5-dicyclopropyl-1H-pyrazole

Intermediate 1 (5.3 g, 35 mmol) and hydrazine hydrate (1.8 mL, 38.3 mmol) in ethanol (20 mL) were refluxed overnight. Work-up ($H_2O$/AcOEt) after cooling the mixture to ambient temperature gave the title compound as a brown solid. M. P.: 161-164° C. $^1$H-NMR (δ ppm, $CDCl_3$, 400 MHz): 15.2 (bs, 1H), 5.65 (s, 1H), 2.16-2.09 (m, 2H), 1.18-1.14 (m, 4H), 0.98-0.94 (m, 4H). MS (m/z): 149.04 $[M+H]^+$.

Intermediate 4

5-cyclopropyl-3-(trifluoromethyl)-1H-pyrazole

Intermediate 2 (0.120 g, 0.66 mmol) and hydrazine hydrate (0.04 mL, 0.72 mmol) were dissolved in ethanol (6 mL) and refluxed overnight. Work-up ($H_2O$/AcOEt) after cooling the mixture to RT gave the title compound as a brown solid (0.114 g).

Intermediate 5

3,5-dicyclopropyl-1-(4-nitrophenyl)-1H-pyrazole

A solution of intermediate 3 (2.0 g, 13.5 mmol) and $Cs_2CO_3$ (5.51 g, 40.5 mmol) in DMSO (15 mL) was heated at 160° C. under nitrogen for 0.5 h. To the mixture, 4-chloro-1-nitro benzene (6.38 g, 40.5 mmol) was added and stirred at the same temperature for 4 h. Work-up ($H_2O$/AcOEt) and purification afforded the title compound (0.8 g). $^1$H-NMR (δ ppm, $CDCl_3$, 400 MHz): 8.32 (d, J 9.0, 2H), 7.92 (d, J 9.0, 2H), 5.76 (s, 1H), 1.97-1.91 (m, 1H), 1.86-1.80 (m, 1H), 1.09-1.04 (m, 2H), 0.98-0.94 (m, 2H), 0.83-0.75 (m, 4H).

Intermediate 6

3,5-dicyclopropyl-1-(2-fluoro-4-nitrophenyl)-1H-pyrazole

A solution of intermediate 3 (2.0 g, 13.5 mmol) and $K_2CO_3$ (5.5 g, 40.6 mmol) in DMSO (20 mL) were heated at 120° C. under nitrogen for 0.5 h. To this mixture, 3,4-difluoro-1-nitrobenzene (2.15 g, 13.5 mmol) was added and stirred at the same temperature for 2 h. Work-up ($H_2O$/AcOEt) and purification afforded the title compound as an yellow solid (3.16 g). $^1$H-NMR (δ ppm, $CDCl_3$, 400 MHz): 8.19-8.12 (m, 2H), 7.78 (t, J 7.9, 1H), 5.70 (s, 1H), 2.10-2.00 (m, 1H), 1.68-1.58 (m, 1H), 1.08-0.92 (m, 4H), 0.82-0.74 (m, 2H), 0.72-0.65 (m, 2H).

Intermediate 7

2-(3,5-dicyclopropyl-1H-pyrazol-1-yl)-5-nitropyridine

A solution of intermediate 3 (8.0 g, 54.05 mmol) and $K_2CO_3$ (27.96 g, 202.6 mmol) in DMSO (60 mL) was heated at 110° C. under nitrogen for 0.5 h. To the mixture, 2-chloro-5-nitro pyridine (12.8 g, 80.75 mmol) was added and stirred at the same temperature for 2 h. Work-up ($H_2O$/AcOEt) and purification afforded the title compound (3.03 g). $^1$H-NMR (δ ppm, $CDCl_3$, 400 MHz): 9.24 (d, J 2.6, 1H), 8.51 (dd, J 2.6, 9.9, 1H), 8.10 (d, J 9.2, 1H), 5.72 (s, 1H), 2.90-2.75 (m, 1H), 1.99-1.90 (m, 1H), 1.06-0.93 (m, 4H), 0.82-0.64 (m, 4H).

Intermediate 8

5-cyclopropyl-1-(4-nitrophenyl)-3-(trifluoromethyl)-1H-pyrazole

A procedure similar to that followed for intermediate 5 was employed. From intermediate 4 (1.0 g, 5.67 mmol), $Cs_2CO_3$ (5.5 g, 16.9 mmol), DMSO (4 mL) and 4-chloro-1-nitro benzene (1.93 g, 14.1 mmol) was obtained the title compound (0.7 g). $^1$H-NMR (δ ppm, $CDCl_3$, 400 MHz): 8.38 (d, J 7.08, 2H), 7.92 (d, J 7.08, 2H), 6.32 (s, 1H), 1.89-1.82 (m, 1H), 1.19-1.11 (m, 2H), 0.89-0.85 (m, 2H), MS (m/s): 298.15 [M+H]$^+$.

Intermediate 9

5-cyclopropyl-1-(2-fluoro-4-nitrophenyl)-3-(trifluoromethyl)-1H-pyrazole

A solution of intermediate 4 (6.3 g, 35 mmol) and $K_2CO_3$ (14.6 g, 105 mmol) in DMSO (20 mL) was heated at 120° C. under nitrogen for 30 mins. To this mixture, 1,2-difluoro nitrobenzene (5.68 g, 35 mmol) was added and stirred at the same temperature for 2 h. Work-up ($H_2O$/AcOEt) and purification afforded the title compound (7.52 g). $^1$H-NMR (δ ppm, DMSO-$d_6$, 400 MHz): 8.49 (dd, J 2.4, 9.9, 1H), 8.47-8.27 (m, 1H), 8.04-8.02 (m, 1H), 6.73 (s, 1H), 1.76-1.68 (m, 1H), 0.99-0.90 (m, 2H), 0.84-0.74 (m, 2H).

Intermediate 10

2-[5-cyclopropyl-3-(trifluoromethyl)-1H-pyrazol-1-yl]-5-nitropyridine

A solution of intermediate 4 (1.0 g, 5.67 mmol) and $K_2CO_3$ (2.35 g, 17.03 mmol) in DMSO (10 mL) was heated at 90° C. under nitrogen for 30 mins. To the mixture, 2-chloro-5-nitro pyridine (1.35 g, 8.5 mmol) was added and stirred at the same temperature for 2 h. Work-up ($H_2O$/AcOEt) and purification afforded the title compound (0.30 g). $^1$H-NMR (δ ppm, $CDCl_3$, 400 MHz): 9.33 (d, J 2.5, 1H), 8.62 (dd, J 2.8, 9.0, 1H), 8.19 (d, J 9.0, 1H), 6.29 (s, 1H), 2.92-2.83 (m, 1H), 1.60-1.50 (m, 2H), 0.79-0.70 (m, 2H).

Intermediate 11

2-[4-chloro-5-cyclopropyl-3-(trifluoromethyl)-1H-pyrazol-1-yl]-5-nitropyridine

Intermediate 10 (1.5 g, 5.0 mmol) was dissolved in DMF and to this N-Chlorosuccinimide (0.8 g, 6 mmol) was added at 0° C. Then reaction was allowed to stir at rt for 2 h. After completion of the reaction, work up (EtOAc) and purification afforded the title compound (0.802 g). $^1$H-NMR (δ ppm, DMSO-$d_6$, 400 MHz): 9.34 (d, J 2.5, 1H), 8.65 (dd, J 2.5, 9, 1H), 8.09 (d, J 9, 1H), 2.48-2.38 (m, 1H), 1.13-1.03 (m, 2H), 0.90-0.82 (m, 2H).

Intermediate 12

4-(3,5-dicyclopropyl-1H-pyrazol-1-yl)aniline

Iron powder (0.88 g, 15.8 mmol) and ammonium chloride (17 mg, 0.3 mmol) were added to a solution of intermediate 5 (0.85 g, 3.15 mmol) in EtOH/$H_2O$ (2:1, 15 mL) and the mixture refluxed for half an hour. The mixture was filtered through celite and celite washed with ethanol. Work-up ($H_2O$/AcOEt) after concentration of the combined layers afforded title compound as a yellow solid (0.68 g). $^1$H-NMR (δ ppm, DMSO-$d_6$, 400 MHz): 7.11 (d, J 8.6, 2H), 6.61 (d, J 8.6, 2H), 5.65 (s, 1H), 5.24 (s, 2H), 1.81-1.74 (m, 1H), 1.67-1.60 (m, 1H), 0.86-0.77 (m, 4H), 0.61-0.56 (m, 4H). MS (m/z): 240.3 [M+H]$^+$.

Intermediate 13

4-(3,5-dicyclopropyl-1H-pyrazol-1-yl)-3-fluoroaniline

Iron powder (1.86 g, 34.8 mmol) and ammonium chloride (30 mg, 0.7 mmol) were added to a solution of intermediate 6 (2 g, 7.0 mmol) in EtOH/H$_2$O (2:1, 30 mL) and the mixture refluxed for one hour. The mixture was filtered through celite and celite washed with ethanol. Work-up (H$_2$O/AcOEt) and concentration of the combined layers afforded title compound as a yellow solid (1.34 g).

Intermediate 14

6-(3,5-dicyclopropyl-1H-pyrazol-1-yl)pyridin-3-amine

Iron powder (0.79 g, 14.17 mmol) and ammonium chloride (15 mg, 0.28 mmol) were added to a solution of intermediate 7 (0.77 g, 2.86 mmol) in EtOH/H$_2$O (2:1, 15 mL) and the mixture refluxed for one hour. The mixture was filtered through celite and celite washed with ethanol. Work-up (H$_2$O/AcOEt) after concentration of the combined layers afforded intermediate 14 as a yellow solid (0.570 g). $^1$H-NMR (δ ppm, DMSO-d$_6$, 400 MHz): 7.75 (d, J 2.5, 1H), 7.27 (d, J 8.6, 1H), 7.06 (dd, J 2.7, 8.6, 1H), 5.67 (s, 1H), 5.43 (s, 2H), 2.39-2.27 (m, 1H), 1.88-1.74 (m, 1H), 0.90-0.72 (m, 4H), 0.69-0.50 (m, 4H).

Intermediate 15

4-[5-cyclopropyl-3-(trifluoromethyl)-1H-pyrazol-1-yl]aniline

A procedure similar to that employed for intermediate 12 was followed. From intermediate 8 (0.69 g, 2.32 mmol), EtOH—H$_2$O (2:1, 12 mL), Fe (0.64 g, 15.8 mmol) and NH$_4$Cl (0.012 mg, 0.22 mmol), the title compound was obtained as yellow solid (0.49 g). $^1$H-NMR (δ ppm, DMSO-d$_6$, 400 MHz): 7.19 (d, J 8.64, 2H), 6.65 (d, J 8.64, 2H), 6.47 (s, 1H), 5.46 (s, 2H), 1.75-1.69 (m, 1H), 0.94-0.89 (m, 2H), 0.77-0.73 (m, 2H). MS (m/z): 268.1 [M+H]$^+$.

Intermediate 16

4-[3-cyclopropyl-5-(trifluoromethyl)-1H-pyrazol-1-yl]-3-fluoroaniline

Iron powder (4.75 g, 85.1 mmol) and ammonium chloride (90 mg, 1.7 mmol) were added to a solution of intermediate 9 (5 g, 17.00 mmol) in EtOH/H$_2$O (2:1, 45 mL) and the mixture refluxed for one hour. The mixture was filtered through celite and celite washed with ethanol. Work-up (H$_2$O/AcOEt) after concentration of the combined layers afforded titled compound as a yellow solid (4.3 g). $^1$H-NMR (δ ppm, DMSO-d$_6$, 400 MHz): 7.16 (t, J 8.5, 1H), 6.50-6.45 (m, 3H), 5.86 (s, 2H), 1.60-1.51 (m, 1H), 0.91-0.82 (m, 2H), 0.76-0.69 (m, 2H).

Intermediate 17

6-[5-cyclopropyl-3-(trifluoromethyl)-1H-pyrazol-1-yl]pyridin-3-amine

Iron powder (0.279 g, 5.00 mmol) and ammonium chloride (5 mg, 0.09 mmol) were added to a solution of intermediate 10 (0.77 g, 2.86 mmol) in EtOH/H$_2$O (2:1, 9 mL) and the mixture refluxed for one hour. The mixture was filtered through celite and celite washed with ethanol. Work-up (H$_2$O/AcOEt) after concentration of the combined layers afforded intermediate 17 as a yellow solid (0.239 g). $^1$H-NMR (δ ppm, DMSO-d$_6$, 400 MHz): 7.84 (d, J 2.6, 1H), 7.33 (d, J 8.6, 1H), 7.12 (dd, J 2.6, 8.6, 1H), 6.49 (s, 1H), 5.69 (s, 2H), 2.45-2.36 (m, 1H), 0.90-0.81 (m, 2H), 0.74-0.65 (m, 2H). MS (m/z): 269.2 [M+H]$^+$.

Intermediate 18

6-[4-chloro-5-cyclopropyl-3-(trifluoromethyl)-1H-pyrazol-1-yl]pyridin-3-amine Iron powder (1.56 g, 28.0 mmol) and ammonium chloride (600 mg, 11.2 mmol) were added to a solution of intermediate 11 (1.7 g, 5.60 mmol) in EtOH/H$_2$O (2:1, 15 mL) and the mixture refluxed for one hour. The mixture was filtered through celite and celite washed with ethanol. Work-up (H$_2$O/AcOEt) and concentration of the combined layers afforded intermediate 18 as a yellow solid (1.1 g). $^1$H-NMR (δ ppm, DMSO-d$_6$, 400 MHz): 8.04 (s, 1H), 7.39 (d, J 8.2, 1H), 7.20 (d, J 8, 1H), 4.26 (s, 2H), 2.10-1.99 (m, 1H), 1.96-1.85 (m, 2H), 1.84-1.70 (m, 2H).

Intermediate 19

2-chloro-N-[4-(3,5-dicyclopropyl-1H-pyrazol-1-yl)phenyl]acetamide

Chloroacetyl chloride (0.2 mL, 2.39 mmol) was added to a solution of intermediate 12 (600 mg, 2.24 mmol) in dichloromethane (DCM) at 0° C. The mixture was stirred for 15 mins. Work-up (H$_2$O/DCM) gave the intermediate 19 which was used in the next step without further purification.

Intermediate 20

2-chloro-N-{4-[5-cyclopropyl-3-(trifluoromethyl)-1H-pyrazol-1-yl]phenyl}acetamide Chloroacetyl chloride (0.05 mL, 0.62 mmol) was added to a solution of intermediate 15 (150 mg, 0.561 mmol) in dichloromethane (DCM) at 0° C. The mixture was stirred for 15 mins. Work-up (H$_2$O/DCM) gave the titled compound, which was used in the next step without further purification.

Intermediate 21

2-chloro-N-{6-[5-cyclopropyl-3-(trifluoromethyl)-1H-pyrazol-1-yl]pyridin-3-yl}acetamide Chloroacetyl chloride (0.16 mL, 2.00 mmol) was added to a solution of intermediate 17 (500 mg, 1.86 mmol) in dichloromethane (DCM) at 0° C. The mixture was stirred for 15 mins. Work-up (H$_2$O/DCM) gave the intermediate 21 which was used in the next step without further purification.

Intermediate 22

5-cyclopropyl-1-(2-fluoro-4-iodophenyl)-3-(trifluoromethyl)-1H-pyrazole

To the intermediate 16 (1.9 g, 7.20 mmol) in 5 ml water was added Conc. HCl (5 ml) and cooled to 0° C. To this sodium nitrite solution (1 g, 15 mmol) was added slowly and stirred for 15 mins at 0° C. To this mixture potassium iodide solution (2.5 g, 15 mmol) was added at same temperature and stirred the reaction mixture at rt. Work-up (H₂O/AcOEt) and purification gave the desired product as a yellow colour liquid. ¹H-NMR (δ ppm, DMSO-d₆, 400 MHz): 8.01 (dd, J 1.7, 9.5, 1H), 7.79 (dd, J 1.7, 8.4, 1H), 7.45 (t, J 8.1, 1H), 6.63 (s, 1H), 1.64-1.56 (m, 1H), 0.92-0.84 (m, 2H), 0.79-0.71 (m, 2H).

Intermediate 23

4-[5-cyclopropyl-3-(trifluoromethyl)-1H-pyrazol-1-yl]-3-fluorobenzoic Acid

Magnesium (143 mg, 6 mmol) and a pinch of iodine suspended in ether under inert atmosphere. To this small amount of methyl iodide was added and refluxed the reaction mixture to start Grignard formation. At this stage intermediate 22 (790 mg, 2 mmol) was added and continued the reaction under reflux condition. After complete consumption of the starting material, reaction mixture cooled to rt and added dry ice pieces into it followed by 2N HCl. Solid that formed was filtered and dried on high vacuum to obtain the title compound (160 mg) as an off-white solid. ¹H-NMR (δ ppm, DMSO-d₆, 400 MHz): 13.6 (bs, 1H), 7.97-7.92 (m, 2H), 7.84-7.78 (m, 1H), 6.68 (s, 1H), 1.69-1.61 (m, 1H), 0.94-0.87 (m, 2H), 0.80-0.74 (m, 2H).

Intermediate 24

1H-benzo[d]imidazole-6-carboxylic Acid 3,4-diaminobenzoic acid (5 g, 32 mmol) and formic acid (20 ml) were mixed and refluxed overnight. Formic acid was removed on rotavapour and water added to the residue to obtain the solid. Solid was filtered and dried to obtain the title compound quantitatively.

Intermediate 25

1H-benzo[d][1,2,3]triazole-6-carboxylic Acid 3,4-diaminobenzoic acid (5 g, 32.8 mmol) was dissolved in AcOH (30 ml) and this mixture cooled to 5° C. To this mixture NaNO2 solution (2.7 g in 8 ml water) was added followed by 2 ml sulphuric acid. Reaction mixture was allowed to stir for 90 mins. After that, reaction mixture quenched with ice and solid that obtained was filtered and washed with water to obtain the title compound (4.5 g) as a brown solid.

Intermediate 26

Quinoline-6-carboxylic Acid

Sulphuric acid (67.5 ml) was added to 4-Aminophenylacetic acid (45 g, 297 mmol), glycerol (61.7 g, 67 mmol), and iodine (1.14 g, 4 mmol) drop-wise at rt. The mixture was heated to 140° C. for 5 h. After that reaction mixture quenched with ice and solid that formed was filtered Solid was dissolved in MeOH and charcoal was added to it and refluxed for 1 h. This mixture was filtered through celite and methanol was removed to obtain the title compound (7 g) as a brown solid.

Intermediate 27

Quinoxaline-6-carboxylic Acid 3,4 diamino benzoic acid (500 mg, 3.29 mmol) was added to aqueous potassium carbonate (7 ml, 1.82 g K₂CO₃) slowly. Then glyoxal bis(sodium sulphite) adduct hydrate (963 mg, 3.62 mmol) added slowly. This mixture heated to 80° C. for 5 h to obtain a clear solution. After completion of reaction, reaction mixture added to dil HCl slowly and solid that formed was filtered and dried to obtain the title compound as a brown solid (300 mg).

Intermediate 28

Ethyl 2-(imidazo[1,2-a]pyridin-2-yl)acetate 2-aminopyridine (500 mg, 5.31 mmol) and ethyl chloroacetoacetate (870 mg, 5.31 mmol) were dissolved in DMSO and heated to 100° C. for 1 h under inert atmosphere. After 1 h, water added to reaction mixture followed by Work-up (H₂O/AcOEt) and purification on 60-120 mesh silicagel using AcOEt and petroleum ether (30:70) gave the title compound (110 mg) as a brown liquid. ¹H-NMR (δ ppm, CDCl₃, 400 MHz): 8.06 (d, J 6.7, 1H), 7.59 (s, 1H), 7.55 (d, J 9.4, 1H), 7.14 (t, J 7.9, 1H), 6.75 (t, J 6.7, 1H), 4.12 (q, J 7.1, 2H), 3.87 (s, 2H), 1.3 (t, J 7.1, 3H).

Intermediate 29

2-(imidazo[1,2-a]pyridin-2-yl)acetic Acid

Intermediate 28 (7.5 g, 39.22 mmol) was dissolved in water (30 ml) and added NaOH (2.35 g, 58.8 mmol). This mixture was heated to 90° C. for 1 h. After that, water removed by distillation and acidified the reaction mixture with dil HCl to pH 7 to obtain the solid. Solid was filtered and dried on vacuum to obtain the title compound as a brown solid quantitatively. ¹H-NMR (δ ppm, CDCl₃, 400 MHz): 8.50 (d, J 6.7, 1H), 7.82 (s, 1H), 7.46 (d, J 9, 1H), 7.20 (t, J 7.5, 1H), 6.85 (t, J 6.7, 1H), 3.69 (s, 2H).

Intermediate 30

2-(quinolin-6-yl)acetic Acid

Sulphuric acid (67.5 ml) was added to 4-Aminophenylacetic acid (45 g, 297 mmol), glycerol (61.7 g, 67 mmol), and iodine (1.14 g, 4 mmol) drop-wise at rt. The mixture was heated to 140° C. for 24 h. After that reaction mixture cooled to rt and pH adjusted to 5 using 10% sodium hydroxide solution. To this methanol (350 ml) and sulphuric acid (3 ml) was added and heated to 100° C. for 24 h. Reaction mixture filtered through celite and filtrate was evaporated on rotavapour to obtain the residue. pH of the residue was adjusted to 5 using 4% NaOH solution and extracted with EtOAc. EtOAc layer was dried on anhydrous Na₂SO₄ and EtOAc removed on rotavapour to obtain the crude. Crude was purified by column using EtOAc and Petether as eluent to obtain methyl-2-(quinolin-6-yl)acetate (11.2 g). Methyl-2-(quinolin-6-yl)acetate (11.2 g) was dissolved in Methanol (8 ml) and water (8 ml) and added sodium hydroxide (3.3 g, 82 mmol). This mixture stirred for 30 mins and methanol removed on rotavapour to obtain the residue. Residue was acidified to pH 5 using 0.8 N HCl to obtain the solid. Solid was filtered and dried to obtain the title compound (8.2 g).

Intermediate 31

2-(3-nitropyridin-2-ylamino)acetic Acid

2-Chloro-3-nitropyridine (5 g, 31.5 mmol) was dissolved in EtOH (125 ml), added potassium carbonate (4.35 g, 31.5 mmol) and to this mixture glycine (4.73 g, 6.3 mmol) in 25 ml water was added and refluxed for overnight. The reaction mixture cooled to 0° C. to obtain the solid. Then EtOH was removed on rotavapour and acidified with 2N HCl and solid filtered and dried on vacuum to obtain the title compound quantitatively as a yellow solid.

Intermediate 32

2-(3-aminopyridin-2-ylamino)acetic Acid

Iron powder (14.15 g, 0.25 mol) and ammonium chloride (5.41 g, 101.47 mmol) were added to a solution of intermediate 31 (10 g, 50.74 mmol) in EtOH/H$_2$O (2:1, 225 mL) and the mixture refluxed for one hour. The mixture was filtered through celite and celite washed with ethanol. Work-up (H$_2$O/AcOEt) and concentration of the combined layers afforded title compound (10 g) as a brown solid.

Intermediate 33

2-(3H-[1,2,3]triazolo[4,5-b]pyridin-3-yl)acetic Acid

Intermediate 32 (10.92 g, 65.35 mmol) was dissolved in 30 ml water and 13 ml AcOH was added. To this mixture sodium nitrite (4.96 g, 71.88 mmol) solution was added at rt and mixture was cooled to 0° C. The reaction mixture stirred for 30 mins and filtered the reaction mixture. Solid that obtained was dried under vacuum to obtain the title compound (7.5 g) as a red solid.

Intermediate 34

(R)-2-(3-nitropyridin-2-ylamino)propanoic Acid

2-Chloro-3-nitropyridine (500 mg, 3.15 mmol) was dissolved in EtOH (12.5 ml), added potassium carbonate (435 mg, 3.15 mmol) and to this mixture (S)-2-aminopropanoic acid (561 mg, 6.3 mmol) in 2.5 ml water was added and refluxed for overnight. Reaction mixture cooled to 0° C. to obtain the solid. Then EtOH was removed on rotavapour and acidified with 2N HCl and solid filtered and dried on vacuum to obtain the title compound (460 mg) as an yellow solid.

Intermediate 35

(R)-2-(3-aminopyridin-2-ylamino)propanoic Acid

Iron powder (657 mg, 11.78 mmol) and ammonium chloride (251 mg, 53.4 mmol) were added to a solution of intermediate 34 (500 mg, 2.35 mmol) in EtOH/H$_2$O (2:1, 12 mL) and the mixture refluxed for one hour. The mixture was filtered through celite and celite washed with ethanol. Work-up (H$_2$O/AcOEt) and concentration of the combined layers afforded title compound (600 mg) as a black solid.

Intermediate 36

(R)-2-(3H-[1,2,3]triazolo[4,5-b]pyridin-3-yl)propanoic Acid

Intermediate 35 (600 mg, 3.3 mmol) was dissolved in 1.5 ml water and 0.5 ml AcOH was added. To this mixture sodium nitrite ((190 mg, 2.76 mmol) solution was added at rt and mixture was cooled to 0° C. The reaction mixture stirred for 30 mins and then filtered. The resulting solid was dried under vacuum to obtain the title compound (160 mg) as a red solid.

$^1$H-NMR (δ ppm, DMSO-d$_6$, 400 MHz): 11.04 (s, 1H), 8.18-8.17 (m, 1H), 7.51-7.40 (m, 2H), 5.30 (q, J 7.12, 1H), 1.18 (d, J 7.12, 3H).

Intermediate 37 methyl 2-(quinolin-6-yl)propanoate

THF (5 ml) was taken in a RBF, diisopropyl amine (0.19 ml, 1.29 mmol) was added and cooled to −78° C. under nitrogen atmosphere. Then n-BuLi (0.8 ml, 1.29 mmol) was added and stirred at same temperature for 30 mins. At this stage methyl 2-(quinolin-6-yl)acetate (0.2 g, 0.99 mmol) was added and stirred at −78° C. for 30 mins. Then methyl iodide (0.17 g, 1.2 mmol) was added and stirred at −78° C. for 30 mins and then slowly brought to rt. At rt the reaction mixture was allowed to stir overnight. The reaction mixture was quenched with water and extracted with EtOAc. The organic layer dried on anhydrous Na$_2$SO$_4$ and EtOAc removed using a rotary evaporator to obtain the crude product, which was purified by column chromatography on 60-120 mesh silica gel and EA and Petether (25:75) as eluent. $^1$H-NMR (δ ppm, CDCl$_3$, 400 MHz): 8.89-8.86 (m, 1H), 8.13 (d, J 7.8, 1H), 8.07 (d, J 8.7, 1H), 7.76-7.64 (m, 2H), 7.42-7.37 (m, 1H), 3.92 (q, J 7.2, 1H), 3.68 (s, 3H), 1.60 (d, J 7.2, 3H).

Intermediate 38

2-(quinolin-6-yl)propanoic Acid

Intermediate 37 (440 mg, 2.04 mmol) was dissolved in MeOH (5 ml), added water (2 ml) and lithium hydroxide (427 mg, 10.2 mmol). This mixture was refluxed for 2 hrs and cooled the reaction mixture. Methanol was removed on rotavapour and to the residue 6 N HCl was added to adjust the pH to 7. The solid that obtained was filtered and dried to obtain the title compound as a solid.

Intermediate 39 quinolin-6-ylmethanamine

6-Cyano quinoline (14 gms) [Synthesized as per Srivastava, Rajiv et al, Synthetic Communications 37 (3), 431-438, 2007], ammonical methanol (250 ml), raney nickel (20 gms) were mixed and kept under hydrogen atmosphere (50-60 Psi) for 4 h at 40-45° C. After completion of the reaction, reaction mixture was filtered through celite, and celite bed washed with MeOH. Filtrate was concentrated to give the title compound (13.5 g) as a black syrupy liquid.

General Procedure for Amide Formation

Procedure-1:
A solution of an appropriate aniline (1 eq.), the requisite acid (1.1 eq.), EDC.HCl (1.2 eq.), HOBt (0.5 eq.) and TEA (3 eq.) in DMF was stirred at RT overnight. Work-up (H$_2$O/AcOEt) and purification gave the desired product.
Procedure-2:
Acid (1 eq.) was dissolved in DCM, cooled to 0° C., added oxalyl chloride (3 eq.) and three drops of DMF. The reaction mixture was stirred at room temperature for 30 mins and DCM was removed on rotavapour to obtain the acid chloride. Amine was dissolved in DCM under N$_2$ atmosphere and added Pyridine (1.3 eq). To this mixture acid chloride in DCM was added and allowed to stir at room temperature until amine was totally consumed. Work-up (H₂O/AcOEt) and purification gave the desired product.

The following compounds were prepared using these procedures:

Example 1

N-[4-(3,5-dicyclopropyl-1H-pyrazol-1-yl)phenyl]-1H-benzo[d]imidazole-6-carboxamide Following the general procedure-1, the title compound (160 mg) was prepared from intermediate 24 (97 mg, 0.60 mmol) and intermediate 12 (120 mg, 0.50 mmol) as an off-white solid. M. P.: 170-176° C. $^1$H-NMR (δ ppm, DMSO-$d_6$, 400 MHz): 12.74 (bs, 1H), 10.37 (s, 1H), 8.37 (s, 1H), 8.30 (s, 1H), 7.93 (d, J 8.84, 2H), 7.87-7.84 (m, 1H), 7.69 (d, J 8.48, 1H), 7.55 (d, J 8.84, 2H), 5.79 (s, 1H), 1.86-1.76 (m, 2H), 0.94-0.90 (m, 2H), 0.89-0.82 (m, 2H), 0.69-0.62 (m, 4H). MS (m/z): 382.17. [M−H]⁻.

Example 2

N-[4-(3,5-dicyclopropyl-1H-pyrazol-1-yl)phenyl]-1H-benzo[d][1,2,3]triazole-6-carboxamide Following the general procedure-1, the title compound (30 mg) was prepared from intermediate 25 (97 mg, 0.59 mmol) and intermediate 12 (120 mg, 0.50 mmol) as a white solid. M. P.: 240-246° C. $^1$H-NMR (δ ppm, DMSO-$d_6$, 400 MHz): 16.02 (bs, 1H), 10.55 (s, 1H), 8.6 (bs, 1H), 8.06-7.98 (m, 2H), 7.92 (d, J 8.8, 2H), 7.57 (d, J 8.8, 2H), 5.80 (s, 1H), 1.84-1.78 (m, 2H), 0.93-0.82 (m, 4H), 0.69-0.62 (m, 4H). MS (m/z): 383.21 [M−H]⁻.

Example 3

N-[4-(3,5-dicyclopropyl-1H-pyrazol-1-yl)phenyl]quinoline-6-carboxamide hydrochloride Following the general procedure-1, N-[4-(3,5-dicyclopropyl-1H-pyrazol-1-yl)phenyl]quinoline-6-carboxamide (60 mg) was prepared from intermediate 26 (95 mg, 0.55 mmol) and intermediate 12 (120 mg, 0.5 mmol) as a pale yellow solid and dissolved in THF. Saturated HCl in diethyl ether was added at 0° C. to this solution and stirred for 15 min. Solid that separated out was filtered and dried to give the title compound (46 mg) as a white solid. M. P. 114-119° C. $^1$H-NMR (δ ppm, DMSO-$d_6$, 400 MHz): 11.00 (s, 1H), 9.34 (d, J 3.8, 1H), 9.18 (d, J 8.2, 1H), 9.00 (s, 1H), 8.59 (d, J 8.8, 1H), 8.48 (d, J 8.8, 1H), 8.15-8.05 (m, 1H), 7.61 (d, J 8.9, 2H), 7.61 (d, J 8.9, 2H), 5.84 (s, 1H), 1.89-1.77 (m, 2H), 0.95-0.84 (m, 4H), 0.70-0.64 (m, 4H). MS (m/z): 393.05 [M−H−HCl]⁻.

Example 4

N-[4-(3,5-dicyclopropyl-1H-pyrazol-1-yl)phenyl]quinoxaline-6-carboxamide

Following the general procedure-1, the title compound (48 mg) was prepared from intermediate 27 (104 mg, 0.574 mmol) and intermediate 12 (120 mg, 0.50 mmol) as a white solid. M. P.: 162-167° C. $^1$H-NMR (δ ppm, DMSO-$d_6$, 400 MHz): 10.77 (s, 1H), 9.08-9.06 (br. d, J 4.7, 2H), 8.77 (d, J 1.7, 1H), 8.36 (d, J 1.9, 1H), 8.24 (d, J 8.76, 1H), 7.96 (d, J 8.84, 2H), 7.59 (d, J 8.84, 2H), 5.81 (s, 1H), 1.88-1.77 (m, 2H), 0.95-0.90 (m, 2H), 0.87-0.82 (m, 2H), 0.69-0.62 (m, 4H). MS (m/z): 394. [M−H]⁻.

Example 5

2-(1H-benzo[d]imidazol-1-yl)-N-[4-(3,5-dicyclopropyl-1H-pyrazol-1-yl)phenyl]acetamide Intermediate 19 (130 mg, 0.41 mmol) and benzimidazole (53 mg, 0.45 mmol) were dissolved in DMF (5 mL) at 0° C. and Sodium Hydride (28.35 mg, 1.23 mmol) was added to the reaction mixture. Then reaction was allowed to stir at ambient temperatures for overnight. Work-up (H₂O:AcOEt) followed by purification on column afforded the title compound (40 mg) as a white solid. M. P. 230-235° C. $^1$H-NMR (δ ppm, DMSO-$d_6$, 400 MHz): 10.61 (s, 1H), 8.23 (s, 1H), 7.70-7.65 (m, 3H), 7.54-7.51 (m, 3H), 7.26-7.18 (m, 2H), 5.78 (s, 1H), 5.19 (s, 2H), 1.86-1.71 (m, 2H), 0.92-0.80 (m, 4H), 0.68-0.59 (m, 4H). MS (m/z): 396.07 [M−H]⁻.

Example 6

2-(1H-benzo[d][1,2,3]triazol-1-yl)-N-[4-(3,5-dicyclopropyl-1H-pyrazol-1-yl)phenyl]acetamide Following the general procedure-1, the title compound (100 mg) was prepared from 2-(1H-benzo[d][1,2,3]triazol-1-yl)acetic acid (177 mg, 0.60 mmol) and intermediate 12 (120 mg, 0.50 mmol) as an off-white solid. M. P.: 216-220° C. $^1$H-NMR (δ ppm, DMSO-$d_6$, 400 MHz): 10.75 (s, 1H), 8.07 (d, J 8.4, 1H), 7.85 (d, J 8.4, 1H), 7.69 (d, J 8.84, 2H), 7.58-7.52 (m, 3H), 7.44-7.40 (m, 1H), 5.78 (s, 1H), 5.71 (s, 2H), 1.85-1.80 (m, 2H), 0.90-0.80 (m, 4H), 0.66-0.60 (m, 4H). MS (m/z): 396.93 [M−H]⁻.

Example 7

N-[4-(3,5-dicyclopropyl-1H-pyrazol-1-yl)phenyl]-2-(1H-indol-3-yl)acetamide

The title compound (160 mg) was prepared from 2-(1H-indol-3-yl)acetic acid (104 mg, 0.6 mmol) and intermediate 12 (120 mg, 0.500 mmol) as a white solid. M. P. 158-164° C. $^1$H-NMR (δ ppm, DMSO-$d_6$, 400 MHz): 10.90 (s, 1H), 10.23 (s, 1H), 7.70 (d, J 8.8, 2H), 7.60 (d, J 7.8, 1H), 7.47 (d, J 8.8, 2H), 7.34 (d, J 8.0, 1H), 7.26-7.25 (d, J 1.9, 1H), 7.06 (t, J 7.4, 1H), 6.97 (t, J 7.3, 1H), 5.76 (s, 1H), 3.74 (s, 2H), 1.84-1.80 (m, 1H), 1.79-1.71 (m, 1H), 0.89-0.79 (m, 4H), 0.65-0.59 (m, 4H). MS (m/z): 395.25 [M−H]⁻.

Example 8

N-[4-(3,5-dicyclopropyl-1H-pyrazol-1-yl)phenyl]-2-(imidazo[1,2-a]pyridin-2-yl)acetamide Hydrochloride Following the general procedure-1, N-[4-(3,5-dicyclopropyl-1H-pyrazol-1-yl)phenyl]-2-(imidazo[1,2-a]pyridin-2-yl)acetamide (56 mg) was prepared from intermediate 29 (79 mg, 0.45 mmol) and intermediate 12 (90 mg, 0.38 mmol) as a brown solid and dissolved in THF. Saturated HCl in diethyl ether was added to this solution at 0° C. and stirred for 15 min. Solid that separated out was filtered and dried to give the title compound (54 mg) as a pale-brown solid. M. P. 92-97° C. $^1$H-NMR (δ ppm, DMSO-$d_6$, 400 MHz): 10.82 (s, 1H), 8.92 (d, J 6.7, 1H), 8.32 (s, 1H), 7.97-7.92 (m, 2H), 7.75 (d, J 8.7, 2H), 7.53 (d, J 8.7, 2H), 7.52-7.47 (m, 1H), 5.79 (s, 1H), 3.80 (s, 2H), 1.87-1.71 (m, 2H), 0.93-0.79 (m, 4H), 0.69-0.58 (m, 4H). MS (m/z): 398.24 [M+H–HCl]$^+$.

Example 9

N-[4-(3,5-dicyclopropyl-1H-pyrazol-1-yl)phenyl]-2-(quinolin-6-yl)acetamide

Following the general procedure-1, the title compound (45 mg) was obtained from intermediate 30 (93 mg, 0.49 mmol) and intermediate 12 (100 mg, 0.42 mmol) as a brown solid. M. P.: 171-177° C. $^1$H-NMR (δ ppm, DMSO-d$_6$, 400 MHz): 10.41 (s, 1H), 8.86-8.85 (m, 1H), 8.34 (d, J 8.26, 1H), 7.98 (d, J 8.64, 1H), 7.89 (s, 1H), 7.76-7.70 (m, 3H), 7.52-7.48 (m, 3H), 5.77 (s, 1H), 3.88 (s, 2H), 1.84-1.78 (m, 1H), 1.77-1.70 (m, 1H), 0.90-0.80 (m, 4H), 0.65-0.59 (m, 4H). MS (m/z): 409.38 [M+H]$^+$.

Example 10

N-[4-(3,5-dicyclopropyl-1H-pyrazol-1-yl)phenyl]-2-(quinolin-6-yl)acetamide hydrochloride Example 9 (200 mg, 0.48 mmol) was dissolved in saturated HCl in diethyl ether at 0° C. and stirred for 15 min. Solid that separated out was filtered and dried to give the title compound (140 mg, 65% yield) as a brown solid. M. P.: 152-158° C. $^1$H-NMR (δ ppm, DMSO-d$_6$, 400 MHz): 10.78 (s, 1H), 9.26 (m, 1H), 9.16 (d, J 8.3, 1H), 8.36 (d, J 8.8, 1H), 8.29 (s, 1H), 8.17-8.15 (m, 1H), 8.08-8.04 (m, 1H), 7.75 (d, J 8.9, 2H), 7.50 (d, J 8.9, 2H), 5.79 (s, 1H), 4.04 (s, 2H), 1.85-1.70 (m, 2H), 0.89-0.81 (m, 4H), 0.66-0.60 (m, 4H). MS (m/z): 443.01 [M–H]$^-$.

Example 11

2-(1H-benzo[d][1,2,3]triazol-1-yl)-N-(4-(3,5-dicyclopropyl-1H-pyrazol-1-yl)-3-fluorophenyl)acetamide Following the general procedure-1, the title compound (29 mg) was prepared from 2-(1H-benzo[d][1,2,3]triazol-1-yl) acetic acid (133 mg, 0.75 mmol) and intermediate 13 (120 mg, 0.47 mmol) as a pale-yellow solid. M. P.: 201-203° C. $^1$H-NMR (δ ppm, DMSO-d$_6$, 400 MHz): 11.0 (s, 1H), 8.07 (d, J 8.4, 1H), 7.85 (d, J 8.4, 1H), 7.74 (dd, J 2, 12.5, 1H), 7.56 (t, J 7.4, 1H), 7.47 (t, J 8.4, 1H), 7.43-7.40 (m, 2H), 5.74 (s, 2H), 1.86-1.80 (m, 1H), 1.55-1.44 (m, 2H), 0.90-0.74 (m, 4H), 0.62-0.54 (m, 4H). MS (m/z): 417.28 [M+H]$^+$.

Example 12

N-[4-(3,5-dicyclopropyl-1H-pyrazol-1-yl)-3-fluorophenyl]-2-(quinolin-6-yl)acetamide Hydrochloride Following the general procedure-1, N-[4-(3,5-dicyclopropyl-1H-pyrazol-1-yl)-3-fluorophenyl]-2-(quinolin-6-yl)acetamide (95 mg) was prepared from intermediate 13 (200 mg, 0.78 mmol) and intermediate 30 (232 mg, 1.2 mmol) as an yellow solid and dissolved in THF. Saturated HCl in diethyl ether was added to this solution at 0° C. and stirred for 15 min. Solid that separated out was filtered and dried to give the title compound (50 mg) as an yellow solid. M. P.: 106.8-108.2° C. $^1$H-NMR (δ ppm, DMSO-d$_6$, 400 MHz): 10.99 (s, 1H), 9.24 (d, J 4.5, 1H), 9.09 (d, J 8.0, 1H), 8.32-8.25 (m, 2H), 8.12 (d, J 8.6, 1H), 8.05-8.01 (m, 1H), 7.83 (d, J 11.3, 1H), 7.50-7.41 (m, 2H), 5.73 (s, 1H), 4.07 (s, 2H), 1.84-1.76 (m, 1H), 1.52-1.42 (m, 1H), 0.82-0.74 (m, 4H), 0.62-0.52 (m, 4H). MS (m/z): 427.10 [M+H]$^+$.

Example 13

N-[6-(3,5-dicyclopropyl-1H-pyrazol-1-yl)pyridin-3-yl]quinoline-6-carboxamide Dihydrochloride Following the general procedure-1, N-[6-(3,5-dicyclopropyl-1H-pyrazol-1-yl)pyridin-3-yl]quinoline-6-carboxamide (71 mg) was prepared from intermediate 26 (103 mg, 0.59 mmol) and intermediate 14 (120 mg, 0.49 mmol) as an orange solid and dissolved in THF. Saturated HCl in diethyl ether was added to this solution at 0° C. and stirred for 15 min. Solid that separated out was filtered and dried to give the title compound (62 mg) as an yellow solid. M. P. 232-238° C. $^1$H-NMR (δ ppm, DMSO-d$_6$, 400 MHz): 11.09 (s, 1H), 9.25 (d, J 4.0, 1H), 9.02 (d, J 7.3, 1H), 8.93 (d, J 8.4, 2H), 8.53 (d, J 9.0, 1H), 8.43-8.36 (m, 2H), 8.02-7.95 (m, 1H), 7.78 (d, J 8.8, 1H), 5.83 (s, 1H), 2.74-2.65 (m, 1H), 1.93-1.84 (m, 1H), 1.00-0.80 (m, 4H), 0.74-0.58 (m, 4H). MS (m/z): 393.94 [M–H–2HCl]$^-$.

Example 14

N-[6-(3,5-dicyclopropyl-1H-pyrazol-1-yl)pyridin-3-yl]quinoxaline-6-carboxamide

Following the general procedure-1, title compound (117 mg) was prepared from intermediate 27 (104 mg, 0.59 mmol) and intermediate 14 (120 mg, 0.49 mmol) as a brown solid M. P. 193-198° C. $^1$H-NMR (δ ppm, DMSO-d$_6$, 400 MHz): 10.98 (s, 1H), 9.08 (dd, J 1.6, 5.8, 2H), 8.91 (d, J 2.4, 1H), 8.81 (d, J 1.6, 1H), 8.40-8.36 (m, 2H), 8.25 (d, J 8.7, 1H), 7.77 (d, J 8.7, 1H), 5.83 (s, 1H), 2.75-2.61 (m, 1H), 1.94-1.81 (m, 1H), 0.98-0.82 (m, 4H), 0.70-0.55 (m, 4H). MS (m/z): 397.22 [M+H–HCl]$^+$.

Example 15

2-(1H-benzo[d][1,2,3]triazol-1-yl)-N-[6-(3,5-dicyclopropyl-1H-pyrazol-1-yl)pyridin-3-yl]acetamide Following the general procedure-1, title compound (250 mg) was prepared from intermediate 14 (200 mg, 0.84 mmol) and 2-(1H-benzo[d][1,2,3]triazol-1-yl)acetic acid (237 mg, 1.34 mmol) as an orange solid M. P.: 130.1-132.8° C. $^1$H-NMR (δ ppm, DMSO-d$_6$, 400 MHz): 10.92 (s, 1H), 8.64 (d, J 2.6, 1H), 8.13 (dd, J 2.6, 8.9, 1H), 8.07 (d, J 8.4, 1H), 7.86 (d, J 8.4, 1H), 7.70 (d, J 8.9, 1H), 7.56 (t, J 7.6, 1H), 7.44 (t, J 7.6, 1H), 5.81 (s, 1H), 5.74 (s, 2H), 2.70-2.60 (m, 1H), 1.90-1.80 (m, 1H), 0.93-0.83 (m, 4H), 0.70-0.58 (m, 4H). MS (m/z): 400.28 [M+H–HCl]$^+$.

Example 16

N-[6-(3,5-dicyclopropyl-1H-pyrazol-1-yl)pyridin-3-yl]-2-(quinolin-6-yl)acetamidedihydrochloride Following the general procedure-1, N-[6-(3,5-dicyclopropyl-1H-pyrazol-1-yl)pyridin-3-yl]-2-(quinolin-6-yl)acetamide (138 mg) was prepared from intermediate 30 (112 mg, 0.59 mmol) and intermediate 14 (120 mg, 0.49 mmol) as a pale yellow solid and dissolved in THF. Saturated HCl in diethyl ether was added to this solution at 0° C. and stirred for 15 min. Solid that separated out was filtered and dried to give the title compound (34 mg) as an off-white solid. M. P. 62-67° C. $^1$H-NMR (δ ppm, DMSO-d$_6$, 400 MHz): 10.86 (s, 1H), 9.21 (d, J 4.4, 1H), 9.04 (d, J 8.1, 1H), 8.69 (s, 1H), 8.30-8.22 (m, 2H), 8.18 (d, J 8.1, 1H), 8.09 (d, J 8.4, 1H), 8.00-7.97 (m, 1H), 7.68 (d, J 8.8, 1H), 5.80 (s, 1H), 4.05 (s, 2H), 2.69-2.55 (m, 1H), 1.89-1.75 (m, 1H), 0.97-0.78 (m, 4H), 0.70-0.50 (m, 4H). MS (m/z): 410.26 [M+H−2HCl]$^+$.

Example 17

N-{4-[5-cyclopropyl-3-(trifluoromethyl)-1H-pyrazol-1-yl]phenyl}quinoline-6-carboxamide hydrochloride Following general procedure-1, N-{4-[5-cyclopropyl-3-(trifluoromethyl)-1H-pyrazol-1-yl]phenyl}quinoline-6-carboxamide (35 mg) was prepared from intermediate 26 (85 mg, 0.49 mmol) and intermediate 15 (120 mg, 0.45 mmol) as a brown solid (35 mg) and dissolved THF. Saturated HCl in diethyl ether was added to the solution at 0° C. and stirred for 15 min. Solid that separated out was filtered and dried to give the title compound (30 mg) as an yellow solid. M. P. 188-192° C. $^1$H-NMR (δ ppm, DMSO-d$_6$, 400 MHz): 10.86 (s, 1H), 9.15 (d, J 4, 1H), 8.80-8.78 (m, 2H), 8.39 (d, J 8.8, 1H), 8.26 (d, J 8.8, 1H), 8.04 (d, J 8.8, 2H), 7.83-7.80 (m, 1H), 7.67 (d, J 8.8, 2H), 6.62 (s, 1H), 1.89-1.84 (m, 1H), 1.00-0.96 (m, 2H), 0.84-0.80 (m, 2H). MS (m/z): 457.16 [M−H]$^-$.

Example 18

N-{4-[5-cyclopropyl-3-(trifluoromethyl)-1H-pyrazol-1-yl]phenyl}quinoxaline-6-carboxamide Following the general procedure-1, the title compound (60 mg) was prepared from intermediate 27 (78 mg, 0.44 mmol) and intermediate 15 (110 mg, 0.411 mmol) as a pale yellow solid. M. P. 205-209° C. $^1$H-NMR (δ ppm, DMSO-d$_6$, 400 MHz): 10.87 (s, 1H), 9.08-9.05 (m, 2H), 8.79 (d, J 1.6, 1H), 8.36 (dd, J 1.8, 8.7, 1H), 8.25 (d, J 8.72, 1H), 8.05 (d, J 8.84, 2H), 7.67 (d, J 8.8, 2H), 6.62 (s, 1H), 1.88-1.84 (m, 1H), 0.99-0.96 (m, 2H), 0.84-0.81 (m, 2H). MS (m/z): 422.03 [M−H]$^-$.

Example 19

2-(1H-benzo[d]imidazol-1-yl)-N-{4-[5-cyclopropyl-3-(trifluoromethyl)-1H-pyrazol-1-yl]phenyl}acetamide Intermediate 20 (180 mg, 0.523 mmol) and benzimidazole were dissolved in DMF (3 mL) at 0° C. and Sodium Hydride (37.7 mg, 1.57 mmol) was added to the reaction mixture. Then reaction was allowed to stir at ambient temperature overnight. Work-up (H$_2$O:AcOEt) followed by purification on column afforded the title compound as a white solid. M. P. 178-184° C. $^1$H-NMR (δ ppm, DMSO-d$_6$, 400 MHz): 10.72 (s, 1H), 8.23 (s, 1H), 7.77 (d, J 8.8, 2H), 7.66 (d, J 7.72, 1H), 7.59 (d, J 8.8, 2H), 7.54 (d, J 7.72, 1H), 7.26-7.18 (m, 2H), 6.59 (s, 1H), 5.21 (s, 2H), 1.82-1.78 (m, 1H), 0.96-0.92 (m, 2H), 0.81-0.77 (m, 2H). MS (m/z): 424.04 [M−H]$^-$.

Example 20

2-(1H-benzo[d][1,2,3]triazol-1-yl)-N-{4-[5-cyclopropyl-3-(trifluoromethyl)-1H-pyrazol-1-yl]phenyl}acetamide Intermediate 20 (150 mg, 0.44 mmol) and benzotriazole (52 mg, 0.44 mmol) were dissolved in DMF (3 mL) at 0° C. and Sodium Hydride (31.5 mg, 1.30 mmol) was added to the reaction mixture. Then reaction was allowed to stir at ambient temperatures for overnight. Work-up (H$_2$O:AcOEt) followed by purification on column afforded the title compound (60 mg) as a white solid. M. P. 200-204° C. $^1$H-NMR (δ ppm, DMSO-d$_6$, 400 MHz): 10.86 (s, 1H), 8.07 (d, J 8.4, 2H), 7.86 (d, J 8.4, 2H), 7.77 (d, J 8.8, 1H), 7.60 (d, J 8.8, 1H), 7.59-7.54 (m, 1H), 7.44-7.40 (m, 1H), 6.60 (s, 1H), 5.73 (s, 2H), 1.83-1.77 (m, 1H), 0.97-0.92 (m, 2H), 0.79-0.75 (m, 2H). MS (m/z): 425.02 [M−H]$^-$.

Example 21

2-(2H-benzo[d][1,2,3]triazol-2-yl)-N-{4-[5-cyclopropyl-3-(trifluoromethyl)-1H-pyrazol-1-yl]phenyl}acetamide Intermediate 20 (500 mg, 1.45 mmol) and benzotriazole (173 mg, 1.45 mmol) were dissolved in DMF (10 mL) at 0° C. and Sodium Hydride (31.5 mg, 1.30 mmol) was added to the reaction mixture. Then reaction was allowed to stir at ambient temperatures for overnight. Work-up (H$_2$O:AcOEt) followed by purification on column afforded the title compound (60 mg) as a white solid. M. P. 188-192° C. $^1$H-NMR (δ ppm, DMSO-d$_6$, 400 MHz): 10.85 (s, 1H), 7.95 (dd, J 2.8, 6.4, 2H), 7.77 (d, J 8.7, 2H), 7.61 (d, J 8.7, 2H), 7.45 (dd, J 2.8, 6.4, 2H), 6.60 (s, 1H), 5.74 (s, 2H), 1.86-1.78 (m, 1H), 0.99-0.91 (m, 2H), 0.83-0.76 (m, 2H). MS (m/z): 425.14. [M−H]$^-$.

Example 22

2-(3H-[1,2,3]triazolo[4,5-b]pyridin-3-yl)-N-{4-[5-cyclopropyl-3-(trifluoromethyl)-1H-pyrazol-1-yl]phenyl}acetamide Following the general procedure-2, the title compound (20 mg) was prepared from intermediate 15 (500 mg, 1.9 mmol) and intermediate 33 (442 mg, 2.2 mmol) as a white solid. M. P.: 206-209° C. $^1$H-NMR (δ ppm, DMSO-d$_6$, 400 MHz): 10.98 (s, 1H), 7.83 (dd, J 1.4, 4.8, 1H), 7.71 (d, J 8.9, 2H), 7.60 (d, J 8.9, 2H), 7.35 (dd, J 1.4, 8, 1H), 7.20-7.15 (m, 1H), 6.61 (s, 1H), 4.50 (s, 2H), 1.85-1.76 (m, 1H), 1.00-0.92 (m, 2H), 0.82-0.76 (m, 2H). MS (m/z): 468.71 [M+CH$_3$CN]$^+$.

Example 23

(S)-2-(3H-[1,2,3]triazolo[4,5-b]pyridin-3-yl)-N-{4-[5-cyclopropyl-3-(trifluoromethyl)-1H-pyrazol-1-yl]phenyl}propanamide Following the general procedure-2, the title compound (20 mg) was prepared from intermediate 15 (180 mg, 0.67 mmol) and intermediate 36 (170 mg, 0.81 mmol) as a pale-yellow solid. M. P.: 186-191° C. $^1$H-NMR (δ ppm, DMSO-d$_6$, 400 MHz): 11.02 (s, 1H), 7.86 (dd, J 1.3, 4.8, 1H), 7.72 (d, J 8.8, 2H), 7.60 (d, J 8.8, 2H), 7.38 (dd, J 1.3, 8, 1H), 7.22-7.14 (m, 1H), 6.60 (s, 1H), 4.94 (q, J 7.2, 1H), 1.89-1.79 (m, 1H), 1.29 (d, J 7.2, 3H), 1.00-0.92 (m, 2H), 0.82-0.74 (m, 2H). MS (m/z): 482.78 [M+CH$_3$CN]$^+$.

Example 24

2-(6-amino-9H-purin-9-yl)-N-{4-[5-cyclopropyl-3-(trifluoromethyl)-1H-pyrazol-1-yl]phenyl}acetamide Adenine (233 mg, 1.76 mmol) was dissolved in DMF (10 ml) and added potassium carbonate (298 mg, 2.2 mmol)

stirred at rt for 30 mins. Intermediate 15 (233 mg, 1.8 mmol) was added to this reaction mixture and stirred at rt for 2 h. After completion of the reaction, water added to reaction mixture and extracted with AcOEt. AcOEt layer was dried on anhydrous sodium sulphate and AcOEt removed on rotavapour to obtain the crude. Crude was purified by column using DCM:MeOH (98:2) as eluent to obtain the titled compound as a white solid. M. P.: 249.3-251.7° C. $^1$H-NMR (δ ppm, DMSO-$d_6$, 400 MHz): 10.73 (s, 1H), 8.12 (d, J 8.12, 2H), 7.76 (d, J 8.8, 2H), 7.59 (d, J 8.8, 2H), 7.23 (s, 2H), 6.60 (s, 1H), 5.10 (s, 2H), 1.85-1.76 (m, 1H), 1.00-0.90 (m, 2H), 0.82-0.74 (m, 2H). MS (m/z): 440.71 [M−H]$^-$.

Example 25

N-(4-(5-cyclopropyl-3-(trifluoromethyl)-1H-pyrazol-1-yl)phenyl)-2-(1,3-dimethyl-2,6-dioxo-2,3-dihydro-1H-purin-7(6H)-yl)acetamide Following the general procedure-1, the title compound (77 mg) was prepared from theophylline-7-acetic acid (117 mg, 0.49 mmol) and intermediate 15 (120 mg, 0.45 mmol) as a pale yellow solid. M. P. 178-184° C. $^1$H-NMR (δ ppm, DMSO-$d_6$, 400 MHz): 10.66 (s, 1H), 8.07 (s, 1H), 7.75 (d, J 8.9, 2H), 7.59 (d, J 8.9, 2H), 6.59 (s, 1H), 5.23 (s, 2H), 3.45 (s, 3H), 3.19 (s, 3H), 1.83-1.77 (m, 1H), 0.98-0.91 (m, 2H), 0.85-0.76 (m, 2H). MS (m/z): 486.20 [M−H]$^-$.

Example 26

N-{4-[5-cyclopropyl-3-(trifluoromethyl)-1H-pyrazol-1-yl)phenyl)-2-(imidazo[1,2-a]pyridin-2-yl)acetamide Hydrochloride Following the general procedure-1, N-{4-[5(3)-cyclopropyl-3(5)-(trifluoromethyl)-1H-pyrazol-1-yl)phenyl)-2-(imidazo[1,2-a]pyridin-2-yl)acetamide was prepared from intermediate 29 (71 mg, 0.40 mmol) and intermediate 15 (90 mg, 0.34 mmol) as a brown solid and dissolved in THF. Saturated HCl in diethyl ether was added to this solution at 0° C. and stirred for 15 min. Solid that separated out was filtered and dried to give the title compound (79 mg) as a white solid. M. P. 294-299° C. $^1$H-NMR (δ ppm, DMSO-$d_6$, 400 MHz): 10.85 (s, 1H), 8.90 (d, J 6.5, 1H), 8.30 (s, 1H), 7.97-7.88 (m, 2H), 7.82 (d, J 8.7, 2H), 7.61 (d, J 8.7, 2H), 7.47 (t, J 5.6, 1H), 6.61 (s, 1H), 4.16 (s, 2H), 1.84-1.79 (m, 1H), 0.98-0.90 (m, 2H), 0.64-0.49 (m, 2H). MS (m/z): 426.27 [M+H−HCl]$^+$.

Example 27

N-{4-[5-cyclopropyl-3-(trifluoromethyl)-1H-pyrazol-1-yl]phenyl}-2-(quinolin-6-yl)acetamide Hydrochloride Following the general procedure-1, N-{4-[3-cyclopropyl-5-(trifluoromethyl)-1H-pyrazol-1-yl]phenyl}-2-(quinolin-6-yl)acetamide (95 mg) was prepared from intermediate 30 (92 mg, 0.49 mmol) and intermediate 15 (120 mg, 0.45 mmol) as an off-white solid. This amide was dissolved in saturated HCl in diethyl ether at 0° C. and stirred for 15 min. Solid that separated out was filtered and dried to give the title compound (80 mg) as an off-white solid. M. P. 248-254° C. $^1$H-NMR (δ ppm, DMSO-$d_6$, 400 MHz): 10.75 (s, 1H), 9.17 (d, J 4.4, 1H), 8.95 (d, J 8.2, 1H), 8.24-8.19 (m, 1H), 8.05 (d, J 8.6, 1H), 7.94-7.91 (m, 1H), 7.82 (d, J 8.7, 2H), 7.57 (d, J 8.7, 2H), 6.59 (s, 1H), 4.03 (s, 2H), 1.79-1.75 (m, 1H), 0.96-0.91 (m, 2H), 0.80-0.77 (m, 2H). MS (m/z): 435 [M−H−HCl]$^-$.

Example 28

N-{4-[5-cyclopropyl-3-(trifluoromethyl)-1H-pyrazol-1-yl]phenyl}-2-(quinolin-6-yl)propanamide Hydrochloride Following the general procedure-1, N-{4-[5-cyclopropyl-3-(trifluoromethyl)-1H-pyrazol-1-yl]phenyl}-2-(quinolin-6-yl)propanamide (74 mg) was prepared from intermediate 15 (150 mg, 0.56 mmol) and intermediate 38 (180 mg, 0.89 mmol) as a brown solid and dissolved in THF. Saturated HCl in diethyl ether was added to this solution at 0° C. and stirred for 15 min. Solid that separated out was filtered and dried to give the title compound (45 mg) as a brown solid. M. P.: 168-170° C. $^1$H-NMR (δ ppm, DMSO-$d_6$, 400 MHz): 10.61 (s, 1H), 9.11 (d, J 3.7, 1H), 8.87 (d, J 8, 1H), 8.18 (d, J 9, 2H), 8.07 (dd, J 1.6, 8.8, 1H), 7.85 (dd, J 4.9, 8.3, 1H), 7.79 (d, J 8.9, 2H), 7.55 (d, J 8.9, 2H), 6.59 (s, 1H), 4.20 (q, J 6.8, 1H), 1.80-1.70 (m, 1H), 1.57 (d, J 6.8, 3H), 1.00-0.90 (m, 2H), 0.80-0.70 (m, 2H). MS (m/z): 451.11 [M+H−HCl]$^-$.

Example 29

N-{4-[5-cyclopropyl-3-(trifluoromethyl)-1H-pyrazol-1-yl]-3-fluorophenyl}-1H-benzo[d][1,2,3]triazole-6-carboxamide Following the general procedure-2, the title compound (30 mg) was prepared from intermediate 16 (150 mg, 0.53 mmol) and intermediate 25 (114 mg, 0.63 mmol) as a white solid. M. P.: 235-237° C. $^1$H-NMR (δ ppm, DMSO-$d_6$, 400 MHz): 10.84 (s, 1H), 8.66 (s, 1H), 8.07 (dd, J 2.2, 12.7, 1H), 8.02 (s, 2H), 7.79 (dd, J 1.8, 8.7, 1H), 7.66 (t, J 8.6, 1H), 6.62 (s, 1H), 1.68-1.60 (m, 1H), 0.96-0.88 (m, 2H), 0.81-0.75 (m, 2H). MS (m/z): 428.84 [M−H]$^-$.

Example 30

2-(1H-benzo[d][1,2,3]triazol-1-yl)-N-{4-[5-cyclopropyl-3-(trifluoromethyl)-1H-pyrazol-1-yl]-3-fluorophenyl}acetamide Following the general procedure-1, the title compound (145 mg) was prepared from 2-(1H-benzo[d][1,2,3]triazol-1-yl)acetic acid (112 mg, 0.80 mmol) and intermediate 16 (300 mg, 1.14 mmol) as a white solid M. P.: 197-202° C. $^1$H-NMR (δ ppm, DMSO-$d_6$, 400 MHz): 11.09 (s, 1H), 8.07 (d, J 8.4, 1H), 7.86 (d, J 8.4, 1H), 7.81 (dd, J 2, 12.4, 1H), 7.63 (t, J 8.6, 1H), 7.57 (t, J 7.7, 1H), 7.50-7.48 (m, 1H), 7.42 (t, J 7.8, 1H), 6.60 (s, 1H), 5.75 (s, 2H), 1.64-1.52 (m, 1H), 0.92-0.84 (m, 2H), 0.78-0.69 (m, 2H). MS (m/z): 442.69 [M−H]$^-$.

Example 31

N-{6-[5-cyclopropyl-3-(trifluoromethyl)-1H-pyrazol-1-yl]pyridin-3-yl}-1H-benzo[d][1,2,3]triazole-5-carboxamide Following the general procedure-1, the title compound (43 mg) was prepared from intermediate 17 (200 mg, 0.75 mmol) and intermediate 25 (194 mg, 1.2 mmol) as a white solid. M. P.: 235.6-238.4° C. $^1$H-NMR (δ ppm, DMSO-$d_6$, 400 MHz): 10.86 (s, 1H), 8.99 (d, J 2.5, 1H), 8.68 (bs, 1H), 8.48 (dd, J 2.6, 8.8, 1H), 8.08-8.01 (m, 2H), 7.82 (d, J 8.8, 1H), 6.65 (s, 1H), 2.58-2.50 (m, 1H), 1.04-0.98 (m, 2H), 0.82-0.74 (m, 2H). MS (m/z): 413.89 [M+H]+.

Example 32

2-(1H-benzo[d][1,2,3]triazol-1-yl)-N-{6-[5-cyclopropyl-3-(trifluoromethyl)-1H-pyrazol-1-yl]pyridin-3-yl}acetamide Intermediate 21 (200 mg, 0.58 mmol) and benzotriazole (69 mg, 0.58 mmol) were dissolved in DMF (10 mL) at 0° C. and Sodium Hydride (41.0 mg, 1.74 mmol) was added to the reaction mixture. Then reaction was allowed to stir at ambient temperatures for overnight. Work-up ($H_2O$:AcOEt) followed by purification on column afforded the title compound (60 mg) as a white solid. M. P. 189-192° C. $^1$H-NMR (δ ppm, DMSO-$d_6$, 400 MHz): 11.07 (s, 1H), 8.76 (d, J 2.1, 1H), 8.25 (dd, J 2.3, 8.8 1H), 8.07 (d, J 8.3, 1H), 7.87 (d, J 8.3, 1H), 7.78 (d, J 8.8, 1H), 7.57 (t, J 7.6, 1H), 7.42 (t, J 7.6, 1H), 6.62 (s, 1H), 5.77 (s, 2H), 2.40-2.30 (m, 1H), 1.00-0.90 (m, 2H), 0.80-0.70 (m, 2H). MS (m/z): 426.13 [M–H]−.

Example 33

2-(2H-benzo[d][1,2,3]triazol-2-yl)-N-{6-[5-cyclopropyl-3-(trifluoromethyl)-1H-pyrazol-1-yl]pyridin-3-yl}acetamide Intermediate 21 (200 mg, 0.58 mmol) and benzotriazole (69 mg, 0.58 mmol) were dissolved in DMF (10 mL) at ° C. and Sodium Hydride (41.0 mg, 1.74 mmol) was added to the reaction mixture. Then reaction was allowed to stir at ambient temperatures for overnight. Work-up ($H_2O$:AcOEt) followed by purification on column afforded the title compound (60 mg) as a white solid. M. P. 193-198° C. $^1$H-NMR (δ ppm, DMSO-$d_6$, 400 MHz): 11.06 (s, 1H), 8.75 (d, J 2.4, 1H), 8.25 (dd, J 2.5, 8.8, 1H), 7.98-7.92 (m, 2H), 7.78 (d, J 8.8, 1H), 7.50-7.44 (m, 2H), 6.62 (s, 1H), 5.78 (s, 2H), 2.58-2.40 (m, 1H), 1.00-0.90 (m, 2H), 0.80-0.71 (m, 2H). MS (m/z): 425.99 [M–H]−.

Example 34

N-{6-[5-cyclopropyl-3-(trifluoromethyl)-1H-pyrazol-1-yl]pyridin-3-yl}-2-(quinolin-6-yl)acetamide hydrochloride Following the general procedure-1, N-{6-[5-cyclopropyl-3-(trifluoromethyl)-1H-pyrazol-1-yl]pyridin-3-yl}-2-(quinolin-6-yl)acetamide (67 mg) was prepared from intermediate 30 (133 mg, 0.71 mmol) and intermediate 17 (120 mg, 0.45 mmol) as a pale yellow solid and dissolved in THF. Saturated HCl in diethyl ether was added to this solution at 0° C. and stirred for 15 min. Solid that separated out was filtered and dried to give the title compound (63 mg) as a white solid. M. P. 225-230° C. $^1$H-NMR (δ ppm, DMSO-$d_6$, 400 MHz): 10.96 (s, 1H), 9.15 (d, J 4.4, 1H), 8.90 (d, J 8.0, 1H), 8.80 (d, J 2.3, 1H), 8.30 (dd, J 2.4, 8.8, 1H), 8.21 (d, J 8.7, 1H), 8.18 (s, 1H), 8.03 (d, J 8.3, 1H), 7.90 (dd, J 5, 8.2, 1H), 7.75 (d, J 8.8, 1H), 6.61 (s, 1H), 4.06 (s, 2H), 2.51-2.40 (m, 1H), 1.01-0.90 (m, 2H), 0.81-0.70 (m, 2H). MS (m/z): 436.02 [M–H–2HCl]−.

Example 35

2-(1H-benzo[d][1,2,3]triazol-1-yl)-N-{6-[4-chloro-5-cyclopropyl-3-(trifluoromethyl)-1H-pyrazol-1-yl]pyridin-3-yl}acetamide Following the general procedure-1, the title compound (97 mg) was prepared from 2-(1H-benzo[d][1,2,3]triazol-1-yl) acetic acid (123 mg, 0.68 mmol) and intermediate 18 (120 mg, 0.43 mmol) as a brown solid. M. P.: 182.5-189.3° C. $^1$H-NMR (δ ppm, DMSO-$d_6$, 400 MHz): 11.13 (s, 1H), 8.78 (d, J 2.4, 1H), 8.27 (dd, J 2.6, 8, 1H), 8.07 (d, J 8.4, 1H), 7.87 (d, J 8.4, 1H), 7.75 (d, J 8.7, 1H), 7.6 (t, J 7.3, 1H), 7.4 (t, J 7.5, 1H), 5.78 (s, 2H), 2.20-2.08 (m, 1H), 0.92-0.84 (m, 2H), 0.70-0.59 (m, 2H). MS (m/z): 459.8 [M–H]−.

Example 36

4-[5-cyclopropyl-3-(trifluoromethyl)-1H-pyrazol-1-yl]-3-fluoro-N-(quinolin-6-ylmethyl)benzamide hydrochloride Following the general procedure-2,4-[5-cyclopropyl-3-(trifluoromethyl)-1H-pyrazol-1-yl]-3-fluoro-N-(quinolin-6-ylmethyl)benzamide (83 mg) was prepared from intermediate 23 (200 mg, 0.67 mmol) and intermediate 39 (188 mg, 0.60 mmol) as a white solid and dissolved in THF. Saturated HCl in diethyl ether was added to this solution at 0° C. and stirred for 15 min. Solid that separated out was filtered and dried to give the title compound (70 mg) as an off-white solid. M. P.: 156-159° C. $^1$H-NMR (δ ppm, DMSO-$d_6$, 400 MHz): 9.61 (t, J 5.7, 1H), 9.15 (d, J 4.2, 1H), 8.95 (d, J 8.4, 1H), 8.25 (d, J 8.8, 1H), 8.17 (s, 1H), 8.07-8.03 (m, 2H), 7.98 (d, J 8.3, 1H), 7.93-7.90 (m, 1H), 7.84 (t, J 7.8, 1H), 6.68 (s, 1H), 4.75 (d, J 5.7, 2H), 1.72-1.61 (m, 1H), 0.97-0.88 (m, 2H), 0.81-0.74 (m, 2H). MS (m/z): 455.03 [M+H–HCl]+.

Example 37

1-[4-(3,5-dicyclopropyl-1H-pyrazol-1-yl)phenyl]-3-(quinolin-6-yl)urea 6-amino quinoline (200 mg, 0.88 mmol), triphosgene (156 mg, 0.53 mmol) and triethyl amine (0.4 ml, 3.5 mmol) were dissolved in DCM and stirred at rt for 30 mins under nitrogen atmosphere. After that intermediate 12 (200 mg, 0.88 mmol) was added and mixture was heated to 40° C. for 40 hrs. After that $CHCl_3$ (10 ml) and 0.2 M citric acid (2.5 mL) was added to reaction mixture and the aqueous phase was removed. Organic layer washed with brine and dried on anhydrous $Na_2SO_4$. Organic layer was removed on rotavapour to obtain the crude. Crude was purified by column chromatography using 60-120 mesh silica gel and DCM and MeOH (98:2) as eluent to obtain the titled compound (25 mg) as a brown solid. M. P.: 102-104° C. $^1$H-NMR (δ ppm, DMSO-$d_6$, 400 MHz): 9.07 (s, 1H), 8.96 (s, 1H), 8.73 (dd, J 1.6, 4.2, 1H), 8.23 (d, J 7.9, 1H), 8.17 (d, J 2.2, 1H), 7.94 (d, J 9.0 1H), 7.71 (dd, J 2.4, 9.1, 1H), 7.59 (d, J 8.9, 2H), 7.48 (d, J 8.9, 2H), 7.47-7.43 (m, 1H), 5.77 (s, 1H), 1.88-1.71 (m, 2H), 0.90-0.82 (m, 4H), 0.70-0.58 (m, 4H). MS (m/z): 410.44 [M+H]+

Biological Assays

The properties of the compounds of this invention may be confirmed by a number of biological/pharmacological assays. The biological/pharmacological assay which can be been carried out with the compounds according to the invention and/or their pharmaceutically acceptable salts is exemplified below. Similarly the compounds of the present invention may also be tested using other assays, such as cytokine (IL-2, IL-4, IL-5, IL-10, IL-12, TNF alpha, interferon gamma etc.) estimation in Jurkat as well as human PBMCs. The compounds of the invention may also be tested in various aminal models to establish the various therapeutic potential of the compounds of this invention.

1. In-Vitro CRAC Channel Inhibition Assays
1A. In-Vitro CRAC Channel Inhibition Assay in Jurkat Cells Inhibition of CRAC channels was determined following thapsigargin (Sigma, Cat # T9033) induced endoplasmic calcium release in Jurkat cells. (see Yasurio Yonetoky et. al Bio. & Med. Chem. 14 (2006) 4750-4760). Cells were centrifuged and resuspended in equal volumes ° f $Ca^{2+}$ and $Mg^{2+}$ free Hanks buffer and Fluo-8 NW dye (ABD Bioquest, Inc., Sunnyvale, Calif.) loading solution at $2\times10^5$ cells/100 µl/well in 96-well black plate. Plate is incubated at 37° C./5% $CO_2$ for 30 mM followed by further 15 mM incubation at room temperature. Test compounds (DMSO stocks diluted in $Ca^{2+}$ and $Mg^{2+}$ free Hanks buffer) at desired concentrations were added to the wells and incubated for 15 mM. Thapsigargin (1 µM final concentration) was added to the wells and incubated for 15 min to inhibit the Sarco-endoplasmic reticulum $Ca^{2+}$ ATPase pump thereby depleting endoplasmic calcium and raising cytosolic calcium concentrations. Store-operated calcium entry was initiated by adding extracellular $Ca^{2+}$ to a final concentration of 1.8 mM. Fluorescence was monitored over 5 mM on a plate reader (BMG Labtech., Germany) with excitation at 485 nm and an emission wavelength at 520 nm. Data were analyzed using GraphPad Prism. $IC_{50}$ for each compound was determined based on the percent inhibition of thapsigargin-induced calcium influx into cells. The results are as provided in Table 1A.

TABLE 1A

| Compound | % inhibition (1 uM) | IC50 (nM) |
| --- | --- | --- |
| Example 1 | 57.6 | — |
| Example 2 | 78 | 182.5 |
| Example 3 | 100 | — |
| Example 4 | 85 | — |
| Example 5 | 88.51 | 383.1 |
| Example 6 | 94.6 | 51.31 |
| Example 7 | 36.83 | — |
| Example 8 | 17.90 | — |
| Example 9 | 100 | — |
| Example 10 | 100 | 146.7 |
| Example 11 | 78.56 | — |
| Example 12 | 100 | 263.2 |
| Example 13 | 22.37 | — |
| Example 14 | 17.80 | — |
| Example 15 | 3.93 | — |
| Example 16 | 30.81 | — |
| Example 17 | 94.03 | 86.12 |
| Example 18 | 96.64 | 53.36 |
| Example 19 | 69.53 | — |
| Example 20 | 100 | 39.17 |
| Example 21 | 83.03 | 139.0 |
| Example 22 | 30.86 | — |
| Example 23 | 69.87 | — |
| Example 24 | 14.77 | — |
| Example 25 | 39.07 | — |
| Example 26 | 30.86 | — |
| Example 27 | 100 | — |
| Example 28 | 0 | — |
| Example 29 | 81.1 | — |
| Example 30 | 100 | 160.5 |
| Example 31 | 50.62 | — |
| Example 32 | 41.23 | — |
| Example 33 | 49.54 | — |
| Example 34 | 51.21 | — |

TABLE 1A-continued

| Compound | % inhibition (1 uM) | IC50 (nM) |
| --- | --- | --- |
| Example 35 | 15 | — |
| Example 36 | 51.04 | — |
| Example 37 | 57.28 | — |

1B. In-Vitro CRAC Channel Inhibition Assay in NCI-H460 Cancer Cell Line

Inhibition of CRAC channels was determined following thapsigargin (Sigma, Cat # T9033) induced endoplasmic calcium release in NCI-H460 cells (National Centre For Cell Science (NCCS), Pune).

Cells (30,000 per well) were plated overnight in complete RPMI medium. Medium was substituted with $Ca^{2+}$ and $Mg^{2+}$ free Hanks buffer and Fluo-8 NW dye (ABD Bioquest, Inc., Sunnyvale, Calif.) loading solution in 96-well black plate. Plate was incubated at 37° C./5% $CO_2$ for 30 min followed by further 15 mM incubation at room temperature. Test compounds (DMSO stocks diluted in $Ca^{2+}$ and $Mg^{2+}$ free Hanks buffer) at desired concentrations were added to the wells and incubated for 15 min. Thapsigargin (1 µM final concentration) was added to the wells and incubated for 15 min to inhibit the Sarco-endoplasmic reticulum $Ca^{2+}$ ATPase pump thereby depleting endoplasmic calcium and raising cytosolic calcium concentrations. Store-operated calcium entry was initiated by adding extracellular $Ca^{2+}$ to a final concentration of 2.5 mM. Fluorescence was monitored over 30 mM on a plate reader (BMG Labtech., Germany) with excitation at 485 nm and an emission wavelength at 520 nm. Data were analyzed using GraphPad Prism. $IC_{50}$ for each compound was determined based on the percent inhibition of Thapsigargin-induced calcium influx into cells. The results are as provided in Table 2.

1C. In-Vitro Cell Proliferation Assay in NCI-H460 Cancer Cell Line (Anticancer Activity)

Growth inhibition assays were carried out using 10% FBS supplemented media. Cells were seeded at a concentration of 5000 cells/well in a 96-well plate. Test compound at a concentration range from 0.01 to 10000 nM were added after 24 h. Growth was assessed using the 3-[4,5-dimethylthiazol-2-yl]-2,5-diphenyltetrazolium bromide (MTT) dye reduction test at 0 h (prior to the addition of the test compound) and 48 h after the addition of test compound. Absorbance was read on a Fluostar Optima (BMG Labtech, Germany) at a wave length of 450 nm. Data were analysed using GraphPad Prism. IC-50 for each compound was determined based on the % inhibition due to the test compound compared to the control. The results are as provided in Table 2.

For methods of cell proliferation assay, see, for example, Mosmann. T., *Journal of Immunological Methods*, 65(1-2), 55-63, (1983).

TABLE 2

| | NCI-H460 Cell Ca assay | | NCI-H460 Cell line assay | |
| --- | --- | --- | --- | --- |
| Compound | % inhibition @ 1 µM | IC 50 nM | % inhibition @ 10 µM | GI 50 nM |
| Example 2 | 91.14 | — | 34 | — |
| Example 3 | 100 | — | — | 261.1 |
| Example 4 | 80.66 | — | 41 | — |
| Example 5 | — | 79.87 | — | 177.2 |
| Example 9 | — | — | — | 270.3 |
| Example 10 | — | 72.65 | — | — |
| Example 12 | — | — | 90 | 100.3 |
| Example 17 | 100 | — | — | 710.2 |
| Example 19 | — | — | 83.6 | 148.4 |
| Example 24 | — | — | 84.4 | — |
| Example 27 | 98.10 | — | — | 358.3 |

TABLE 2-continued

|  | NCI-H460 Cell Ca assay | | NCI-H460 Cell line assay | |
|---|---|---|---|---|
| Compound | % inhibition @ 1 µM | IC 50 nM | % inhibition @ 10 µM | GI 50 nM |
| Example 29 | — | — | 100 | 1524 |
| Example 34 | — | — | 82.72 | 627.8 |

2. In Vitro Inhibition of Cytokine Release in Jurkat Cells, Human Whole Blood and Peripheral Blood Mononuclear Cells (PBMC).

Inhibition of cytokine IL-2, IL-4, IL-5 and TNF α was determined as described below.

a. Inhibition of IL-2 in Jurkat Cells

Cells were incubated with desired concentrations of the inhibitor for 15 min. Cytokine release was induced by the addition of Concanavalin A (25 µg/ml)+Phorbol Myristate Acetate (50 ng/ml) for IL-2 & TNFα or with Phytohemagglutinin (5 µg/ml) for IL-4 & IL-5 and incubated at 37° C. in an atmosphere containing 95% $CO_2$. Supernatant was collected after 20 h (IL-2 & TNFα) or 48 h (IL-4 & IL-5) for estimation of cytokines by ELISA. Data were analysed using GraphPad Prism. $IC_{50}$ values for each compound were determined based on the percent inhibition due to the test compound compared to the control.

b. Inhibition of Cytokine Release in Human Whole Blood (HWB):

Freshly collected HWB was diluted with RPMI medium (1:4.5) and added to a 96-well plate. Wells were incubated with desired concentrations of the inhibitor for 15 min. Cytokine release was induced by the addition of Concanavalin A (25 µg/ml)+Phorbol Myristate Acetate (50 ng/ml) for IL-2 & TNFα or with Phytohemagglutinin (5 µg/ml) for IL-4 & IL-5 and incubated at 37° C. in an atmosphere containing 95% $CO_2$. Supernatant was collected after 20 h (IL-2 & TNFα) or 48 h (IL-4 & IL-5) for estimation of cytokines by ELISA. Data were analysed using GraphPad Prism. $IC_{50}$ values for each compound were determined based on the percent inhibition due to the test compound compared to the control.

c. Inhibition of Cytokine Release in PBMC:

PBMC from freshly collected HWB were isolated by density gradient using Histopaque and seeded in a 96-well plate. Cells were incubated with desired concentrations of the inhibitor for 15 min. Cytokine release was induced by the addition of Concanavalin A (25 µg/ml)+Phorbol Myristate Acetate (50 ng/ml) for IL-2 & TNFα or with Phytohemagglutinin (5 µg/ml) for IL-4 & IL-5 and incubated at 37° C. in an atmosphere containing 95% $CO_2$. Supernatant was collected after 20 h (IL-2 & TNFα) or 48 h (IL-4 & IL-5) for estimation of cytokines by ELISA. Data were analysed using GraphPad Prism. $IC_{50}$ values for each compound were determined based on the percent inhibition due to the test compound compared to the control. The results are as provided in Table 3.

TABLE 3

| | IC 50 Values in nM | | | | | | | | |
|---|---|---|---|---|---|---|---|---|---|
| | Jurkat | Human Whole Blood | | | | PBMC | | | |
| Compound | IL-2 | IL-2 | TNFα | IL-5 | IL-4 | IL-2 | TNFα | IL-5 | IL-4 |
| Prednisolone | 35.48 | 77.25 | — | — | — | 3.72 | — | — | — |
| Example 2 | — | 102.1 | 147.6 | — | — | — | — | — | — |
| Example 6 | — | 52.24 | 164.7 | — | — | — | — | — | — |
| Example 20 | — | 40.74 | 35.58 | 163.5 | 1227 | 383.4 | 138.0 | 149.2 | 539.6 |
| Example 27 | — | 125.2 | 117.5 | — | — | — | — | — | — |

Anti Cancer Activity

The correlation of CRAC and STIM protein and its use for this invention may be confirmed by a number of biological/pharmacological assays. The biological/pharmacological assays which may be been carried out according to the invention are exemplified below.

Compound A, 2-(1H-benzo[d]imidazol-1-yl)-N-(4-(5-cyclopropyl-3-(trifluoromethyl)-1H-pyrazol-1-yl)phenyl)acetamide, and Compound B, N-(4-(3,5-dicyclopropyl-1H-pyrazol-1-yl)phenyl)-2-(quinolin-6-yl)acetamide were used as CRAC channel inhibitors for the biological assay.

Example I

Expression of Orai1 & Stim1 in AS49 and NCI-H460 Cells

Orai1 and Stim1 expression in non-small cell lung cancer cell lines was confirmed by PCR (polymerase chain reaction). Briefly, $5 \times 10^6$ cells treated with desired concentrations of the test article were harvested, pelleted, and resuspended in 1 ml TRI Reagent (Sigma, St. Louis, Mo.) and total RNA was extracted as per the manufacturer's instructions. cDNA was prepared using the First Strand cDNA synthesis and amplified using the following primer pairs:

```
Orai1: Forward 5' CATGGTGGCAATGGTGGAGGTG 3'
Reverse 5' AGGCACTGAAGGCGATGAGCA 3'

Orai2: Forward 5' ATGGTGCCATGGTGGAGGT 3'
Reverse 5' TGCAGGCGCTGAAGGCAAT 3'

Orai3: Forward 5' AAGCTCAAAGCTTCCAGCCGC 3'
Reverse 5' GGTGGGTACTCGTGGTCACTCT 3'

Stim1: Forward 5' AAGGCTCTGGATACAGTGCTCTTT 3'
Reverse 5' AGCATGAAGTCCTTGAGGTGATTAT 3'

Stim2: Forward 5' ACGACACTTCCCAGGATAGCA 3'
Reverse 5' GACTCCGGTCACTGATTTTCAAC 3'
```

See, e.g., Peel et. al., Respiratory Research, 7,119, 2006; Gwack et. al., J. Biol. Chem., 282,16232-16243, 2006.

Bands were resolved by agarose gel electrophoresis and visualized using SYBR safe DNA gel stain. The results are shown in FIG. 1.

Example-II

In Vitro CRAC Channel Inhibition Assay in NCI-H460 Cancer Cell Line

Inhibition of CRAC channels was determined following thapsigargin (Sigma, Cat # T9033) induced endoplasmic calcium release in NCI-H460 cells (National Centre For Cell Science (NCCS), Pune).

For Methodology Refer 1B.

Compound A showed 100% inhibition at 1 uM with an $IC_{50}$ value of less than 200 nM. See FIG. 2.

Example III

In Vitro Cell Proliferation Assay in NCI-H460 Cancer Cell Line (Anticancer Activity)

The effect of CRAC and/or STIM protein on the proliferation and viability of lung cancer cells was determined as follows.

For Methodology Refer 1C.

Compound A showed 100% inhibition at 1 uM with a $GI_{50}$ value of less than 200 nM (See FIG. 3).

Example IV

Effect of Compound B on Expression of Orai and Stim Expression in NCI-H460 Cells Orai and Stim expressions were measured using the methodology described in Example 1 above in NCI-H460 cells but with 1 and 10 μM of compound B.

The data showed the NCI-H460 cells expressed Orai1, Orai3, Stim1 and Stim2. The mRNA expression of Orai1, Stim1, and Stim2 was significantly reduced upon treating the cells with Compound B as evident by qualitative PCR. See FIG. 4.

Example V

Determination of Cytotoxicity in NCI-H460 Cells

Cytotoxicity of a test compound (Compound B) was determined using a lactate dehydrogenase assay kit (Cayman Chemicals, MI) as per the manufacturer's instructions with some minor modifications. Briefly, 20,000 cells/well in complete RPMI-1640 media were seeded in a 96-well tissue culture plate and incubated overnight at 37° C. and 5% $CO_2$. The test compound was added to the wells in triplicate at the desired concentrations. Doxorubicin and/or 1% Triton-X were used as a positive control. After 48 h, the media was removed and assayed for lactate dehydrogenase in a colorimetric assay. Optical density was measured on a microplate reader (BMG Labtech., Germany) at 490 nM. Data were analyzed using Graphpad Prism (Graphpad software; San Diego Calif.).

The data indicated that the Compound B was not cytotoxic in the NCI-H460 cell line, as evidenced by undetectable levels of lactate dehydrogenase in the media.

Example VI

Evaluation of Anti-Tumor Efficacy in Female Balb/c Nude Mice Bearing NCI-H460 Human Non-Small Cell Lung Cancer Xenografts A subcutaneous xenograft lung carcinoma model was used to evaluate the anti-tumor efficacy of test compounds. Taxol was used as the positive control. The model was established by the transplantation of NCI-H460 cells ($5\times10^6$) subcutaneously on the right flank of each animal (0.1 mL/mouse). When the average tumor volume reached around 170 $mm^3$, 30 nude mice were selected based on tumor volume and randomly assigned into six animals per treatment group. Animals were orally administered 30 mg/kg of the test compound (Compound A) BID for 15 days. During the treatment period, the implanted tumors were measured by caliper three times a week in a blind fashion. The tumors were measured for the maximum width (X) and length (Y) and the tumor volumes (V) were calculated using the formula: $V=(X^2Y)/2$. The animal body weights were also measured at the same time. Data were analyzed using Graphpad Prism (Graphpad software; San Diego Calif.).

Administration of the test compound resulted in a 32% reduction in tumor growth without any significant change in body weight. A 36% reduction in tumor growth with significant reduction of body weight was observed in animals treated by intravenous administration of taxol. See FIG. 5.

Example VII

Evaluation of Usefulness of CRAC Channel Modulators in Various Anti-Inflammatory and Autoimmune Disorders Using In-Vivo Animal Models i. Concanavalin (Con) a Induced Hepatitis in Female Balb/C Mice:

Con A is often used to prepare experimental animals with high levels of cytotoxic T-lymphocytes, because these cells are involved in the development of viral infections in humans. In this model, animals are administered test compounds orally 1 hour prior to intravenous administration of Con A. Blood samples are collected after 24 hours for determination of Serum glutamic oxaloacetic transaminase (SGOT) and Serum glutamic pyruvic transaminase (SGPT) in serum.

% reduction in serum SGOT & SGPT upon administration of the test compound can be studied.

ii. TNCB Induced Contact Hypersensitivity in Female Balb/c Mice:

Contact hypersensitivity is a simple in vivo assay of cell-mediated immune function. In this procedure, exposure of epidermal cells to exogenous haptens results in a delayed type hypersensitive reaction that can be measured and quantified. Briefly, 7% TNCB solution is applied to the abdominal region of 8 week old Balb/c mice. Ear thickness is measured 7 days after TNCB sensitization. Compounds are administered orally followed by an application of 1% TNCB to inside and outside of ear pinnae. Ear thickness is measured 24 h after TNCB challenge % reduction in ear inflammation upon administration of the test compound can be studied.

iii. Foot Paw Delayed Type Hypersensitivity in Male Balb/c Mice:

DTH swelling responses can be used to follow the activity of immunosuppressive molecules and/or suppressor T cells in vivo. Intradermal antigen (methylated BSA) injections are given to mice (at base of tail) on day 0 and day 7. Compounds are administered once daily from day 0 to day 10 Methylated BSA is injected into the right hind footpad of animals on day 10. Weight difference induced by antigen is determined by weighing the right and left hind paws 24 h after injection of methylated BSA (day 11).

% reduction in antigen-induced paw inflammation in mice can be studied.

iv. OVA-Induced Asthma in Guinea Pigs:

Pulmonary eosinophilia and airway remodelling in conjunction with altered neural control of airway tone and airway epithelial desquamation contributes to Airway Hyper-responsiveness (AHR) in asthma. For determination of eosinophil reduction, animals are sensitized with OVA on d0, d7, and d14 followed by another round (0.1% w/v) through inhalation on d19 & d20. Compounds are administered orally 1 h before OVA challenge (0.3%). BAL fluid is collected on d22 for differential count and cytokine estimation. For determination of change in respiratory parameters, animals are subjected to whole body plethysmography immediately after ova challenge. % reduction in blood eosinophils along with a concurrent improvement in respiration upon administration of the test compound can be studied.

v. Collagen-Induced Arthritis in Male DBA/1 Ola HSD Mice:

Collagen induced arthritis in rodent models have been widely used to illustrate and understand the development of the disease besides serving as a surrogate for validation of therapeutic targets for human rheumatoid arthritis. Mice were anesthetized with Isoflurane and given 150 μl of Bovine Type II collagen in Freund's complete adjuvant injections (day 0 and day 21). Treatment is initiated on study day 0 and continued once daily, every day (po, qd). Starting on day 18, clinical scores are given daily for each of the paws (right front, left front, right rear, left rear) and continued till the day of sacrifice (day 34). Daily administration of the test compound at to alleviates arthritic symptoms, disease progression, and incidence by % compared to the control animals can be studied.

Other in-vivo models wherein the effect of CRAC channel modulators in various Anti-inflammatory and Autoimmune disorders can be tested include Chronic Experimental Autoimmune Encephalomyelitis in C57/B16.1 mice: Experimental Autoimmune Encephalomyelitis (EAE) is an inflammatory disease of the central nervous system and widely used as an animal model of Multiple Sclerosis. Animals are administered pertussis toxin intravenously and myelin oligodendrocyte glycoprotein (MOG) subcutaneously on day 0. Treatment is initiated at day 0 and continued till sacrifice. Development of EAE is observed between day 9 to day 42. At the end of the treatment period, animals are sacrificed for histopathological analysis as well as cytokine estimation in plasma.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as described in the specification and the claims.

All publications and patent and/or patent applications cited in this application are herein incorporated by reference to the same extent as if each individual publication or patent application was specifically and individually indicated to be incorporated herein by reference.

We claim:

1. A method of treating non-small cell lung cancer comprising administering to a subject in need thereof an effective amount of a compound of formula (I)

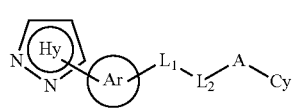

or a tautomer, N-oxide, pharmaceutically acceptable ester or pharmaceutically acceptable salt thereof, wherein
Ring Hy represents

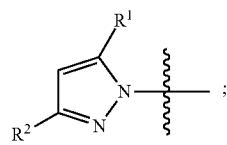

$R^1$ and $R^2$ are the same or different and are independently selected from $CH_3$, $CH_2F$, $CHF_2$, $CF_3$, substituted or unsubstituted $C_{(3-5)}$cycloalkyl, $CH_2$—$OR^a$, $CH_2$—$NR^aR^b$, and COOH
with the proviso that at least one of $R^1$ or $R^2$ is $C_{(3-5)}$cycloalkyl;
Ring Ar represents:

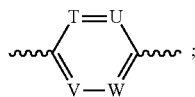

T, U and W are CH and V is CH or CF;
$L_1$ and $L_2$ together represent —NHC(=O)—;
A is absent or selected from —(CR'R")—, O, S(=O)$_q$, C(=X) and —NR$^a$;
R' and R" are the same or different and are independently selected from hydrogen, hydroxy, cyano, halogen, —OR$^a$, —COOR$^a$, —S(=O)$_q$—R$^a$, —NR$^a$R$^b$, —C(=X)—R$^a$, substituted or unsubstituted $C_{(1-6)}$alkyl group, substituted or unsubstituted $C_{(1-6)}$alkenyl, substituted or unsubstituted $C_{(1-6)}$alkynyl, and substituted or unsubstituted $C_{(3-5)}$cycloalkyl, or R' and R" may be joined to form a substituted or unsubstituted saturated or unsaturated 3-6 member ring, which may optionally include one or more heteroatoms which may be same or different and are selected from O, NR$^a$ and S;
each occurrence of X is independently selected from O, S and —NR$^a$;
Cy is a bicyclic ring selected from substituted or unsubstituted cycloalkyl group, substituted or unsubstituted heterocyclyl, substituted or unsubstituted aryl, and substituted or unsubstituted heteroaryl;
each occurrence of R$^a$ and R$^b$ are the same or different and are independently selected from hydrogen, nitro, hydroxy, cyano, halogen, —OR$^c$, —S(=O)$_q$—R$^c$, —NR$^c$R$^d$, —C(=Y)—R$^c$, —CR$^c$R$^d$—C(=Y)—R$^c$, —C(=Y)—NR$^c$R$^d$, —NR$^d$—C(=Y)—NR$^c$R$^d$, —S(=O)$_q$—NR$^c$R$^d$, —NR$^c$—S(=O)$_q$—NR$^c$R$^d$, —NR$^c$—NR$^c$R$^d$, substituted or unsubstituted alkyl, substituted or unsubstituted alkenyl, substituted or unsubstituted alkynyl, substituted or unsubstituted cycloalkyl, substituted or unsubstituted cycloalkylakyl, substituted or unsubstituted cycloalkenyl, substituted or unsubstituted heterocylyl, substituted or unsubstituted heterocyclylalkyl, substituted or unsubstituted aryl, substituted or unsubstituted arylalkyl, substituted or unsubstituted heteroaryl, and substituted or unsubstituted heteroarylalkyl, or when R$^a$ and R$^b$ are directly bound to the same atom, they may be joined to form a substituted or unsubstituted saturated or unsaturated 3-10 member ring, which may optionally include one or more heteroatoms which may be the same or different and are selected from O, NR$^c$ and S;
each occurrence of R$^c$ and R$^d$ may be same or different and are independently selected from hydrogen, nitro, hydroxy, cyano, halogen, substituted or unsubstituted alkyl, substituted or unsubstituted alkenyl, substituted or unsubstituted alkynyl, substituted or unsubstituted cycloalkyl, substituted or unsubstituted cycloalkylalkyl, substituted or unsubstituted cycloalkenyl, substituted or unsubstituted heterocyclic group, substituted or unsubstituted heterocyclylalkyl, or when two R$^c$ and/or R$^d$ substitutents are directly bound to the same atom, they may be joined to form a substituted or unsubstituted saturated or unsaturated 3-10 member ring, which may optionally include one or more heteroatoms which are the same or different and are selected from O, NH and S;
each occurrence of Y is selected from O, S and —NR$^a$; and
each occurrence of q independently represents 0, 1 or 2;
with the proviso that the compound of formula (I) is not:
N-[4-[5-cyclopropyl-3-(trifluoromethyl)-1H-pyrazol-1-yl]phenyl]-1-methyl-3-(trifluoromethyl)-1H-thieno[2,3-c]pyrazole-5-carboxamide or
N-[4-[5-cyclopropyl-3-(trifluoromethyl)-1H-pyrazol-1-yl]phenyl]-pyrazolo[1,5-a]pyrimidine-2-carboxamide.

2. The method of claim 1, wherein the non-small cell lung cancer cells express Orai1, Orai3, Stim1, or Stim2.

3. The method of claim 1, wherein the compound of formula (I) inhibits CRACM1/Orai1, CRACM2/Orai2, CRACM3/Orai3, or any combination thereof.

4. The method of claim 1, wherein the compound of formula (I) inhibits Stim1, or Stim2, or any combination thereof.

5. A method of treating a patient suffering from non-small cell lung cancer comprising:
(a) determining whether the cancer cells express Orai1, Orai3, Stim1, or Stim2; and
(b) for patients having cancer cells which express Orai1, Orai3, Stim1, or Stim2, administering to the patient an effective amount of a CRAC inhibitor to treat the non-small cell lung cancer, wherein the CRAC inhibitor is a compound of formula (I)

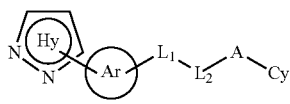

(I)

or a tautomer, N-oxide, pharmaceutically acceptable ester or pharmaceutically acceptable salt thereof, wherein
Ring Hy represents

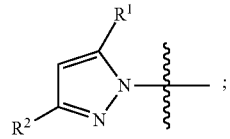

$R^1$ and $R^2$ are the same or different and are independently selected from $CH_3$, $CH_2F$, $CHF_2$, $CF_3$, substituted or unsubstituted $C_{(3-5)}$cycloalkyl, $CH_2$—$OR^a$, $CH_2$—$NR^aR^b$, and COOH
with the proviso that at least one of $R^1$ or $R^2$ is $C_{(3-5)}$cycloalkyl;

Ring Ar represents:

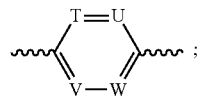

T, U and W are CH and V is CH or CF;
$L_1$ and $L_2$ together represent —NHC(=O)—;
A is absent or selected from —(CR'R")—, O, S(=O)$_q$, C(=X) and —NR$^a$;
R' and R" are the same or different and are independently selected from hydrogen, hydroxy, cyano, halogen, —ORa, —COOR$^a$, —S(=O)$_q$—R$^a$, —NR$^a$R$^b$, —C(=X)—R$^a$, substituted or unsubstituted C$_{(1-6)}$alkyl group, substituted or unsubstituted C$_{(1-6)}$alkenyl, substituted or unsubstituted C$_{(1-6)}$alkynyl, and substituted or unsubstituted C$_{(3-5)}$cycloalkyl, or R' and R" may be joined to form a substituted or unsubstituted saturated or unsaturated 3-6 member ring, which may optionally include one or more heteroatoms which may be same or different and are selected from O, NR$^a$ and S;
each occurrence of X is independently selected from O, S and —NR$^a$;
Cy is a bicyclic ring selected from substituted or unsubstituted cycloalkyl group, substituted or unsubstituted heterocyclyl, substituted or unsubstituted aryl, and substituted or unsubstituted heteroaryl;
each occurrence of R$^a$ and R$^b$ are the same or different and are independently selected from hydrogen, nitro, hydroxy, cyano, halogen, —OR$^c$, —S(=O)$_q$—R$^c$, —NR$^c$R$^d$, —C(=Y)—R$^c$, —CR$^c$R$^d$—C(=Y)—R$^c$, —C(=Y)—NR$^c$R$^d$, —NR$^d$—C(=Y)—NR$^c$R$^d$, —S(=O)$_q$—NR$^c$R$^d$, —NR$^c$—S(=O)$_q$—NR$^c$R$^d$, —NR$^c$—NR$^c$R$^d$, substituted or unsubstituted alkyl, substituted or unsubstituted alkenyl, substituted or unsubstituted alkynyl, substituted or unsubstituted cycloalkyl, substituted or unsubstituted cycloalkylakyl, substituted or unsubstituted cycloalkenyl, substituted or unsubstituted heterocyclyl, substituted or unsubstituted heterocyclylalkyl, substituted or unsubstituted aryl, substituted or unsubstituted arylalkyl, substituted or unsubstituted heteroaryl, and substituted or unsubstituted heteroarylalkyl, or when R$^a$ and R$^b$ are directly bound to the same atom, they may be joined to form a substituted or unsubstituted saturated or unsaturated 3-10 member ring, which may optionally include one or more heteroatoms which may be the same or different and are selected from O, NR$^c$ and S;
each occurrence of R$^c$ and R$^d$ may be same or different and are independently selected from hydrogen, nitro, hydroxy, cyano, halogen, substituted or unsubstituted alkyl, substituted or unsubstituted alkenyl, substituted or unsubstituted alkynyl, substituted or unsubstituted cycloalkyl, substituted or unsubstituted cycloalkylakyl, substituted or unsubstituted cycloalkenyl, substituted or unsubstituted heterocyclic group, substituted or unsubstituted heterocyclylalkyl, or when two R$^c$ and/or R$^d$ substitutents are directly bound to the same atom, they may be joined to form a substituted or unsubstituted saturated or unsaturated 3-10 member ring, which may optionally include one or more heteroatoms which are the same or different and are selected from O, NH and S;
each occurrence of Y is selected from O, S and —NR$^a$; and
each occurrence of q independently represents 0, 1 or 2;
with the proviso that the compound of formula (I) is not:
N-[4-[5-cyclopropyl-3-(trifluoromethyl)-1H-pyrazol-1-yl]phenyl]-1-methyl-3-(trifluoromethyl)-1H-thieno[2,3-c]pyrazole-5-carboxamide or
N-[4-[5-cyclopropyl-3-(trifluoromethyl)-1H-pyrazol-1-yl]phenyl]-pyrazolo[1,5-a]pyrimidine-2-carboxamide.

6. The method of claim 1, wherein $R^1$ and $R^2$ are the same or different and are independently selected from $CH_2F$, $CHF_2$, $CF_3$, and cyclopropyl with the proviso that at least one of $R^1$ or $R^2$ is cyclopropyl;
A is selected from —(CR'R")— and —NR$^a$;
each occurrence of R' and R" are the same or different and are independently selected from hydrogen or substituted or unsubstituted C$_{(1-6)}$alkyl group or R' and R" may be joined to form a substituted or unsubstituted saturated or unsaturated 3-6 membered ring, which may optionally include one or more heteroatoms which may be same or different and are selected from O, NR$^a$ and S; and
Cy is a bicyclic substituted or unsubstituted heteroaryl.

7. The method of claim 1, wherein the compound of formula (I) is selected from:
N-[4-(3,5-dicyclopropyl-1H-pyrazol-1-yl)phenyl]-1H-benzo[d]imidazole-6-carboxamide,
N-[4-(3,5-dicyclopropyl-1H-pyrazol-1-yl)phenyl]-1H-benzo[d][1,2,3]triazole-6-carboxamide,
N-[4-(3,5-dicyclopropyl-1H-pyrazol-1-yl)phenyl]quinoline-6-carboxamide,
N-[4-(3,5-dicyclopropyl-1H-pyrazol-1-yl)phenyl]quinoxaline-6-carboxamide,
2-(1H-benzo[d]imidazol-1-yl)-N-[4-(3,5-dicyclopropyl-1H-pyrazol-1-yl)phenyl]acetamide,
2-(1H-benzo[d][1,2,3]triazol-1-yl)-N-[4-(3,5-dicyclopropyl-1H-pyrazol-1-yl)phenyl]acetamide,
N-[4-(3,5-dicyclopropyl-1H-pyrazol-1-yl)phenyl]-2-(1H-indol-3-yl)acetamide,
N-[4-(3,5-dicyclopropyl-1H-pyrazol-1-yl)phenyl]-2-(imidazo[1,2-a]pyridin-2-yl)acetamide,
N-[4-(3,5-dicyclopropyl-1H-pyrazol-1-yl)phenyl]-2-(quinolin-6-yl)acetamide,
N-[4-(3,5-dicyclopropyl-1H-pyrazol-1-yl)phenyl]-2-(quinolin-6-yl)acetamide,
N-[4-(3,5-dicyclopropyl-1H-pyrazol-1-yl)-3-fluorophenyl]-2-(quinolin-6-yl)acetamide, N-[4-(4-chloro-3,5-dicyclopropyl-1H-pyrazol-1-yl)-3-fluorophenyl]-4-methyl-1,2,3-thiadiazole-5-carboxamide,
N-{4-[5-cyclopropyl-3-(trifluoromethyl)-1H-pyrazol-1-yl]phenyl}quinoline-6-carboxamide,
N-{4-[5-cyclopropyl-3-(trifluoromethyl)-1H-pyrazol-1-yl]phenyl}quinoxaline-6-carboxamide,
2-(1H-benzo[d]imidazol-1-yl)-N-{4-[5-cyclopropyl-3-(trifluoromethyl)-1H-pyrazol-1-yl]phenyl}acetamide,
2-(1H-benzo[d][1,2,3]triazol-1-yl)-N-{4-[5-cyclopropyl-3-(trifluoromethyl)-1H-pyrazol-1-yl]phenyl}acetamide,
2-(2H-benzo[d][1,2,3]triazol-2-yl)-N-{4-[5-cyclopropyl-3-(trifluoromethyl)-1H-pyrazol-1-yl]phenyl}acetamide,
2-(3H-[1,2,3]triazolo[4,5-b]pyridin-3-yl)-N-{4-[5-cyclopropyl-3-(trifluoromethyl)-1H-pyrazol-1-yl]phenyl}acetamide,
(S)-2-(3H-[1,2,3]triazolo[4,5-b]pyridin-3-yl)-N-{4-[5-cyclopropyl-3-(trifluoromethyl)-1H-pyrazol-1-yl]phenyl}propanamide,
2-(6-amino-9H-purin-9-yl)-N-{4-[5-cyclopropyl-3-(trifluoromethyl)-1H-pyrazol-1-yl]phenyl}acetamide,
N-(4-(5-cyclopropyl-3-(trifluoromethyl)-1H-pyrazol-1-yl)phenyl)-2-(1,3-dimethyl-2,6-dioxo-2,3-dihydro-1H-purin-7(6H)-yl)acetamide,
N-{4-[5-cyclopropyl-3-(trifluoromethyl)-1H-pyrazol-1-yl]phenyl)-2-(imidazo[1,2-a]pyridin-2-yl)acetamide,
N-{4-[5-cyclopropyl-3-(trifluoromethyl)-1H-pyrazol-1-yl]phenyl}-2-(quinolin-6-yl)acetamide,
N-{4-[5-cyclopropyl-3-(trifluoromethyl)-1H-pyrazol-1-yl]phenyl}-2-(quinolin-6-yl)propanamide,
N-{4-[5-cyclopropyl-3-(trifluoromethyl)-1H-pyrazol-1-yl]-3-fluorophenyl}-1H-benzo[d][1,2,3]triazole-6-carboxamide,
2-(1H-benzo[d][1,2,3]triazol-1-yl)-N-{4-[5-cyclopropyl-3-(trifluoromethyl)-1H-pyrazol-1-yl]-3-fluorophenyl}acetamide,
4-[5-cyclopropyl-3-(trifluoromethyl)-1H-pyrazol-1-yl]-3-fluoro-N-(quinolin-6-ylmethyl)benzamide, and
1-[4-(3,5-dicyclopropyl-1H-pyrazol-1-yl)phenyl]-3-(quinolin-6-yl)urea, or a tautomer, N-oxide, pharmaceutically acceptable ester, or pharmaceutically acceptable salt thereof.

8. The method of claim 1, wherein the compound of formula (I) is N-[4-(3,5-dicyclopropyl-1H-pyrazol-1-yl)phenyl]-2-(quinolin-6-yl)acetamide or a pharmaceutically acceptable salt thereof.

9. The method of claim 1, wherein the compound of formula (I) is 2-(1H-benzo[d]imidazol-1-yl)-N-{4-[5-cyclopropyl-3-(trifluoromethyl)-1H-pyrazol-1-yl]phenyl}acetamide or a pharmaceutically acceptable salt thereof.

10. The method of claim 5, wherein the CRAC inhibitor is selected from:
N-[4-(3,5-dicyclopropyl-1H-pyrazol-1-yl)phenyl]-1H-benzo[d]imidazole-6-carboxamide,
N-[4-(3,5-dicyclopropyl-1H-pyrazol-1-yl)phenyl]-1H-benzo[d][1,2,3]triazole-6-carboxamide,
N-[4-(3,5-dicyclopropyl-1H-pyrazol-1-yl)phenyl]quinoline-6-carboxamide,
N-[4-(3,5-dicyclopropyl-1H-pyrazol-1-yl)phenyl]quinoxaline-6-carboxamide,
2-(1H-benzo[d]imidazol-1-yl)-N-[4-(3,5-dicyclopropyl-1H-pyrazol-1-yl)phenyl]acetamide,
2-(1H-benzo[d][1,2,3]triazol-1-yl)-N-[4-(3,5-dicyclopropyl-1H-pyrazol-1-yl)phenyl]acetamide,
N-[4-(3,5-dicyclopropyl-1H-pyrazol-1-yl)phenyl]-2-(1H-indol-3-yl)acetamide,
N-[4-(3,5-dicyclopropyl-1H-pyrazol-1-yl)phenyl]-2-(imidazo[1,2-a]pyridin-2-yl)acetamide,
N-[4-(3,5-dicyclopropyl-1H-pyrazol-1-yl)phenyl]-2-(quinolin-6-yl)acetamide,
N-[4-(3,5-dicyclopropyl-1H-pyrazol-1-yl)phenyl]-2-(quinolin-6-yl)acetamide,
N-[4-(3,5-dicyclopropyl-1H-pyrazol-1-yl)-3-fluorophenyl]-2-(quinolin-6-yl)acetamide,
N-[4-(4-chloro-3,5-dicyclopropyl-1H-pyrazol-1-yl)-3-fluorophenyl]-4-methyl-1,2,3-thiadiazole-5-carboxamide,
N-{4-[5-cyclopropyl-3-(trifluoromethyl)-1H-pyrazol-1-yl]phenyl}quinoline-6-carboxamide,
N-{4-[5-cyclopropyl-3-(trifluoromethyl)-1H-pyrazol-1-yl]phenyl}quinoxaline-6-carboxamide,
2-(1H-benzo[d]imidazol-1-yl)-N-{4-[5-cyclopropyl-3-(trifluoromethyl)-1H-pyrazol-1-yl]phenyl}acetamide,
2-(1H-benzo[d][1,2,3]triazol-1-yl)-N-{4-[5-cyclopropyl-3-(trifluoromethyl)-1H-pyrazol-1-yl]phenyl}acetamide,
2-(2H-benzo[d][1,2,3]triazol-2-yl)-N-{4-[5-cyclopropyl-3-(trifluoromethyl)-1H-pyrazol-1-yl]phenyl}acetamide,
2-(3H-[1,2,3]triazolo[4,5-b]pyridin-3-yl)-N-{4-[5-cyclopropyl-3-(trifluoromethyl)-1H-pyrazol-1-yl]phenyl}acetamide,
(S)-2-(3H-[1,2,3]triazolo[4,5-b]pyridin-3-yl)-N-{4-[5-cyclopropyl-3-(trifluoromethyl)-1H-pyrazol-1-yl]phenyl}propanamide,
2-(6-amino-9H-purin-9-yl)-N-{4-[5-cyclopropyl-3-(trifluoromethyl)-1H-pyrazol-1-yl]phenyl}acetamide,
N-(4-(5-cyclopropyl-3-(trifluoromethyl)-1H-pyrazol-1-yl)phenyl)-2-(1,3-dimethyl-2,6-dioxo-2,3-dihydro-1H-purin-7(6H)-yl)acetamide,
N-{4-[5-cyclopropyl-3-(trifluoromethyl)-1H-pyrazol-1-yl]phenyl)-2-(imidazo[1,2-a]pyridin-2-yl)acetamide,
N-{4-[5-cyclopropyl-3-(trifluoromethyl)-1H-pyrazol-1-yl]phenyl}-2-(quinolin-6-yl)acetamide,
N-{4-[5-cyclopropyl-3-(trifluoromethyl)-1H-pyrazol-1-yl]phenyl}-2-(quinolin-6-yl)propanamide,
N-{4-[5-cyclopropyl-3-(trifluoromethyl)-1H-pyrazol-1-yl]-3-fluorophenyl}-1H-benzo[d][1,2,3]triazole-6-carboxamide,
2-(1H-benzo[d][1,2,3]triazol-1-yl)-N-{4-[5-cyclopropyl-3-(trifluoromethyl)-1H-pyrazol-1-yl]-3-fluorophenyl}acetamide,
4-[5-cyclopropyl-3-(trifluoromethyl)-1H-pyrazol-1-yl]-3-fluoro-N-(quinolin-6-ylmethyl)benzamide, and
1-[4-(3,5-dicyclopropyl-1H-pyrazol-1-yl)phenyl]-3-(quinolin-6-yl)urea, or a tautomer, N-oxide, pharmaceutically acceptable ester, or pharmaceutically acceptable salt thereof.

11. The method of claim 5, wherein the CRAC inhibitor is N-[4-(3,5-dicyclopropyl-1H-pyrazol-1-yl)phenyl]-2-(quinolin-6-yl)acetamide or a pharmaceutically acceptable salt thereof.

12. The method of claim 5, wherein the CRAC inhibitor is 2-(1H-benzo[d]imidazol-1-yl)-N-{4-[5-cyclopropyl-3-(trifluoromethyl)-1H-pyrazol-1-yl]phenyl}acetamide or a pharmaceutically acceptable salt thereof.

13. The method of claim 5, wherein
$R^1$ and $R^2$ are the same or different and are independently selected from $CH_2F$, $CHF_2$, $CF_3$, and cyclopropyl with the proviso that at least one of $R^1$ or $R^2$ is cyclopropyl;

A is selected from —(CR'R")— and —NR$^a$;

each occurrence of R' and R" are the same or different and are independently selected from hydrogen or substituted or unsubstituted C$_{(1-6)}$alkyl group or R' and R" may be joined to form a substituted or unsubstituted saturated or unsaturated 3-6 membered ring, which may optionally include one or more heteroatoms which may be same or different and are selected from O, NR$^a$ and S; and Cy is a bicyclic substituted or unsubstituted heteroaryl.

14. A method of treating a patient suffering from non-small cell lung cancer comprising:
(a) determining whether the cancer cells express Orai1 or Stim1; and
(b) for patients having cancer cells which express Orai1 or Stim1, administering to the patient an effective amount of a CRAC inhibitor which inhibits CRACM1/Orai1 or Stim1 to treat the non-small cell lung cancer, wherein the CRAC inhibitor is a compound of formula (I)

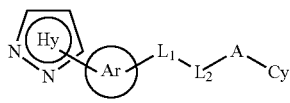

(I)

or a tautomer, N-oxide, pharmaceutically acceptable ester or pharmaceutically acceptable salt thereof, wherein Ring Hy represents

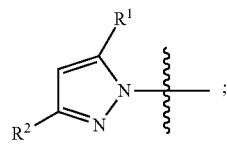

R$^1$ and R$^2$ are the same or different and are independently selected from CH$_3$, CH$_2$F, CHF$_2$, CF$_3$, substituted or unsubstituted C$_{(3-5)}$cycloalkyl, CH$_2$—OR$^a$, CH$_2$—NR$^a$R$^b$, and COOH with the proviso that at least one of R$^1$ or R$^2$ is C$_{(3-5)}$cycloalkyl;

Ring Ar represents:

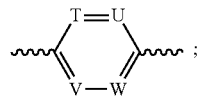

T, U and W are CH and V is CH or CF;

L$_1$ and L$_2$ together represent —NHC(=O)—;

A is absent or selected from —(CR'R")—, O, S(=O)$_q$, C(=X) and —NR$^a$;

R' and R" are the same or different and are independently selected from hydrogen, hydroxy, cyano, halogen, —OR$^a$, —COOR$^a$, —S(=O)$_q$—R$^a$, —NR$^a$R$^b$, —C(=X)—R$^a$, substituted or unsubstituted C$_{(1-6)}$alkyl group, substituted or unsubstituted C$_{(1-6)}$alkenyl, substituted or unsubstituted C$_{(1-6)}$alkynyl, and substituted or unsubstituted C$_{(3-5)}$cycloalkyl, or R' and R" may be joined to form a substituted or unsubstituted saturated or unsaturated 3-6 member ring, which may optionally include one or more heteroatoms which may be same or different and are selected from O, NR$^a$ and S;

each occurrence of X is independently selected from O, S and —NR$^a$;

Cy is a bicyclic ring selected from substituted or unsubstituted cycloalkyl group, substituted or unsubstituted heterocyclyl, substituted or unsubstituted aryl, and substituted or unsubstituted heteroaryl;

each occurrence of R$^a$ and R$^b$ are the same or different and are independently selected from hydrogen, nitro, hydroxy, cyano, halogen, —OR$^c$, —S(=O)$_q$—R$^c$, —NR$^c$R$^d$, —C(=Y)—R$^c$, —CR$^c$R$^d$—C(=Y)—R$^c$, —C(=Y)—NR$^c$R$^d$, —NR$^d$—C(=Y)—NR$^c$R$^d$, —S(=O)—NR$^c$R$^d$, —NR$^c$—S(=O)$_q$—NR$^c$R$^d$, —NR$^c$—NR$^c$R$^d$, substituted or unsubstituted alkyl, substituted or unsubstituted alkenyl, substituted or unsubstituted alkynyl, substituted or unsubstituted cycloalkyl, substituted or unsubstituted cycloalkylakyl, substituted or unsubstituted cycloalkenyl, substituted or unsubstituted heterocylyl, substituted or unsubstituted heterocyclylalkyl, substituted or unsubstituted aryl, substituted or unsubstituted arylalkyl, substituted or unsubstituted heteroaryl, and substituted or unsubstituted heteroarylalkyl, or when R$^a$ and R$^b$ are directly bound to the same atom, they may be joined to form a substituted or unsubstituted saturated or unsaturated 3-10 member ring, which may optionally include one or more heteroatoms which may be the same or different and are selected from O, NR$^c$ and S;

each occurrence of R$^c$ and R$^d$ may be same or different and are independently selected from hydrogen, nitro, hydroxy, cyano, halogen, substituted or unsubstituted alkyl, substituted or unsubstituted alkenyl, substituted or unsubstituted alkynyl, substituted or unsubstituted cycloalkyl, substituted or unsubstituted cycloalkylakyl, substituted or unsubstituted cycloalkenyl, substituted or unsubstituted heterocyclic group, substituted or unsubstituted heterocyclylalkyl, or when two R$^c$ and/or R$^d$ substitutents are directly bound to the same atom, they may be joined to form a substituted or unsubstituted saturated or unsaturated 3-10 member ring, which may optionally include one or more heteroatoms which are the same or different and are selected from O, NH and S;

each occurrence of Y is selected from O, S and —NR$^a$; and each occurrence of q independently represents 0, 1 or 2;

with the proviso that the compound of formula (I) is not:
N-[4-[5-cyclopropyl-3-(trifluoromethyl)-1H-pyrazol-1-yl]phenyl]-1-methyl-3-(trifluoromethyl)-1H-thieno[2,3-c]pyrazole-5-carboxamide or N-[4-[5-cyclopropyl-3-(trifluoromethyl)-1H-pyrazol-1-yl]phenyl]-pyrazolo[1,5-a]pyrimidine-2-carboxamide.

* * * * *